United States Patent
Wightman

(10) Patent No.: US 7,799,800 B2
(45) Date of Patent: Sep. 21, 2010

(54) LIPID-MODIFIED IMMUNE RESPONSE MODIFIERS

(75) Inventor: Paul D. Wightman, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 888 days.

(21) Appl. No.: 10/595,066

(22) PCT Filed: Aug. 12, 2004

(86) PCT No.: PCT/US2004/026157

§ 371 (c)(1), (2), (4) Date: Jan. 27, 2006

(87) PCT Pub. No.: WO2005/018555

PCT Pub. Date: Mar. 3, 2005

(65) Prior Publication Data

US 2006/0189644 A1    Aug. 24, 2006

Related U.S. Application Data

(60) Provisional application No. 60/515,604, filed on Oct. 30, 2003, provisional application No. 60/544,561, filed on Feb. 13, 2004.

(51) Int. Cl.
*A61K 31/445* (2006.01)
*C07D 513/02* (2006.01)
*C07D 515/02* (2006.01)

(52) U.S. Cl. ................... 514/303; 546/118
(58) Field of Classification Search ........... 546/82, 546/84, 118; 514/293, 303
See application file for complete search history.

(56) References Cited

U.S. PATENT DOCUMENTS

| | | | |
|---|---|---|---|
| 3,314,941 A | 4/1967 | Littell et al. | |
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gerster | |
| 5,346,905 A | 9/1994 | Gerster | |
| 5,352,784 A | 10/1994 | Nikolaides et al. | |
| 5,367,076 A | 11/1994 | Gerster | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,693,811 A | 12/1997 | Lindstrom | |
| 5,741,908 A | 4/1998 | Gerster et al. | |
| 5,756,747 A | 5/1998 | Gerster | |
| 5,939,090 A | 8/1999 | Beaurline et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,245,776 B1 | 6/2001 | Skwierczynski et al. | |
| 6,331,539 B1 | 12/2001 | Crooks et al. | |
| 6,376,669 B1 | 4/2002 | Rice et al. | |
| 6,451,810 B1 | 9/2002 | Coleman et al. | |
| 6,518,265 B1 | 2/2003 | Kato et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,576,636 B2 | 6/2003 | Webb et al. | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |

(Continued)

FOREIGN PATENT DOCUMENTS

EP    0 394 026    10/1990

(Continued)

OTHER PUBLICATIONS

Bachman, et al, "Synthesis of Substituted Quinolylamines. Derivatives of 4-Amino-7-Chloroquinoline", *J. Org. Chem*, 15, pp. 1278-1284 (1950).

(Continued)

*Primary Examiner*—James O. Wilson
*Assistant Examiner*—Paul V. Ward
(74) *Attorney, Agent, or Firm*—Kathleen B. Gross; Dean A. Ersfeld

(57) ABSTRACT

Lipid-modified immune response modifier compounds, pharmaceutical compositions containing the compounds and methods of use of these compounds as immunomodulators, for inducing or inhibiting cytokine biosynthesis in animals and in the treatment of diseases including viral and neoplastic diseases, are disclosed.

14 Claims, 1 Drawing Sheet

U.S. PATENT DOCUMENTS

| | | | |
|---|---|---|---|
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,696,465 | B2 | 2/2004 | Dellaria et al. |
| 6,706,728 | B2 | 3/2004 | Hedenstrom et al. |
| 6,743,920 | B2 | 6/2004 | Lindstrom et al. |
| 6,756,382 | B2 | 6/2004 | Coleman et al. |
| 6,797,718 | B2 | 9/2004 | Dellaria et al. |
| 6,818,650 | B2 | 11/2004 | Griesgraber |
| 6,841,678 | B2 | 1/2005 | Merli et al. |
| 6,852,861 | B2 | 2/2005 | Merli et al. |
| 7,091,214 | B2 * | 8/2006 | Hays et al. .................. 514/293 |
| 7,427,629 | B2 * | 9/2008 | Kedl et al. .................. 514/279 |
| 2002/0016332 | A1 | 2/2002 | Slade |
| 2002/0055517 | A1 | 5/2002 | Smith |
| 2002/0058674 | A1 | 5/2002 | Hedenstrom et al. |
| 2002/0107262 | A1 | 8/2002 | Lindstrom |
| 2002/0110840 | A1 | 8/2002 | Tomai et al. |
| 2003/0096835 | A1 | 5/2003 | Crooks et al. |
| 2003/0130299 | A1 | 7/2003 | Crooks et al. |
| 2003/0133913 | A1 | 7/2003 | Tomai et al. |
| 2003/0139364 | A1 | 7/2003 | Krieg et al. |
| 2003/0144286 | A1 | 7/2003 | Frenkel et al. |
| 2003/0161797 | A1 | 8/2003 | Miller et al. |
| 2003/0199538 | A1 | 10/2003 | Skwierczynski et al. |
| 2004/0014779 | A1 | 1/2004 | Gorden et al. |
| 2004/0091491 | A1 | 5/2004 | Kedl et al. |
| 2004/0106589 | A1 | 6/2004 | Webb et al. |
| 2004/0132079 | A1 | 7/2004 | Gupta et al. |
| 2004/0141950 | A1 | 7/2004 | Noelle et al. |
| 2004/0147543 | A1 | 7/2004 | Hays et al. |
| 2004/0162309 | A1 | 8/2004 | Gorden et al. |
| 2004/0171086 | A1 | 9/2004 | Fink et al. |
| 2004/0175336 | A1 | 9/2004 | Egging et al. |
| 2004/0176367 | A1 | 9/2004 | Griesgraber et al. |
| 2004/0180919 | A1 | 9/2004 | Lee et al. |
| 2004/0181130 | A1 | 9/2004 | Fox et al. |
| 2004/0181211 | A1 | 9/2004 | Elliot et al. |
| 2004/0191833 | A1 | 9/2004 | Fink et al. |
| 2004/0192585 | A1 | 9/2004 | Fox et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |
| 2005/0054590 | A1 | 3/2005 | Averett |
| 2005/0085500 | A1 | 4/2005 | Gutman et al. |
| 2005/0165236 | A1 | 7/2005 | Colombo et al. |
| 2005/0245562 | A1 | 11/2005 | Garcia-Echeverria et al. |
| 2006/0100229 | A1 | 5/2006 | Hays et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |

OTHER PUBLICATIONS

Baranov, et al., *Chem. Abs.* 85, 94362, (1976).

Berényi, et al, "Ring Transformation of Condensed Dihydro-as-triazines", *J. Heterocyclic Chem.*, 18, pp. 1537-1540 (1981).

Brennan, et al, "Automated Bioassay of Interferons in Micro-test Plates", *Biotechniques,* Jun./Jul. 78, 1983.

Chollet, et al, "Development of a Topically Active Imiquimod Formulation", *Pharmaceutical Development and Technology,* 4(1), pp. 35-43 (1999).

Izumi, et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines", *Bioorganic & Medicinal Chemistry,* 11, pp. 2541-2550 (2003).

Jain, et al, "Chemical and Pharmacological Investigations of Some ω-Substituted Alkylamino-3-aminopyridines", *J. Med. Chem.*, 11, pp. 87-92 (1968).

Kedl, et al. "T Cells Compete for Access to Antigen-bearing Antigen-presenting Cells", *The Journal of Experimental Medicine*, vol. 192, Oct. 16, 2000.

Testerman, et al., "Cytokine Induction by the Immunomodulators Imiquimod and S-27609", *Journal of Leukocyte Biology*, vol. 58, pp. 365-372, Sep. 1995.

Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Society,* 102, pp. 511-513, Dec. 12, 1983.

\* cited by examiner

LIPID-MODIFIED IMMUNE RESPONSE MODIFIERS

CROSS-REFERENCE TO RELATED APPLICATIONS

This application is the National Stage of International Application No. PCT/US2004/026157, filed Aug. 12, 2004, which claims priority to U.S. patent application Ser. No. 10/640,904, filed on Aug. 14, 2003, U.S. Pat. No. 7,427,629, and to U.S. Provisional Patent Application Ser. Nos. 60/515,604, filed on Oct. 30, 2003, and 60/544,561, filed on Feb. 13, 2004, each of which is incorporated herein by reference in their entirety.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in and a need for compounds that have the ability to modulate the immune response, by induction of cytokine biosynthesis or other mechanisms.

SUMMARY

A new class of compounds useful for modulating cytokine biosynthesis has now been found. In one aspect, the present invention provides an IRM compound covalently bound to an $R_1$ group wherein $R_1$ is as defined below; and pharmaceutically acceptable salts thereof. In one embodiment, the present invention provides such compounds, which are of Formula I:

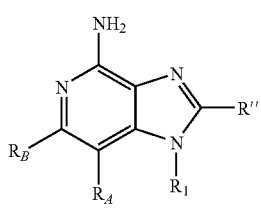

I wherein $R_A$, $R_B$, $R_1$, and R" are as defined below; and pharmaceutically acceptable salts thereof.

Examples of such compounds include those of the following Formulas II, III, IV, V, VI, and VII:

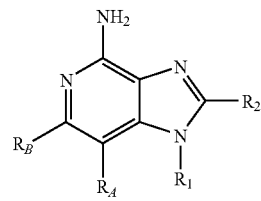

II

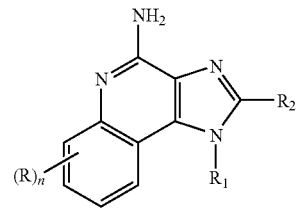

III

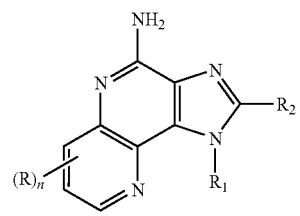

IV

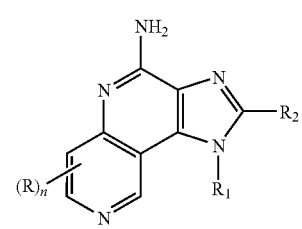

V

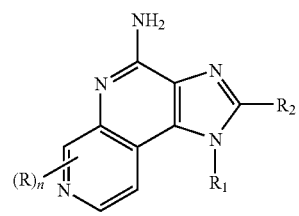

VI

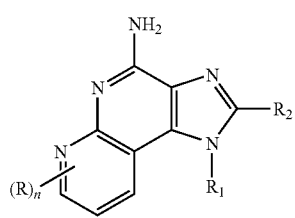

VII wherein R, $R_A$, $R_B$, $R_1$, $R_2$, and n are as defined below; and pharmaceutically acceptable salts thereof.

IRM compounds covalently bound to an $R_1$ group including the compounds of Formula I are useful as immune response modifiers (IRMs) due to their ability to induce or inhibit cytokine biosynthesis (e.g., induce or inhibit the biosynthesis or production of one or more cytokines) and otherwise modulate the immune response when administered to animals. This makes the compounds useful in the treatment of a variety of conditions such as viral diseases, neoplastic diseases, and autoimmune diseases that are responsive to such changes in the immune response.

In another aspect, the present invention provides pharmaceutical compositions containing the immune response modifier compounds, and methods of inducing or inhibiting cytokine biosynthesis in an animal, treating a viral disease in an animal, and treating a neoplastic disease in an animal, by administering an effective amount of one or more compounds of Formula I and/or pharmaceutically acceptable salts thereof to the animal.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

Figure 1:
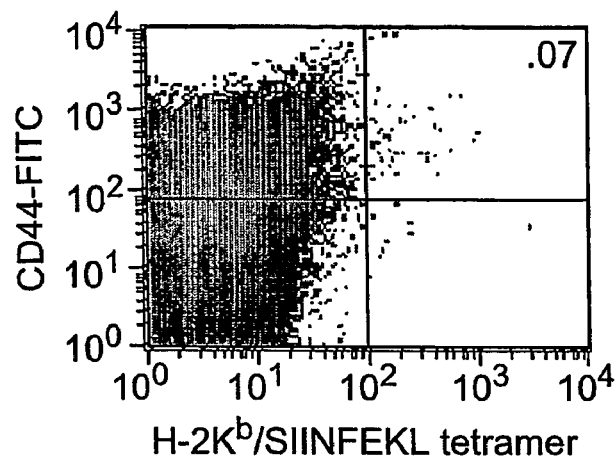
FIG. 1 shows expansion of antigen-specific $CD8^+$ T cells after immunization with ovalbumin, as described in Example 5.

The present invention provides a new class of compounds in which an IRM compound is covalently bound to an $R_1$ group wherein $R_1$ is as defined below; and pharmaceutically acceptable salts thereof. More specifically, the present invention provides compounds of the following Formulas I through VII:

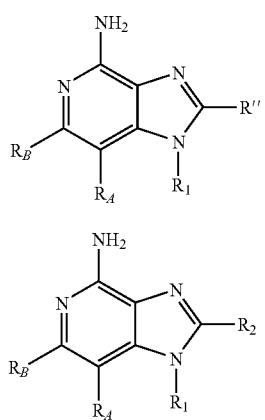

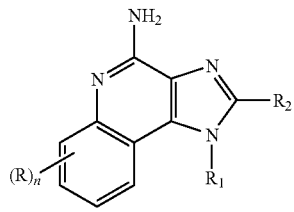

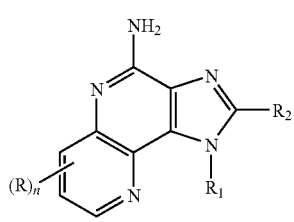

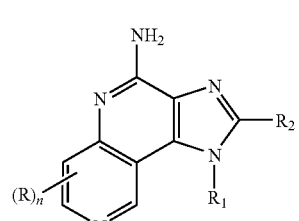

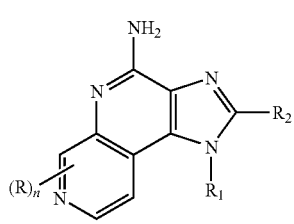

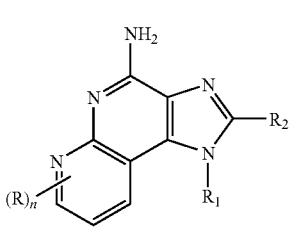

wherein R, $R_A$, $R_B$, $R_1$, $R_2$, R", and n are as defined below; and pharmaceutically acceptable salts thereof.

In one aspect, the present invention provides an IRM compound covalently bound to an $R_1$ group wherein $R_1$ has the formula alkylene-L-$R_{1-1}$, alkenylene-L-$R_{1-1}$, or alkynylene-L-$R_{1-1}$, wherein:

the alkylene, alkenylene, and alkynylene groups are optionally interrupted with one or more —O— groups (preferably, interrupted with one —O— group);

L is a bond or a functional linking group; and $R_{1-1}$ is a linear or branched aliphatic group having at least 11 carbon atoms (preferably, at least 12 carbon atoms), optionally including one or more unsaturated carbon-carbon bonds; or a pharmaceutically acceptable salt thereof; with the proviso that for a compound of Formula I:

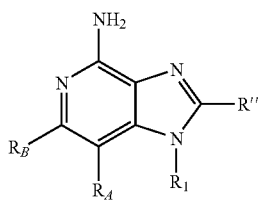

when L is —NH—S(O)$_2$— and R$_A$ and R$_B$ join to form an unsubstituted benzene ring, R$_{1-1}$ is a linear or branched aliphatic group having greater than 16 carbon atoms, optionally including one or more unsaturated carbon-carbon bonds; and with the further proviso that for a compound of Formula I when L is —NH—C(O)— and R$_A$ and R$_B$ join to form an unsubstituted pyridine ring, R$_{1-1}$ is a linear or branched aliphatic group having greater than 11 carbon atoms, optionally including one or more unsaturated carbon-carbon bonds.

In one embodiment, the present invention provides compounds of the following Formula I:

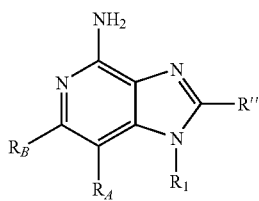

wherein:
R$_1$ has the formula alkylene-L-R$_{1-1}$, alkenylene-L-R$_{1-1}$, or alkynylene-L-R$_{1-1}$, wherein:
the alkylene, alkenylene, and alkynylene groups are optionally interrupted with one or more —O— groups (preferably, with one —O— group);
L is a bond or a functional linking group; and
R$_{1-1}$ is a linear or branched aliphatic group having at least 11 carbon atoms (preferably, at least 12 carbon atoms), optionally including one or more unsaturated carbon-carbon bonds;
R" is hydrogen or a non-interfering substituent;
R$_A$ and R$_B$ are each independently selected from the group consisting of:
hydrogen,
halogen,
alkyl,
alkenyl,
alkoxy,
alkylthio, and
—N(R$_3$)$_2$;
or when taken together, R$_A$ and R$_B$ form a fused aryl ring or heteroaryl ring containing one heteroatom or a fused 5- to 7-membered saturated ring, optionally containing one heteroatom, wherein the heteroatom is selected from the group consisting of N and S, and wherein the aryl, heteroaryl, or 5- to 7-membered saturated ring is unsubstituted or substituted by one or more non-interfering substituents; and
R$_3$ is selected from the group consisting of hydrogen and alkyl; with the proviso that when L is —NH—S(O)$_2$— and R$_A$ and R$_B$ join to form an unsubstituted benzene ring, R$_{1-1}$ is a linear or branched aliphatic group having greater than 16 carbon atoms, optionally including one or more unsaturated carbon-carbon bonds; and with the further proviso that when L is —NH—C(O)— and R$_A$ and R$_B$ join to form an unsubstituted pyridine ring, R$_{1-1}$ is a linear or branched aliphatic group having greater than 11 carbon atoms, optionally including one or more unsaturated carbon-carbon bonds;

or a pharmaceutically acceptable salt thereof.

In one embodiment, the present invention provides compounds of the following Formula II:

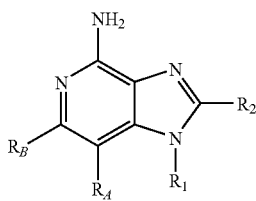

wherein:
R$_1$ has the formula alkylene-L-R$_{1-1}$, alkenylene-L-R$_{1-1}$, or alkynylene-L-R$_{1-1}$, wherein:
the alkylene, alkenylene, and alkynylene groups are optionally interrupted with one or more —O— groups (preferably, with one —O— group);
L is a bond or a functional linking group selected from the group consisting of —NH—S(O)$_2$—, —NH—C(O)—, —NH—C(S)—, —NH—S(O)$_2$—NR$_3$—, —NH—C(O)—NR$_3$—, —NH—C(S)—NR$_3$—, —NH—C(O)—O—, —O—, —S—, and —S(O)$_2$—; and
R$_{1-1}$ is a linear or branched aliphatic group having at least 11 carbon atoms (preferably, at least 12 carbon atoms), optionally including one or more unsaturated carbon-carbon bonds;
R$_2$ is selected from the group consisting of:
hydrogen;
alkyl;
alkenyl;
aryl;
heteroaryl;
heterocyclyl;
alkylene-Y-alkyl;
alkylene-Y-alkenyl;
alkylene-Y-aryl; and
alkyl or alkenyl substituted by one or more substituents selected from the group consisting of:
—OH;
halogen;
—N(R$_4$)$_2$;
—C(O)—C$_{1-10}$alkyl;
—C(O)—O—C$_{1-10}$alkyl;
—N$_3$;
aryl;
heteroaryl;
heterocyclyl;
—C(O)-aryl; and
—C(O)-heteroaryl;
wherein: Y is —O— or —S(O)$_{0-2}$—; and each R$_4$ is independently selected from the group consisting of hydrogen, C$_{1-10}$alkyl, and C$_{2-10}$alkenyl;
R$_A$ and R$_B$ are each independently selected from the group consisting of:
hydrogen,
halogen, alkyl,
alkenyl,
alkoxy,
alkylthio, and
—N(R$_3$)$_2$;
or when taken together, R$_A$ and R$_B$ form a fused aryl ring or heteroaryl ring containing one heteroatom wherein the aryl or heteroaryl ring is unsubstituted or substituted by one or more R groups; or when taken together, R$_A$ and R$_B$ form a fused 5- to 7-membered saturated ring, optionally containing one heteroatom selected from the group consisting of N and S, and unsubstituted or substituted by one or more R groups; wherein R is selected from the group consisting of
halogen,
hydroxy,
alkyl,
alkenyl,
haloalkyl,
alkoxy,
alkylthio, and
—N(R$_3$)$_2$.
and
R$_3$ is selected from the group consisting of hydrogen and alkyl; with the proviso that when L is —NH—S(O)$_2$— and R$_A$ and R$_B$ join to form an unsubstituted benzene ring, R$_{1-1}$ is a linear or branched aliphatic group having at least 16 carbon atoms, optionally including one or more unsaturated carbon-carbon bonds; and with the further proviso that when L is —NH—C(O)— and R$_A$ and R$_B$ join to form an unsubstituted pyridine ring, R$_{1-1}$ is a linear or branched aliphatic group having greater than 11 carbon atoms, optionally including one or more unsaturated carbon-carbon bonds;

or a pharmaceutically acceptable salt thereof.

In another embodiment, the present invention provides compounds of the following Formula II:

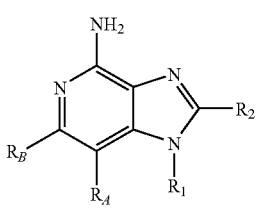

wherein:
R$_1$ has the formula alkylene-L-R$_{1-1}$, alkenylene-L-R$_{1-1}$, or alkynylene-L-R$_{1-1}$, wherein:
the alkylene, alkenylene, and alkynylene groups are optionally interrupted with one or more —O— groups (preferably, with one —O— group);
L is a bond or a functional linking group selected from the group consisting of —NH—S(O)$_2$—, —NH—C(O)—, —NH—C(S)—, —NH—S(O)$_2$—NR$_3$—, —NH—C(O)—NR$_3$—, —NH—C(S)—NR$_3$—, —NH—C(O)—O—, —O—, —S—, and —S(O)$_2$—; and
R$_{1-1}$ is a linear or branched aliphatic group having at least 11 carbon atoms (preferably, at least 12 carbon atoms), optionally including one or more unsaturated carbon-carbon bonds;
R$_2$ is selected from the group consisting of:
hydrogen;
alkyl;
alkenyl;
aryl;
heteroaryl;
heterocyclyl;
alkylene-Y-alkyl;
alkylene-Y-alkenyl;
alkylene-Y-aryl; and
alkyl or alkenyl substituted by one or more substituents selected from the group consisting of:
—OH;
halogen;
—N(R$_4$)$_2$;
—C(O)—C$_{1-10}$alkyl;
—C(O)—O—C$_{1-10}$alkyl;
—N$_3$;
aryl;
heteroaryl;
heterocyclyl;
—C(O)-aryl; and
—C(O)-heteroaryl;
wherein: Y is —O— or —S(O)$_{0-2}$—; and each R$_4$ is independently selected from the group consisting of hydrogen, C$_{1-10}$alkyl, and C$_{2-10}$alkenyl;
R$_A$ and R$_B$ are each independently selected from the group consisting of:
hydrogen,
halogen,
alkyl,
alkenyl,
alkoxy,
alkylthio, and
—N(R$_3$)$_2$; and
R$_3$ is selected from the group consisting of hydrogen and alkyl;

or a pharmaceutically acceptable salt thereof.

In another embodiment, the present invention provides compounds of the following Formula III:

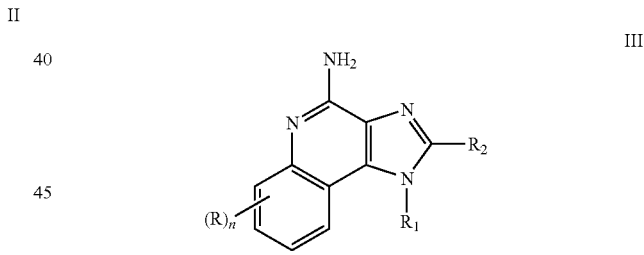

wherein:
R$_1$ has the formula alkylene-L-R$_{1-1}$, alkenylene-L-R$_{1-1}$, or alkynylene-L-R$_{1-1}$, wherein:
the alkylene, alkenylene, and alkynylene groups are optionally interrupted with one or more —O— groups (preferably, with one —O— group);
L is a bond or a functional linking group selected from the group consisting of —NH—S(O)$_2$—, —NH—C(O)—, —NH—C(S)—, —NH—S(O)$_2$—NR$_3$—, —NH—C(O)—NR$_3$—, —NH—C(S)—NR$_3$—, —NH—C(O)—O—, —O—, —S—, and —S(O)$_2$—; and
R$_{1-1}$ is a linear or branched aliphatic group having at least 11 carbon atoms (preferably, at least 12 carbon atoms), optionally including one or more unsaturated carbon-carbon bonds;
R is selected from the group consisting of
halogen,
hydroxy, alkyl,
alkenyl,
haloalkyl,
alkoxy,
alkylthio, and
—N(R$_3$)$_2$;
n is 0 to 4;
R$_2$ is selected from the group consisting of:
hydrogen;
alkyl;
alkenyl;
aryl;
heteroaryl;
heterocyclyl;
alkylene-Y-alkyl;
alkylene-Y-alkenyl;
alkylene-Y-aryl; and
alkyl or alkenyl substituted by one or more substituents selected from the group consisting of:
—OH;
halogen;
—N(R$_4$)$_2$;
—C(O)—C$_{1-10}$alkyl;
—C(O)—O—C$_{1-10}$alkyl;
—N$_3$;
aryl;
heteroaryl;
heterocyclyl;
—C(O)-aryl; and
—C(O)-heteroaryl;
Y is —O— or —S(O)$_{0-2}$—;
each R$_4$ is independently selected from the group consisting of hydrogen, C$_{1-10}$alkyl, and C$_{2-10}$alkenyl; and
R$_3$ is selected from the group consisting of hydrogen and alkyl; with the proviso that when L is —NH—S(O$_2$)—, and n is 0, R$_{1-1}$ is a linear or branched aliphatic group having at least 16 carbon atoms, optionally including one or more unsaturated carbon-carbon bonds;

or a pharmaceutically acceptable salt thereof.

In other embodiments, the present invention provides compounds of the following Formulas IV, V, VI, and VII:

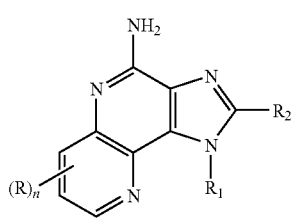

IV

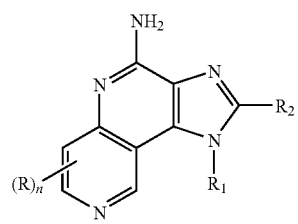

V

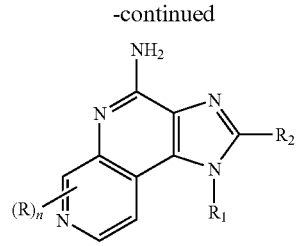

VI

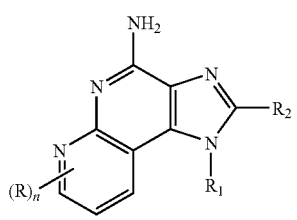

VII wherein:
R$_1$ has the formula alkylene-L-R$_{1-1}$, alkenylene-L-R$_{1-1}$, or alkynylene-L-R$_{1-1}$, wherein:
the alkylene, alkenylene, and alkynylene groups are optionally interrupted with one or more —O— groups (preferably, with one —O— group);
L is a bond or a functional linking group selected from the group consisting of —NH—S(O)$_2$—, —NH—C(O)—, —NH—C(S)—, —NH—S(O)$_2$—NR$_3$—, —NH—C(O)—NR$_3$—, —NH—C(S)—NR$_3$—, —NH—C(O)—O—, —O—, —S—, and —S(O)$_2$—; and
R$_{1-1}$ is a linear or branched aliphatic group having at least 11 carbon atoms (preferably, at least 12 carbon atoms), optionally including one or more unsaturated carbon-carbon bonds;
R is selected from the group consisting of
halogen,
hydroxy,
alkyl,
alkenyl,
haloalkyl,
alkoxy,
alkylthio, and
—N(R$_3$)$_2$;
n is 0 or 1;
R$_2$ is selected from the group consisting of:
hydrogen;
alkyl;
alkenyl;
aryl;
heteroaryl;
heterocyclyl;
alkylene-Y-alkyl;
alkylene-Y-alkenyl;
alkylene-Y-aryl; and
alkyl or alkenyl substituted by one or more substituents selected from the group consisting of:
—OH;
halogen;
—N(R$_4$)$_2$;
—C(O)—C$_{1-10}$alkyl;
—C(O)—O—C$_{1-10}$alkyl;
—N$_3$;
aryl;
heteroaryl;
heterocyclyl;

—C(O)-aryl; and
—C(O)-heteroaryl;

Y is —O— or —S(O)$_{0-2}$—;

each $R_4$ is independently selected from the group consisting of hydrogen, $C_{1-10}$alkyl, and $C_{2-10}$alkenyl; and $R_3$ is selected from the group consisting of hydrogen and alkyl; with the proviso that when L is —NH—C(O)—, and n is 0, $R_{1-1}$ is a linear or branched aliphatic group having at least 12 carbon atoms, optionally including one or more unsaturated carbon-carbon bonds;

or a pharmaceutically acceptable salt thereof.

In the context of the present invention, the term "aliphatic" group means a saturated or unsaturated linear or branched hydrocarbon group. This term is used to encompass alkyl, alkenyl, and alkynyl groups, for example.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. Likewise, "alkylenyl," "alkenylenyl," and "alkynylenyl" are the divalent forms of the "alkyl," "alkenyl," and "alkynyl" groups defined above. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, and the like.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_3$)$_2$ each $R_3$ group is independently selected. In another example, when more than one R group is present and each R group contains one or more —N($R_3$)$_2$ groups, then each R group is independently selected, and each $R_3$ group is independently selected.

The invention is inclusive of the compounds described herein, and salts thereof, in any of their pharmaceutically acceptable forms, including isomers (e.g., diastereomers and enantiomers), solvates, polymorphs, and the like. In particular, if a compound is optically active, the invention specifically includes each of the compound's enantiomers as well as racemic mixtures of the enantiomers.

In some embodiments, compounds of Formulas I-VII induce the biosynthesis of one or more cytokines.

For any of the compounds presented herein, each one of the following variables (e.g., R, R", $R_1$, $R_2$, $R_4$, $R_B$, n, L, and so on) in any of its embodiments can be combined with any one or more of the other variables in any of their embodiments as would be understood by one of skill in the art. Each of the resulting combinations of variables is an embodiment of the present invention.

For certain embodiments, R" is hydrogen or a non-interfering substituent. Herein, "non-interfering" means that the ability of the compound or salt to modulate (e.g., induce or inhibit) the biosynthesis of one or more cytokines is not destroyed by the non-interfering substitutent. Illustrative non-interfering R" groups include those described herein for $R_2$. Preferred embodiments of R" and $R_2$ are listed below.

The present invention provides an IRM compound covalently bound to an $R_1$ group. Herein, $R_1$ has the formula alkylene-L-$R_{1-1}$, alkenylene-L-$R_{1-1}$, or alkynylene-L-$R_{1-1}$, wherein the alkylene, alkenylene, and alkynylene groups are optionally interrupted with one or more —O— groups; L is a bond or a functional linking group; and $R_{1-1}$ is a linear or branched aliphatic group having at least 11 carbon atoms, optionally including one or more unsaturated carbon-carbon bonds. In some embodiments, the IRM compound is not imiquimod.

In some embodiments of Formulas I-VII, the alkylene, alkenylene, and alkynylene groups within $R_1$ are linear or branched. In certain embodiments the alkylene, alkenylene, and alkynylene groups within $R_1$ are linear. In some embodiments the alkylene, alkenylene, and alkynylene groups are interrupted with one or more —O— groups. In some embodiments, the alkylene, alkenylene, and alkynylene groups are interrupted with one —O— group.

Herein, the $R_1$ is also referred to as Q-L-$R_{1-1}$ wherein Q is an alkylene, alkenylene, or alkynylene optionally interrupted with one or more —O— groups. In some embodiments, Q is an alkylene optionally interrupted with one oxygen atom (i.e., —O— group). In some embodiments, $R_1$ has the formula alkylene-L-$R_{1-1}$ (i.e., Q-L-$R_{1-1}$) and the alkylene (Q) is optionally interrupted with one oxygen atom. In some embodiments, $R_1$ has the formula $C_{1-5}$alkylene-L-$R_{1-1}$ and the $C_{1-5}$alkylene is optionally interrupted with one —O— group. Alternatively, stated Q is preferably a $C_{1-5}$alkylene optionally interrupted with one —O— group. Examples of preferred Q groups include —(CH$_2$)$_2$—, —(CH$_2$)$_3$—, —(CH$_2$)$_4$—, —(CH$_2$)$_5$—, and —(CH$_2$)$_2$—O—(CH$_2$)$_2$—.

In some embodiments, L is a bond or a functional linking group selected from the group consisting of —NH—S(O)$_2$—, —NH—C(O)—, —NH—C(S)—, —NH—S(O)$_2$—NR$_3$—, —NH—C(O)—NR$_3$—, —NH—C(S)—NR$_3$—, —NH—C(O)—O—, —O—, —S—, and —S(O)$_2$—

In some embodiments, L is a bond or a functional linking group selected from the group consisting of —NH—C(O)—, —NH—S(O)$_2$—, and —NH—C(O)—N(R$_3$)—.

In some embodiments, when L is —NH—S(O)$_2$— and R$_A$ and R$_B$ join to form an unsubstituted benzene ring, R$_{1-1}$ is a linear or branched aliphatic group having greater than 16 carbon atoms, optionally including one or more unsaturated carbon-carbon bonds. In some embodiments, when L is —NH—S(O$_2$)—, and n is 0, R$_{1-1}$ is a linear or branched aliphatic group having at least 16 carbon atoms, optionally including one or more unsaturated carbon-carbon bonds.

In some embodiments, when L is —NH—C(O)— and R$_A$ and R$_B$ join to form an unsubstituted pyridine ring, R$_{1-1}$ is a linear or branched aliphatic group having greater than 11 carbon atoms, optionally including one or more unsaturated carbon-carbon bonds. In some embodiments, when L is —NH—C(O)—, and n is 0, R$_{1-1}$ is a linear or branched aliphatic group having at least 12 carbon atoms, optionally including one or more unsaturated carbon-carbon bonds.

In some embodiments, R$_{1-1}$ is a linear or branched aliphatic group having at least 11 carbon atoms (preferably, at least 12 carbon atoms), optionally including one or more unsaturated carbon-carbon bonds. In some embodiments, R$_{1-1}$ is a linear or branched aliphatic group having 11-20 carbon atoms (preferably, 12-20 carbon atoms), optionally including one or more unsaturated carbon-carbon bonds. In some embodiments, R$_{1-1}$ is a linear (i.e., straight chain) alkyl group having 11-20 carbon atoms (preferably, 12-20 carbon atoms).

Such R$_{1-1}$ substituents are desirable because they provide lipid-like characteristics to compounds of the present invention. This is advantageous because these lipid moieties can aid in the sequestering of IRM's at the site of application. That is, the lipid moiety can assist in preventing the rapid diffusion of an IRM away from the site of administration. This sequestering can result in enhanced adjuvancy of an IRM, which could be manifest by enhanced recruitment and activation of antigen-presenting cells at a desired site. Furthermore, this sequestering can result in less systemic distribution of an IRM, and the ability to use lesser amounts of IRM's.

In some embodiments, R$_A$ and R$_B$ are each independently selected from the group consisting of: hydrogen, halogen, alkyl, alkenyl, alkoxy, alkylthio, and —N(R$_3$)$_2$.

In some embodiments, when taken together, R$_A$ and R$_B$ form a fused aryl ring or heteroaryl ring containing one heteroatom or a fused 5- to 7-membered saturated ring, optionally containing one heteroatom, wherein the heteroatom is selected from the group consisting of N and S, and wherein the aryl, heteroaryl, or 5- to 7-membered saturated ring is unsubstituted or substituted by one or more non-interfering substituents. Preferably, the substituents are selected from the group consisting of: halogen, hydroxy, alkyl, alkenyl, haloalkyl, alkoxy, alkylthio, and —N(R$_3$)$_2$.

In some embodiments, when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups; or when taken together, R$_A$ and R$_B$ form a fused 5- to 7-membered saturated ring, optionally containing one heteroatom selected from the group consisting of N and S, and unsubstituted or substituted by one or more R groups.

In some embodiments, when taken together, R$_A$ and R$_B$ form a fused 5- to 7-membered saturated ring, optionally containing one heteroatom selected from the group consisting of N and S, and unsubstituted or substituted by one or more substituents selected from the group consisting of: halogen, hydroxy, alkyl, alkenyl, haloalkyl, alkoxy, alkylthio, and —N(R$_3$)$_2$.

In some embodiments, R$_A$ and R$_B$ form a fused aryl or heteroaryl ring.

In some embodiments, R$_A$ and R$_B$ form a fused 5- to 7-membered saturated ring.

In some embodiments, R$_A$ and R$_B$ form a fused benzene ring which is unsubstituted.

In some embodiments, R$_A$ and R$_B$ form a fused pyridine ring which is unsubstituted.

In some embodiments, R is selected from the group consisting of: halogen, hydroxy, alkyl, alkenyl, haloalkyl, alkoxy, alkylthio, and —N(R$_3$)$_2$. In some embodiments, R" and R$_2$ are selected from the group consisting of: hydrogen; alkyl; alkenyl; aryl; heteroaryl; heterocyclyl; alkylene-Y-alkyl; alkylene-Y-alkenyl; alkylene-Y-aryl; and alkyl or alkenyl substituted by one or more substituents selected from the group consisting of: —OH; halogen; —N(R$_4$)$_2$; —C(O)—C$_{1-10}$alkyl; —C(O)—O—C$_{1-10}$alkyl; —N$_3$; aryl; heteroaryl; heterocyclyl; —C(O)-aryl; and —C(O)-heteroaryl. Preferably, in such embodiments, Y is —O— or —S(O)$_{0-2}$—, and each R$_4$ is independently selected from the group consisting of hydrogen, C$_{1-10}$alkyl, and C$_{2-10}$alkenyl.

In some embodiments, R" and R$_2$ are selected from the group consisting of hydrogen, alkyl, and alkylene-O-alkyl.

In some embodiments, each R$_3$ is independently selected from the group consisting of hydrogen and alkyl.

In some embodiments, each R$_4$ is independently selected from the group consisting of hydrogen, C$_{1-10}$alkyl, and C$_{2-10}$alkenyl.

In some embodiments, Y is —O— or —S(O)$_{0-2}$—.

In some embodiments, n is 0 to 4. In some embodiments, n is 0 or 1. In some embodiments, n is 0.

Preparation of Compounds

Compounds of the invention can be prepared using synthetic methods that are known to be useful in the preparation of imidazoquinolines, tetrahydroimidazoquinolines, imidazopyridines, imidazonaphthyridines, and tetrahydroimidazonaphthyridines.

For example, compounds of the invention where L is —NH—C(O)— can be prepared from conventional fatty acids such as stearic acid, palmitic acid, and linoleic acid using the synthetic methods described in U.S. Pat. Nos. 6,451, 810; 6,545,016; 6,194,425; 6,660,747; and 6,664,265 and PCT Publication WO 03/103584.

Compounds of the invention where L is —NH—S(O)$_2$— can be prepared from sulfonyl chlorides of the formula R$_{1-1}$S(O)$_2$Cl using the synthetic methods described in U.S. Pat. Nos. 6,331,539; 6,525,064; 6,194,425; 6,677,347; 6,677,349; and 6,683,088 and PCT Publication WO 03/103584.

Compounds of the invention where L is —NH—C(O)—N(R$_3$)— or —NH—C(S)—N(R$_3$)— can be prepared from isocyanates or thioisocyantes of the formulas R$_{1-1}$C=N=O and R$_{1-1}$C=N=S respectively using the synthetic methods described in U.S. Pat. Nos. 6,541,485; 6,573,273; 6,656,938; 6,660,735; and 6,545,017 and PCT Publication WO 03/103584.

Compounds of the invention where L is a bond can be prepared from amines of formula R$_{1-1}$NH$_2$ using the synthetic methods described in U.S. Pat. Nos. 4,689,338; 4,929,624; 5,268,376; 5,389,640; 5,352,784; and 5,446,153.

Compounds of the invention where L is —S— or —S(O)$_2$— can be prepared from mercaptans of formula $R_{1-1}SH$ using the synthetic methods described in U.S. Pat. Nos. 6,664, 264 and 6,667,312.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" or "effective amount" means an amount of the compound sufficient to induce a therapeutic or prophylactic effect, such as cytokine induction, cytokine inhibition, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

The compounds of the invention have been shown to induce, and certain compounds of the invention may inhibit, the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal acquiring the disease so that administration of the compound may provide a prophylactic treatment.

In addition to the ability to induce the production of cytokines, compounds of the invention may affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds.

Other cytokines whose production may be inhibited by the administration of certain compounds according to the invention include tumor necrosis factor-α (TNF-α). Among other effects, inhibition of TNF-α production can provide prophylaxis or therapeutic treatment of diseases in animals in which TNF is mediated, making the compounds useful in the treatment of, for example, autoimmune diseases. Accordingly, the invention provides a method of inhibiting TNF-α biosynthesis in an animal comprising administering an effective amount of a compound or composition of the invention to the animal. The animal to which the compound or composition is administered for inhibition of TNF-α biosynthesis may have a disease as described infra, for example an autoimmune disease, and administration of the compound may provide therapeutic treatment. Alternatively, the compound may be administered to the animal prior to the animal aquiring the disease so that administration of the compound may provide a prophylactic treatment.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately, together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV), a coronavirus (e.g., SARS), a papovavirus, (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases, such as, for example, diseases resulting from infection by bacteria of, for example, the genus *Escherichia, Enterobacter, Salmonella, Staphylococci, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases, such as, for example, candidiasis, aspergillosis, histoplasmonsis, cryptococcal meningitis, or parasitic diseases, such as, for example, malaria, pneumocystis carnii pneomonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, aenal cell leukemia, Karposi's sarcoma, melanoma, renal cell carcinoma, leukemias, such as, for example, myelogeous leukemia, chronic lymphocytic leukemia, and multiple myeloma, non-Hodgkin's lymphoma, cutaneous T-cell lymphoma, B-cell lymphoma, hairy cell leukemia, and other cancers; and (e) $T_H2$-mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia areata, inhibition of keloid formation and other types of scarring, and enhancing wound healing, including chronic wounds.

IRMs identified herein also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; and the like, for use in connection with, for example, BCG, cholera, plague, typhoid, hepatitis A, hepatitis B, and hepatitis C, influenza A and influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

IRMs may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of Formula I, II, III, IV, V, VI, VII, or a combination thereof to the animal. An animal may also be vaccinated by administering an effective amount of a compound or salt of Formula I, II, III, IV, V, VI, VII, or a combination thereof to the animal as a vaccine adjuvant.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal.

An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In certain embodiments, there is provided a method of inducing cytokine biosynthesis in an animal comprising administering an effective amount of a compound or salt described herein to the animal. In another embodiment, there is provided a method of treating a viral disease in an animal comprising administering a therapeutically effective amount of a compound or salt described herein to the animal. In another embodiment, there is provided a method of treating a neoplastic disease in an animal comprising administering a therapeutically effective amount of a compound or salt described herein to the animal. In another embodiment, there is provided a method of vaccinating an animal comprising administering an effective amount of a compound or salt described herein to the animal as a vaccine adjuvant. In another embodiment, there is provided a method of vaccinating an animal comprising administering an effective amount of N-(2-{2-[4-amino-2-(2-methoxyethyl)-1H-imidazo[4,5-c]quinolin-1-yl]ethoxy}ethyl)hexadecanamide to the animal as a vaccine adjuvant. In another embodiment, there is provided a method of vaccinating an animal comprising administering an effective amount of N-(2-{2-[4-amino-2-(2-methoxyethyl)-1H-imidazo[4,5-c]quinolin-1-yl]ethoxy}ethyl)octadecanamide to the animal as a vaccine adjuvant. In another embodiment, there is provided a method of vaccinating an animal comprising administering an effective amount of N-(2-{2-[4-amino-2-(2-methoxyethyl)-1H-imidazo[4,5-c]quinolin-1-yl]ethoxy}ethyl)dodecanamide to the animal as a vaccine adjuvant. In another embodiment, there is provided a method of vaccinating an animal comprising administering an effective amount of N-(2-{2-[4-amino-2-(2-methoxyethyl)-1H-imidazo[4,5-c]quinolin-1-yl]ethoxy}ethyl)tetradecanamide to the animal as a vaccine adjuvant.

Objects and advantages of this invention are further illustrated by the following examples, but the particular materials and amounts thereof recited in these examples, as well as other conditions and details, should not be construed to unduly limit this invention.

EXAMPLES

Example 1

Preparation of N-(2-{2-[4-amino-2-(2-methoxyethyl)-1H-imidazo[4,5-c]quinolin-1-yl]ethoxy}ethyl)hexadecanamide

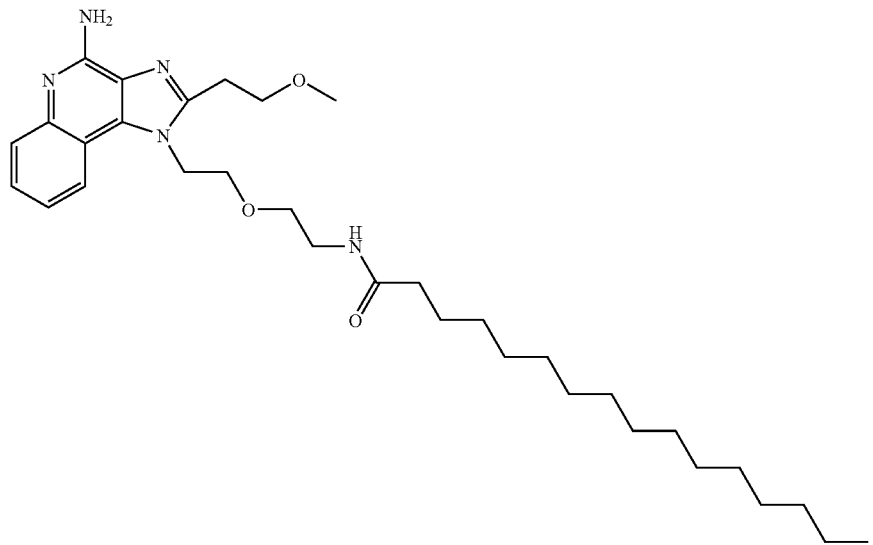

Part A

A solution of 2-(2-aminoethoxy)ethanol (29.0 g, 0.276 mol) in 180 mL of tetrahydrofuran (THF), under $N_2$, was cooled to 0° C. and treated with 140 mL of 2N NaOH solution. A solution of di-tert-butyl dicarbonate (60.2 g, 0.276 mol) in 180 mL of THF was then added dropwise over 1 h to the rapidly stirred solution. The reaction mixture was then allowed to warm to room temperature and was stirred an additional 18 hours. The THF was then removed under reduced pressure and the remaining aqueous slurry was brought to pH 3 by addition of 150 mL of 1M $H_2SO_4$ solution. This was then extracted with ethyl acetate (300 mL, 100 mL) and the combined organic layers were washed with $H_2O$ (2×) and brine. The organic portion was dried over $Na_2SO_4$ and concentrated to give tert-butyl 2-(2-hydroxyethoxy)ethylcarbamate as a colorless oil (47.1 g).

Part B

A rapidly stirred solution of tert-butyl 2-(2-hydroxyethoxy)ethylcarbamate (47.1 g, 0.230 mol) in 1 L of anhydrous $CH_2Cl_2$ was cooled to 0° C. under $N_2$ and treated with triethylamine (48.0 mL, 0.345 mol). Methanesulfonyl chloride (19.6 mL, 0.253 mol) was then added dropwise over 30 min. The reaction mixture was then allowed to warm to room temperature and was stirred an additional 22 hours. The reaction was quenched by addition of 500 mL saturated $NaHCO_3$ solution and the organic layer was separated. The organic phase was then washed with $H_2O$ (3×500 mL) and brine. The organic portion was dried over $Na_2SO_4$ and concentrated to give 2-{2-[(tert-butoxycarbonyl)amino]ethoxy}ethyl methanesulfonate as a brown oil (63.5 g).

Part C

A stirred solution of 2-{2-[(tert-butoxycarbonyl)amino]ethoxy}ethyl methanesulfonate (63.5 g, 0.224 mol) in 400 mL of N,N-dimethylformamide (DMF) was treated with $NaN_3$ (16.1 g, 0.247 mol) and the reaction mixture was heated to 90° C. under $N_2$. After 5 hours, the solution was cooled to room temperature and treated with 500 mL of cold $H_2O$. The reaction mixture was then extracted with $Et_2O$ (3×300 mL). The combined organic extracts were washed with $H_2O$ (4×100 mL) and brine (2×100 mL). The organic portion was dried over $MgSO_4$ and concentrated to give 52.0 g of tert-butyl 2-(2-azidoethoxy)ethylcarbamate as a light brown oil.

Part D

A solution of tert-butyl 2-(2-azidoethoxy)ethylcarbamate (47.0 g, 0.204 mol) in MeOH was treated with 4 g of 10% Pd on carbon and shaken under $H_2$ (3 Kg/cm$^2$) for 24 hours. The solution was then filtered through a CELITE pad and concentrated to give 35.3 g of crude tert-butyl 2-(2-aminoethoxy)ethylcarbamate as a colorless liquid that was used without further purification.

Part E

A stirred solution of 4-chloro-3-nitroquinoline (31.4 g, 0.151 mol) in 500 mL of anhydrous $CH_2Cl_2$, under $N_2$, was treated with triethylamine (43 mL, 0.308 mol) and tert-butyl 2-(2-aminoethoxy)ethylcarbamate (0.151 mol). After stirring overnight, the reaction mixture was washed with $H_2O$ (2×300 mL) and brine (300 mL). The organic portion was dried over $Na_2SO_4$ and concentrated to give a bright yellow solid. Recrystallization from ethyl acetate/hexanes gave 43.6 g of tert-butyl 2-{2-[(3-nitroquinolin-4-yl)amino]ethoxy}ethylcarbamate as bright yellow crystals.

Part F

A solution of tert-butyl 2-{2-[(3-nitroquinolin-4-yl)amino]ethoxy}ethylcarbamate (7.52 g, 20.0 mmol) in toluene was treated with 1.5 g of 5% Pt on carbon and shaken under $H_2$ (3 Kg/cm$^2$) for 24 hours. The solution was then filtered through a Celite pad and concentrated to give 6.92 g of crude tert-butyl 2-{2-[(3-aminoquinolin-4-yl)amino]ethoxy}ethylcarbamate as a yellow syrup.

Part G

A solution of tert-butyl 2-{2-[(3-aminoquinolin-4-yl)amino]ethoxy}ethylcarbamate (10.2 g, 29.5 mmol) in 250 mL of anhydrous $CH_2Cl_2$ was cooled to 0° C. and treated with triethylamine (4.18 mL, 30.0 mmol). Methoxypropionyl chloride (3.30 mL, 30.3 mmol) was then added dropwise over 5 min. The reaction was then warmed to room temperature and stirring was continued for 1 hour. The reaction mixture was then concentrated under reduced pressure to give an orange solid. This was dissolved in 250 mL of EtOH and 12.5 mL of triethylamine was added. The mixture was heated to reflux and stirred under $N_2$ overnight. The reaction was then concentrated to dryness under reduced pressure and treated with 300 mL of $Et_2O$. The mixture was then filtered and the filtrate was concentrated under reduced pressure to give a brown solid. The solid was dissolved in 200 mL of hot methanol and treated with activated charcoal. The hot solution was filtered and concentrated to give 11.1 g of tert-butyl 2-{2-[2-(2-methoxyethyl)-1H-imidazo[4,5-c]quinolin-1-yl]ethoxy}ethylcarbamate as a yellow syrup.

Part H

A solution of tert-butyl 2-{2-[2-(2-methoxyethyl)-1H-imidazo[4,5-c]quinolin-1-yl]ethoxy}ethylcarbamate (10.22 g, 24.7 mmol) in 250 mL of $CHCl_3$ was treated with 3-chloroperbenozic acid (77%, 9.12 g, 40.8 mmol). After stirring 30 minutes, the reaction mixture was washed with 1% $Na_2CO_3$ solution (2×75 mL) and brine. The organic layer was then dried over $Na_2SO_4$ and concentrated to give 10.6 g of tert-butyl 2-{2-[2-(2-methoxyethyl)-5-oxido-1H-imidazo[4,5-c]quinolin-1-yl]ethoxy}ethylcarbamate as an orange foam that was used without further purification.

Part I

A solution of tert-butyl 2-{2-[2-(2-methoxyethyl)-5-oxido-1H-imidazo[4,5-c]quinolin-1-yl]ethoxy}ethylcarbamate (10.6 g, 24.6 mmol) in 100 mL of 1,2-dichloroethane was heated to 60° C. and treated with 10 mL of concentrated $NH_4OH$ solution. To the rapidly stirred solution was added solid p-toluenesulfonyl chloride (7.05 g, 37.0 mmol) over a 10 minute period. The reaction mixture was treated with an additional 1 mL concentrated $NH_4OH$ solution and then sealed in a pressure vessel and heating was continued for 2 hours. The reaction mixture was then cooled and treated with 100 mL of $CHCl_3$. The reaction mixture was then washed with $H_{2O}$, 1% $Na_2CO_3$ solution (2×) and brine. The organic portion was dried over $Na_2SO_4$ and concentrated to give 10.6 g of tert-butyl 2-{2-[4-amino-2-(2-methoxyethyl)-1H-imidazo[4,5-c]quinolin-1-yl]ethoxy}ethylcarbamate as a brown foam.

Part J

Tert-butyl 2-{2-[4-amino-2-(2-methoxyethyl)-1H-imidazo[4,5-c]quinolin-1-yl]ethoxy}ethylcarbamate (10.6 g, 24.6 mmol) was treated with 75 mL of 2M HCl in ethanol and the mixture was heated to reflux with stirring. After 1.5 hours, the reaction mixture was cooled and filtered to give a gummy solid. The solid was washed with ethanol and $Et_2O$ and dried under vacuum to give the hydrochloride salt as a light brown solid. The free base was made by dissolving the hydrochloride salt in 50 mL of $H_2O$ and treating with 10% NaOH solution. The aqueous suspension was then concentrated to dryness and the residue was treated with $CHCl_3$. The resulting salts were removed by filtration and the filtrate was concentrated to give 3.82 g of 1-[2-(2-aminoethoxy)ethyl]-2-(2-methoxyethyl)-1H-imidazo[4,5-c]quinolin-4-amine as a tan powder.

MS 330 $(M+H)^+$;

$^1$H NMR (300 MHz, DMSO-$d_6$) δ 8.10 (d, J=8.1 Hz, 1H); 7.66 (d, J=8.2 Hz, 1H); 7.40 (m, 1H); 7.25 (m, 1H); 6.88 (br s, 2H); 4.78 (t, J=5.4 Hz, 2H); 3.89 (t, J=4.8 Hz, 2H); 3.84 (t, J=6.9 Hz, 2H); 3.54 (t, J=5.4 Hz, 2H); 3.31 (s, 3H); 3.23 (t, J=6.6 Hz, 2H); 2.88 (t, J=5.3 Hz, 2H).

Part K

Under a nitrogen atmosphere, a suspension of 1-[2-(2-aminoethoxy)ethyl]-2-(2-methoxyethyl)-1H-imidazo[4,5-c]quinolin-4-amine (140.5 mg, 0.428 mmol) in a mixture of dichloromethane (3.5 mL) and triethylamine (150 µL, 1.07 mmol) was cooled to 0° C. Palmitoyl chloride (130 µL, 0.428 mmol) was slowly added. The reaction mixture was allowed to stir at 0° C. for 2 hours at which time analysis by thin layer chromatography indicated that there was no starting material left. The reaction mixture was diluted with dichloromethane (30 mL), washed with saturated sodium bicarbonate solution (2×5 mL), dried over magnesium sulfate and then concentrated under reduced pressure. The resulting residue was purified by column chromatography (12 g of silica gel eluted with 2% methanol in dichloromethane) to provide 183 mg of N-(2-{2-[4-amino-2-(2-methoxyethyl)-1H-imidazo[4,5-c]quinolin-1-yl]ethoxy}ethyl)hexadecanamide as a white powder.

Anal. Calcd for $C_{33}H_{53}N_5O_3$: % C, 69.80; % H, 9.41; % N, 12.33. Found: % C, 69.60; % H, 9.28; % N, 11.99.

Example 2

Preparation of N-(2-{2-[4-amino-2-(2-methoxyethyl)-1H-imidazo[4,5-c]quinolin-1-yl]ethoxy}ethyl)octadecanamide

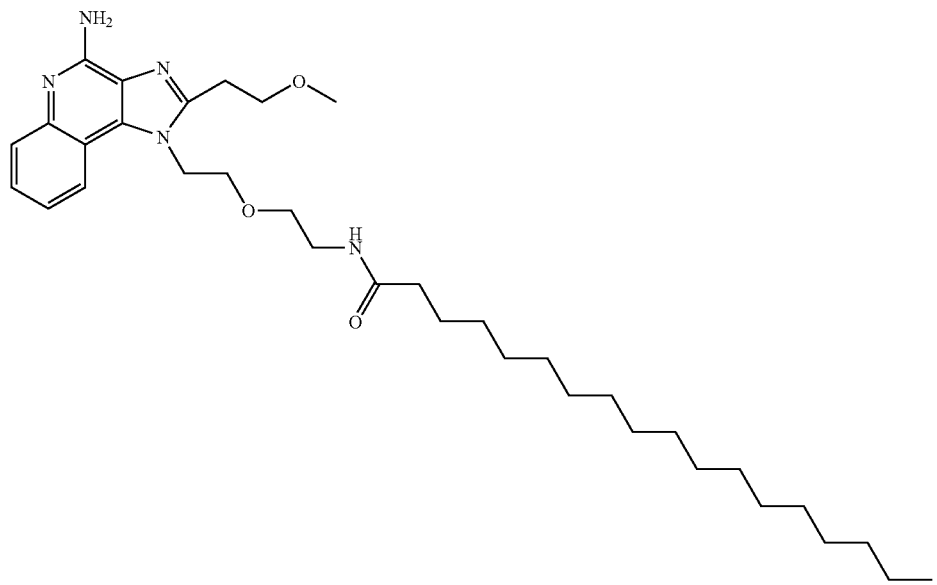

Under a nitrogen atmosphere, a mixture of 1-[2-(2-aminoethoxy)ethyl]-2-(2-methoxyethyl)-1H-imidazo[4,5-c]quinolin-4-amine (442.6 mg, 1.344 mmol) in a mixture of dichloromethane (20.0 mL) and triethylamine (468 μL, 3.56 mmol) was cooled to 0° C. Stearoyl chloride (454 μL, 1.34 mmol) was slowly added over a period of 10 minutes. The reaction mixture was allowed to stir at 0° C. for 1 hour at which time analysis by thin layer chromatography indicated that there was no starting material left. The reaction mixture was diluted with dichloromethane (50 mL), washed with saturated sodium bicarbonate solution (2×15 mL), dried over magnesium sulfate and then concentrated under reduced pressure. The residue was dried under high vacuum to provide 834 mg of crude product. The crude product was purified by column chromatography (20 g of silica gel eluted with 2% methanol in dichloromethane) to provide 596 mg of product. This material was recrystallized from ethyl acetate (1.2 mL) and then further purified by column chromatography (25 g of silica gel eluted sequentially with 300 mL of 1% CMA (80% chloroform/18% methanol/2% ammonium hydroxide) in chloroform, 500 mL of 2% CMA in chloroform, 500 mL of 3% CMA in chloroform, 500 mL of 4% CMA in chloroform, 750 mL of 5% CMA in chloroform, and 500 mL of 6% CMA in chloroform) to provide 23.8 mg of N-(2-{2-[4-amino-2-(2-methoxyethyl)-1H-imidazo[4,5-c]quinolin-1-yl]ethoxy}ethyl)octadecanamide as a white waxy solid, m.p. 80-83° C.

Anal. Calcd for $C_{35}H_{57}N_5O_3 \cdot 0.694\% H_2O$: % C, 70.06; % H, 9.65; % N, 11.67. Found: % C, 70.60; % H, 9.91; % N, 11.46.

Example 3

Preparation of N-(2-{2-[4-amino-2-(2-methoxyethyl)-1H-imidazo[4,5-c]quinolin-1-yl]ethoxy}ethyl) dodecanamide

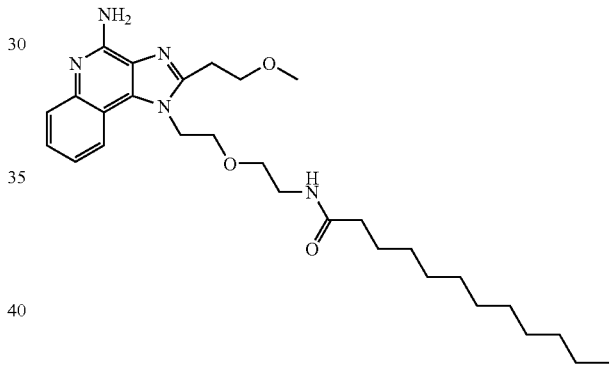

Under a nitrogen atmosphere, a mixture of 1-[2-(2-aminoethoxy)ethyl]-2-(2-methoxyethyl)-1H-imidazo[4,5-c]quinolin-4-amine (527.0 mg, 1.600 mmol) in a mixture of dichloromethane (20.0 mL) and triethylamine (551 μL, 4.00 mmol) was cooled to 0° C. Lauroyl chloride (370 mL, 1.60 mmol) was slowly added over a period of 10 minutes. The reaction mixture was allowed to stir at 0° C. for 1 hour at which time analysis by thin layer chromatography indicated that there was no starting material left. The reaction mixture was diluted with dichloromethane (50 mL), washed with saturated sodium bicarbonate solution (2×15 mL), dried over magnesium sulfate and then concentrated under reduced pressure. The residue was dried under high vacuum to provide 821 mg of crude product. The crude product was purified by column chromatography (20 g of silica gel eluted with 2% methanol in dichloromethane) to provide 527 mg of product. This material was recrystallized from ethyl acetate (1.2 mL) and then further purified by column chromatography (25 g of silica gel eluted sequentially with 300 mL of 1% CMA in chloroform, 500 mL of 2% CMA in chloroform, 500 mL of 3% CMA in chloroform, 500 mL of 4% CMA in chloroform, 750 mL of 5% CMA in chloroform, 750 mL of 6% CMA in chloroform, 500 mL 100% CMA) to provide 22.4 mg of N-(2-{2-[4- amino-2-(2-methoxyethyl)-1H-imidazo[4,5-c]quinolin-1-yl]ethoxy}ethyl)dodecanamide as a white waxy solid, m.p. 80-83° C.

Anal. Calcd for $C_{29}H_{45}N_5O_3 \cdot 1.66\%$ $H_2O$: % C, 66.94; % H, 8.90; % N, 13.46. Found: % C, 66.94; % H, 9.37; % N, 13.28.

Example 4

Preparation of N-(2-{2-[4-amino-2-(2-methoxyethyl)-1H-imidazo[4,5-c]quinolin-1-yl]ethoxy}ethyl)tetradecanamide

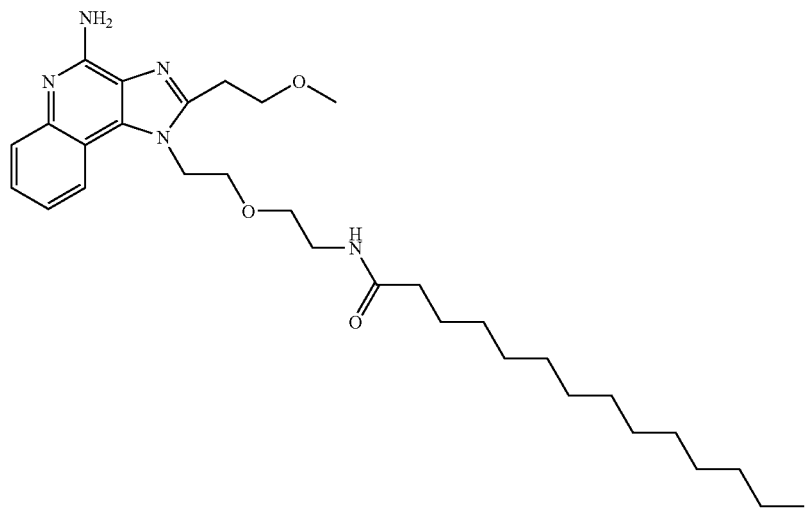

Under a nitrogen atmosphere, a mixture of 1-[2-(2-aminoethoxy)ethyl]-2-(2-methoxyethyl)-1H-imidazo[4,5-c]quinolin-4-amine (444.5 mg, 1.349 mmol) in a mixture of dichloromethane (20.0 mL) and triethylamine (470 μL, 3.37 mmol) was cooled to 0° C. Myristoyl chloride (367 μL, 1.35 mmol) was slowly added over a period of 10 minutes. The reaction mixture was allowed to stir at 0° C. for 1 hour at which time analysis by thin layer chromatography indicated that there was no starting material left. The reaction mixture was diluted with dichloromethane (50 mL), washed with saturated sodium bicarbonate solution (2×15 mL), dried over magnesium sulfate and then concentrated under reduced pressure. The crude product was purified by column chromatography (20 g of silica gel eluted with 2% methanol in dichloromethane) followed by recrystallization from ethyl acetate (1.2 mL) and then further purified by column chromatography (25 g of silica gel eluted sequentially with 300 mL of 1% CMA in chloroform, 500 mL of 2% CMA in chloroform, 500 mL of 3% CMA in chloroform, 500 mL of 4% CMA in chloroform, 750 mL of 5% CMA in chloroform, and 600 mL of 6% CMA in chloroform) to provide 9.5 mg of N-(2-{2-[4-amino-2-(2-methoxyethyl)-1H-imidazo[4,5-c]quinolin-1-yl]ethoxy}ethyl)tetradecanamide as a white waxy solid, m.p. 85-87° C.

Other Exemplary Compounds

Certain other exemplary compounds have the Formula (VII-X) and the following substituents, wherein each line of the table represents a specific compound of Formulas VIII, XI and/or X as indicated by the entry in the first column.

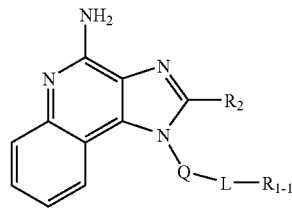

VIII

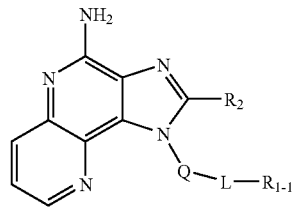

IX

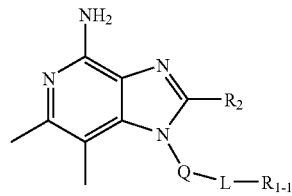

X

| Formulas | R$_{1-1}$ | R$_2$ | Q | L |
|---|---|---|---|---|
| VIII, IX, X | —(CH$_2$)$_{10}$CH$_3$ | H | —(CH$_2$)$_3$— | —NHC(O)— |
| VIII, IX, X | —(CH$_2$)$_{12}$CH$_3$ | H | —(CH$_2$)$_3$— | —NHC(O)— |
| VIII, IX, X | —(CH$_2$)$_{14}$CH$_3$ | H | —(CH$_2$)$_3$— | —NHC(O)— |
| VIII, IX, X | —(CH$_2$)$_{16}$CH$_3$ | H | —(CH$_2$)$_3$— | —NHC(O)— |
| VIII, IX, X | —(CH$_2$)$_{18}$CH$_3$ | H | —(CH$_2$)$_3$— | —NHC(O)— |
| VIII, IX, X | —(CH$_2$)$_7$CH═CH(CH$_2$)$_5$CH$_3$ | H | —(CH$_2$)$_3$— | —NHC(O)— |
| VIII, IX, X | —(CH$_2$)$_7$CH═CH(CH$_2$)$_7$CH$_3$ | H | —(CH$_2$)$_3$— | —NHC(O)— |
| VIII, IX, X | —(CH$_2$)$_6$(CH$_2$CH═CH)$_2$(CH$_2$)$_4$CH$_3$ | H | —(CH$_2$)$_3$— | —NHC(O)— |
| VIII, IX, X | —(CH$_2$)$_6$(CH$_2$CH═CH)$_3$CH$_2$CH$_3$ | H | —(CH$_2$)$_3$— | —NHC(O)— |
| VIII, IX, X | —(CH$_2$)$_2$(CH$_2$CH═CH)$_4$(CH$_2$)$_4$CH$_3$ | H | —(CH$_2$)$_3$— | —NHC(O)— |
| VIII, X | —(CH$_2$)$_{10}$CH$_3$ | —CH$_3$ | —(CH$_2$)$_3$— | —NHC(O)— |
| VIII, IX, X | —(CH$_2$)$_{12}$CH$_3$ | —CH$_3$ | —(CH$_2$)$_3$— | —NHC(O)— |
| VIII, IX, X | —(CH$_2$)$_{14}$CH$_3$ | —CH$_3$ | —(CH$_2$)$_3$— | —NHC(O)— |
| VIII, IX, X | —(CH$_2$)$_{16}$CH$_3$ | —CH$_3$ | —(CH$_2$)$_3$— | —NHC(O)— |
| VIII, IX, X | —(CH$_2$)$_{18}$CH$_3$ | —CH$_3$ | —(CH$_2$)$_3$— | —NHC(O)— |
| VIII, IX, X | —(CH$_2$)$_7$CH═CH(CH$_2$)$_5$CH$_3$ | —CH$_3$ | —(CH$_2$)$_3$— | —NHC(O)— |
| VIII, IX, X | —(CH$_2$)$_7$CH═CH(CH$_2$)$_7$CH$_3$ | —CH$_3$ | —(CH$_2$)$_3$— | —NHC(O)— |
| VIII, IX, X | —(CH$_2$)$_6$(CH$_2$CH═CH)$_2$(CH$_2$)$_4$CH$_3$ | —CH$_3$ | —(CH$_2$)$_3$— | —NHC(O)— |
| VIII, IX, X | —(CH$_2$)$_6$(CH$_2$CH═CH)$_3$CH$_2$CH$_3$ | —CH$_3$ | —(CH$_2$)$_3$— | —NHC(O)— |
| VIII, IX, X | —(CH$_2$)$_2$(CH$_2$CH═CH)$_4$(CH$_2$)$_4$CH$_3$ | —CH$_3$ | —(CH$_2$)$_3$— | —NHC(O)— |
| VIII, X | —(CH$_2$)$_{10}$CH$_3$ | —CH$_2$CH$_3$ | —(CH$_2$)$_3$— | —NHC(O)— |
| VIII, IX, X | —(CH$_2$)$_{12}$CH$_3$ | —CH$_2$CH$_3$ | —(CH$_2$)$_3$— | —NHC(O)— |
| VIII, IX, X | —(CH$_2$)$_{14}$CH$_3$ | —CH$_2$CH$_3$ | —(CH$_2$)$_3$— | —NHC(O)— |
| VIII, IX, X | —(CH$_2$)$_{16}$CH$_3$ | —CH$_2$CH$_3$ | —(CH$_2$)$_3$— | —NHC(O)— |
| VIII, IX, X | —(CH$_2$)$_{18}$CH$_3$ | —CH$_2$CH$_3$ | —(CH$_2$)$_3$— | —NHC(O)— |
| VIII, IX, X | —(CH$_2$)$_7$CH═CH(CH$_2$)$_5$CH$_3$ | —CH$_2$CH$_3$ | —(CH$_2$)$_3$— | —NHC(O)— |
| VIII, IX, X | —(CH$_2$)$_7$CH═CH(CH$_2$)$_7$CH$_3$ | —CH$_2$CH$_3$ | —(CH$_2$)$_3$— | —NHC(O)— |
| VIII, IX, X | —(CH$_2$)$_6$(CH$_2$CH═CH)$_2$(CH$_2$)$_4$CH$_3$ | —CH$_2$CH$_3$ | —(CH$_2$)$_3$— | —NHC(O)— |
| VIII, IX, X | —(CH$_2$)$_6$(CH$_2$CH═CH)$_3$CH$_2$CH$_3$ | —CH$_2$CH$_3$ | —(CH$_2$)$_3$— | —NHC(O)— |
| VIII, IX, X | —(CH$_2$)$_2$(CH$_2$CH═CH)$_4$(CH$_2$)$_4$CH$_3$ | —CH$_2$CH$_3$ | —(CH$_2$)$_3$— | —NHC(O)— |
| VIII, X | —(CH$_2$)$_{10}$CH$_3$ | —(CH$_2$)$_2$CH$_3$ | —(CH$_2$)$_3$— | —NHC(O)— |
| VIII, IX, X | —(CH$_2$)$_{12}$CH$_3$ | —(CH$_2$)$_2$CH$_3$ | —(CH$_2$)$_3$— | —NHC(O)— |
| VIII, IX, X | —(CH$_2$)$_{14}$CH$_3$ | —(CH$_2$)$_2$CH$_3$ | —(CH$_2$)$_3$— | —NHC(O)— |
| VIII, IX, X | —(CH$_2$)$_{16}$CH$_3$ | —(CH$_2$)$_2$CH$_3$ | —(CH$_2$)$_3$— | —NHC(O)— |
| VIII, IX, X | —(CH$_2$)$_{18}$CH$_3$ | —(CH$_2$)$_2$CH$_3$ | —(CH$_2$)$_3$— | —NHC(O)— |
| VIII, IX, X | —(CH$_2$)$_7$CH═CH(CH$_2$)$_5$CH$_3$ | —(CH$_2$)$_2$CH$_3$ | —(CH$_2$)$_3$— | —NHC(O)— |
| VIII, IX, X | —(CH$_2$)$_7$CH═CH(CH$_2$)$_7$CH$_3$ | —(CH$_2$)$_2$CH$_3$ | —(CH$_2$)$_3$— | —NHC(O)— |
| VIII, IX, X | —(CH$_2$)$_6$(CH$_2$CH═CH)$_2$(CH$_2$)$_4$CH$_3$ | —(CH$_2$)$_2$CH$_3$ | —(CH$_2$)$_3$— | —NHC(O)— |
| VIII, IX, X | —(CH$_2$)$_6$(CH$_2$CH═CH)$_3$CH$_2$CH$_3$ | —(CH$_2$)$_2$CH$_3$ | —(CH$_2$)$_3$— | —NHC(O)— |
| VIII, IX, X | —(CH$_2$)$_2$(CH$_2$CH═CH)$_4$(CH$_2$)$_4$CH$_3$ | —(CH$_2$)$_2$CH$_3$ | —(CH$_2$)$_3$— | —NHC(O)— |
| VIII, X | —(CH$_2$)$_{10}$CH$_3$ | —CH$_2$OCH$_2$CH$_3$ | —(CH$_2$)$_3$— | —NHC(O)— |

-continued

| | | | | |
|---|---|---|---|---|
| VIII, IX, X | —(CH$_2$)$_{12}$CH$_3$ | —CH$_2$OCH$_2$CH$_3$ | —(CH$_2$)$_3$— | —NHC(O)— |
| VIII, IX, X | —(CH$_2$)$_{14}$CH$_3$ | —CH$_2$OCH$_2$CH$_3$ | —(CH$_2$)$_3$— | —NHC(O)— |
| VIII, IX, X | —(CH$_2$)$_{16}$CH$_3$ | —CH$_2$OCH$_2$CH$_3$ | —(CH$_2$)$_3$— | —NHC(O)— |
| VIII, IX, X | —(CH$_2$)$_{18}$CH$_3$ | —CH$_2$OCH$_2$CH$_3$ | —(CH$_2$)$_3$— | —NHC(O)— |
| VIII, IX, X | —(CH$_2$)$_7$CH=CH(CH$_2$)$_5$CH$_3$ | —CH$_2$OCH$_2$CH$_3$ | —(CH$_2$)$_3$— | —NHC(O)— |
| VIII, IX, X | —(CH$_2$)$_7$CH=CH(CH$_2$)$_7$CH$_3$ | —CH$_2$OCH$_2$CH$_3$ | —(CH$_2$)$_3$— | —NHC(O)— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_3$— | —NHC(O)— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_3$— | —NHC(O)— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_3$— | —NHC(O)— |
| VIII, X | —(CH$_2$)$_{10}$CH$_3$ | —(CH$_2$)$_2$OCH$_3$ | —(CH$_2$)$_3$— | —NHC(O)— |
| VIII, IX, X | —(CH$_2$)$_{12}$CH$_3$ | —(CH$_2$)$_2$OCH$_3$ | —(CH$_2$)$_3$— | —NHC(O)— |
| VIII, IX, X | —(CH$_2$)$_{14}$CH$_3$ | —(CH$_2$)$_2$OCH$_3$ | —(CH$_2$)$_3$— | —NHC(O)— |
| VIII, IX, X | —(CH$_2$)$_{16}$CH$_3$ | —(CH$_2$)$_2$OCH$_3$ | —(CH$_2$)$_3$— | —NHC(O)— |
| VIII, IX, X | —(CH$_2$)$_{18}$CH$_3$ | —(CH$_2$)$_2$OCH$_3$ | —(CH$_2$)$_3$— | —NHC(O)— |
| VIII, IX, X | —(CH$_2$)$_7$CH=CH(CH$_2$)$_5$CH$_3$ | —(CH$_2$)$_2$OCH$_3$ | —(CH$_2$)$_3$— | —NHC(O)— |
| VIII, IX, X | —(CH$_2$)$_7$CH=CH(CH$_2$)$_7$CH$_3$ | —(CH$_2$)$_2$OCH$_3$ | —(CH$_2$)$_3$— | —NHC(O)— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_3$— | —NHC(O)— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_3$— | —NHC(O)— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_3$— | —NHC(O)— |
| VIII, X | —(CH$_2$)$_{10}$CH$_3$ | —(CH$_2$)$_3$CH$_3$ | —(CH$_2$)$_3$— | —NHC(O)— |
| VIII, IX, X | —(CH$_2$)$_{12}$CH$_3$ | —(CH$_2$)$_3$CH$_3$ | —(CH$_2$)$_3$— | —NHC(O)— |
| VIII, IX, X | —(CH$_2$)$_{14}$CH$_3$ | —(CH$_2$)$_3$CH$_3$ | —(CH$_2$)$_3$— | —NHC(O)— |
| VIII, IX, X | —(CH$_2$)$_{16}$CH$_3$ | —(CH$_2$)$_3$CH$_3$ | —(CH$_2$)$_3$— | —NHC(O)— |
| VIII, IX, X | —(CH$_2$)$_{18}$CH$_3$ | —(CH$_2$)$_3$CH$_3$ | —(CH$_2$)$_3$— | —NHC(O)— |
| VIII, IX, X | —(CH$_2$)$_7$CH=CH(CH$_2$)$_5$CH$_3$ | —(CH$_2$)$_3$CH$_3$ | —(CH$_2$)$_3$— | —NHC(O)— |
| VIII, IX, X | —(CH$_2$)$_7$CH=CH(CH$_2$)$_7$CH$_3$ | —(CH$_2$)$_3$CH$_3$ | —(CH$_2$)$_3$— | —NHC(O)— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_3$— | —NHC(O)— |
| VIII, IX, X | —(CH$_2$)$_6$(CH$_2$CH=CH)$_3$CH$_2$CH$_3$ | —(CH$_2$)$_3$CH$_3$ | —(CH$_2$)$_3$— | —NHC(O)— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_3$— | —NHC(O)— |
| VIII, X | —(CH$_2$)$_{10}$CH$_3$ | H | —(CH$_2$)$_4$— | —NHC(O)— |
| VIII, IX, X | —(CH$_2$)$_{12}$CH$_3$ | H | —(CH$_2$)$_4$— | —NHC(O)— |
| VIII, IX, X | —(CH$_2$)$_{14}$CH$_3$ | H | —(CH$_2$)$_4$— | —NHC(O)— |
| VIII, IX, X | —(CH$_2$)$_{16}$CH$_3$ | H | —(CH$_2$)$_4$— | —NHC(O)— |
| VIII, IX, X | —(CH$_2$)$_{18}$CH$_3$ | H | —(CH$_2$)$_4$— | —NHC(O)— |
| VIII, IX, X | —(CH$_2$)$_7$CH=CH(CH$_2$)$_5$CH$_3$ | H | —(CH$_2$)$_4$— | —NHC(O)— |
| VIII, IX, X | —(CH$_2$)$_7$CH=CH(CH$_2$)$_7$CH$_3$ | H | —(CH$_2$)$_4$— | —NHC(O)— |
| VIII, IX, X | —(CH$_2$)$_6$(CH$_2$CH=CH)$_2$(CH$_2$)$_4$CH$_3$ | H | —(CH$_2$)$_4$— | —NHC(O)— |
| VIII, IX, X | —(CH$_2$)$_6$(CH$_2$CH=CH)$_3$CH$_2$CH$_3$ | H | —(CH$_2$)$_4$— | —NHC(O)— |
| VIII, IX, X | —(CH$_2$)$_2$(CH$_2$CH=CH)$_4$(CH$_2$)$_4$CH$_3$ | H | —(CH$_2$)$_4$— | —NHC(O)— |
| VIII, X | —(CH$_2$)$_{10}$CH$_3$ | —CH$_3$ | —(CH$_2$)$_4$— | —NHC(O)— |
| VIII, IX, X | —(CH$_2$)$_{12}$CH$_3$ | —CH$_3$ | —(CH$_2$)$_4$— | —NHC(O)— |
| VIII, IX, X | —(CH$_2$)$_{14}$CH$_3$ | —CH$_3$ | —(CH$_2$)$_4$— | —NHC(O)— |
| VIII, IX, X | —(CH$_2$)$_{16}$CH$_3$ | —CH$_3$ | —(CH$_2$)$_4$— | —NHC(O)— |
| VIII, IX, X | —(CH$_2$)$_{18}$CH$_3$ | —CH$_3$ | —(CH$_2$)$_4$— | —NHC(O)— |
| VIII, IX, X | —(CH$_2$)$_7$CH=CH(CH$_2$)$_5$CH$_3$ | —CH$_3$ | —(CH$_2$)$_4$— | —NHC(O)— |
| VIII, IX, X | —(CH$_2$)$_7$CH=CH(CH$_2$)$_7$CH$_3$ | —CH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —CH$_3$ | —(CH$_2$)$_4$— | —NHC(O)— |
| VIII, IX, X | —(CH$_2$)$_6$(CH$_2$CH=CH)$_3$CH$_2$CH$_3$ | —CH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —CH$_3$ | —(CH$_2$)$_4$— | —NHC(O)— |
| VIII, X | —(CH$_2$)$_{10}$CH$_3$ | —CH$_2$CH$_3$ | —(CH$_2$)$_4$— | —NHC(O)— |
| VIII, IX, X | —(CH$_2$)$_{12}$CH$_3$ | —CH$_2$CH$_3$ | —(CH$_2$)$_4$— | —NHC(O)— |
| VIII, IX, X | —(CH$_2$)$_{14}$CH$_3$ | —CH$_2$CH$_3$ | —(CH$_2$)$_4$— | —NHC(O)— |
| VIII, IX, X | —(CH$_2$)$_{16}$CH$_3$ | —CH$_2$CH$_3$ | —(CH$_2$)$_4$— | —NHC(O)— |
| VIII, IX, X | —(CH$_2$)$_{18}$CH$_3$ | —CH$_2$CH$_3$ | —(CH$_2$)$_4$— | —NHC(O)— |
| VIII, IX, X | —(CH$_2$)$_7$CH=CH(CH$_2$)$_5$CH$_3$ | —CH$_2$CH$_3$ | —(CH$_2$)$_4$— | —NHC(O)— |
| VIII, IX, X | —(CH$_2$)$_7$CH=CH(CH$_2$)$_7$CH$_3$ | —CH$_2$CH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —CH$_2$CH$_3$ | —(CH$_2$)$_4$— | —NHC(O)— |
| VIII, IX, X | —(CH$_2$)$_6$(CH$_2$CH=CH)$_3$CH$_2$CH$_3$ | —CH$_2$CH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —CH$_2$CH$_3$ | —(CH$_2$)$_4$— | —NHC(O)— |
| VIII, X | —(CH$_2$)$_{10}$CH$_3$ | —(CH$_2$)$_2$CH$_3$ | —(CH$_2$)$_4$— | —NHC(O)— |
| VIII, IX, X | —(CH$_2$)$_{12}$CH$_3$ | —(CH$_2$)$_2$CH$_3$ | —(CH$_2$)$_4$— | —NHC(O)— |
| VIII, IX, X | —(CH$_2$)$_{14}$CH$_3$ | —(CH$_2$)$_2$CH$_3$ | —(CH$_2$)$_4$— | —NHC(O)— |
| VIII, IX, X | —(CH$_2$)$_{16}$CH$_3$ | —(CH$_2$)$_2$CH$_3$ | —(CH$_2$)$_4$— | —NHC(O)— |
| VIII, IX, X | —(CH$_2$)$_{18}$CH$_3$ | —(CH$_2$)$_2$CH$_3$ | —(CH$_2$)$_4$— | —NHC(O)— |
| VIII, IX, X | —(CH$_2$)$_7$CH=CH(CH$_2$)$_5$CH$_3$ | —(CH$_2$)$_2$CH$_3$ | —(CH$_2$)$_4$— | —NHC(O)— |
| VIII, IX, X | —(CH$_2$)$_7$CH=CH(CH$_2$)$_7$CH$_3$ | —(CH$_2$)$_2$CH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_4$— | —NHC(O)— |
| VIII, IX, X | —(CH$_2$)$_6$(CH$_2$CH=CH)$_3$CH$_2$CH$_3$ | —(CH$_2$)$_2$CH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_4$— | —NHC(O)— |
| VIII, X | —(CH$_2$)$_{10}$CH$_3$ | —CH$_2$OCH$_2$CH$_3$ | —(CH$_2$)$_4$— | —NHC(O)— |
| VIII, IX, X | —(CH$_2$)$_{12}$CH$_3$ | —CH$_2$OCH$_2$CH$_3$ | —(CH$_2$)$_4$— | —NHC(O)— |
| VIII, IX, X | —(CH$_2$)$_{14}$CH$_3$ | —CH$_2$OCH$_2$CH$_3$ | —(CH$_2$)$_4$— | —NHC(O)— |
| VIII, IX, X | —(CH$_2$)$_{16}$CH$_3$ | —CH$_2$OCH$_2$CH$_3$ | —(CH$_2$)$_4$— | —NHC(O)— |
| VIII, IX, X | —(CH$_2$)$_{18}$CH$_3$ | —CH$_2$OCH$_2$CH$_3$ | —(CH$_2$)$_4$— | —NHC(O)— |
| VIII, IX, X | —(CH$_2$)$_7$CH=CH(CH$_2$)$_5$CH$_3$ | —CH$_2$OCH$_2$CH$_3$ | —(CH$_2$)$_4$— | —NHC(O)— |
| VIII, IX, X | —(CH$_2$)$_7$CH=CH(CH$_2$)$_7$CH$_3$ | —CH$_2$OCH$_2$CH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_4$— | —NHC(O)— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_4$— | —NHC(O)— |

-continued

| | | | | |
|---|---|---|---|---|
| VIII, X | —(CH$_2$)$_{10}$CH$_3$ | —(CH$_2$)$_2$OCH$_3$ | —(CH$_2$)$_4$— | —NHC(O)— |
| VIII, IX, X | —(CH$_2$)$_{12}$CH$_3$ | —(CH$_2$)$_2$OCH$_3$ | —(CH$_2$)$_4$— | —NHC(O)— |
| VIII, IX, X | —(CH$_2$)$_{14}$CH$_3$ | —(CH$_2$)$_2$OCH$_3$ | —(CH$_2$)$_4$— | —NHC(O)— |
| VIII, IX, X | —(CH$_2$)$_{16}$CH$_3$ | —(CH$_2$)$_2$OCH$_3$ | —(CH$_2$)$_4$— | —NHC(O)— |
| VIII, IX, X | —(CH$_2$)$_{18}$CH$_3$ | —(CH$_2$)$_2$OCH$_3$ | —(CH$_2$)$_4$— | —NHC(O)— |
| VIII, IX, X | —(CH$_2$)$_7$CH=CH(CH$_2$)$_5$CH$_3$ | —(CH$_2$)$_2$OCH$_3$ | —(CH$_2$)$_4$— | —NHC(O)— |
| VIII, IX, X | —(CH$_2$)$_7$CH=CH(CH$_2$)$_7$CH$_3$ | —(CH$_2$)$_2$OCH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_4$— | —NHC(O)— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_4$— | —NHC(O)— |
| VIII, X | —(CH$_2$)$_{10}$CH$_3$ | —(CH$_2$)$_3$CH$_3$ | —(CH$_2$)$_4$— | —NHC(O)— |
| VIII, IX, X | —(CH$_2$)$_{12}$CH$_3$ | —(CH$_2$)$_3$CH$_3$ | —(CH$_2$)$_4$— | —NHC(O)— |
| VIII, IX, X | —(CH$_2$)$_{14}$CH$_3$ | —(CH$_2$)$_3$CH$_3$ | —(CH$_2$)$_4$— | —NHC(O)— |
| VIII, IX, X | —(CH$_2$)$_{16}$CH$_3$ | —(CH$_2$)$_3$CH$_3$ | —(CH$_2$)$_4$— | —NHC(O)— |
| VIII, IX, X | —(CH$_2$)$_{18}$CH$_3$ | —(CH$_2$)$_3$CH$_3$ | —(CH$_2$)$_4$— | —NHC(O)— |
| VIII, IX, X | —(CH$_2$)$_7$CH=CH(CH$_2$)$_5$CH$_3$ | —(CH$_2$)$_3$CH$_3$ | —(CH$_2$)$_4$— | —NHC(O)— |
| VIII, IX, X | —(CH$_2$)$_7$CH=CH(CH$_2$)$_7$CH$_3$ | —(CH$_2$)$_3$CH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_4$— | —NHC(O)— |
| VIII, IX, X | —(CH$_2$)$_6$(CH$_2$CH=CH)$_3$CH$_2$CH$_3$ | —(CH$_2$)$_3$CH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_4$— | —NHC(O)— |
| VIII, X | —(CH$_2$)$_{10}$CH$_3$ | H | —(CH$_2$)$_5$— | —NHC(O)— |
| VIII, IX, X | —(CH$_2$)$_{12}$CH$_3$ | H | —(CH$_2$)$_5$— | —NHC(O)— |
| VIII, IX, X | —(CH$_2$)$_{14}$CH$_3$ | H | —(CH$_2$)$_5$— | —NHC(O)— |
| VIII, IX, X | —(CH$_2$)$_{16}$CH$_3$ | H | —(CH$_2$)$_5$— | —NHC(O)— |
| VIII, IX, X | —(CH$_2$)$_{18}$CH$_3$ | H | —(CH$_2$)$_5$— | —NHC(O)— |
| VIII, IX, X | —(CH$_2$)$_7$CH=CH(CH$_2$)$_5$CH$_3$ | H | —(CH$_2$)$_5$— | —NHC(O)— |
| VIII, IX, X | —(CH$_2$)$_7$CH=CH(CH$_2$)$_7$CH$_3$ | H | —(CH$_2$)$_5$— | —NHC(O)— |
| VIII, IX, X | —(CH$_2$)$_6$(CH$_2$CH=CH)$_2$(CH$_2$)$_4$CH$_3$ | H | —(CH$_2$)$_5$— | —NHC(O)— |
| VIII, IX, X | —(CH$_2$)$_6$(CH$_2$CH=CH)$_3$CH$_2$CH$_3$ | H | —(CH$_2$)$_5$— | —NHC(O)— |
| VIII, IX, X | —(CH$_2$)$_2$(CH$_2$CH=CH)$_4$(CH$_2$)$_4$CH$_3$ | H | —(CH$_2$)$_5$— | —NHC(O)— |
| VIII, X | —(CH$_2$)$_{10}$CH$_3$ | —CH$_3$ | —(CH$_2$)$_5$— | —NHC(O)— |
| VIII, IX, X | —(CH$_2$)$_{12}$CH$_3$ | —CH$_3$ | —(CH$_2$)$_5$— | —NHC(O)— |
| VIII, IX, X | —(CH$_2$)$_{14}$CH$_3$ | —CH$_3$ | —(CH$_2$)$_5$— | —NHC(O)— |
| VIII, IX, X | —(CH$_2$)$_{16}$CH$_3$ | —CH$_3$ | —(CH$_2$)$_5$— | —NHC(O)— |
| VIII, IX, X | —(CH$_2$)$_{18}$CH$_3$ | —CH$_3$ | —(CH$_2$)$_5$— | —NHC(O)— |
| VIII, IX, X | —(CH$_2$)$_7$CH=CH(CH$_2$)$_5$CH$_3$ | —CH$_3$ | —(CH$_2$)$_5$— | —NHC(O)— |
| VIII, IX, X | —(CH$_2$)$_7$CH=CH(CH$_2$)$_7$CH$_3$ | —CH$_3$ | —(CH$_2$)$_5$— | —NHC(O)— |
| VIII, IX, X | —(CH$_2$)$_6$(CH$_2$CH=CH)$_2$(CH$_2$)$_4$CH$_3$ | —CH$_3$ | —(CH$_2$)$_5$— | —NHC(O)— |
| VIII, IX, X | —(CH$_2$)$_6$(CH$_2$CH=CH)$_3$CH$_2$CH$_3$ | —CH$_3$ | —(CH$_2$)$_5$— | —NHC(O)— |
| VIII, IX, X | —(CH$_2$)$_2$(CH$_2$CH=CH)$_4$(CH$_2$)$_4$CH$_3$ | —CH$_3$ | —(CH$_2$)$_5$— | —NHC(O)— |
| VIII, X | —(CH$_2$)$_{10}$CH$_3$ | —CH$_2$CH$_3$ | —(CH$_2$)$_5$— | —NHC(O)— |
| VIII, IX, X | —(CH$_2$)$_{12}$CH$_3$ | —CH$_2$CH$_3$ | —(CH$_2$)$_5$— | —NHC(O)— |
| VIII, IX, X | —(CH$_2$)$_{14}$CH$_3$ | —CH$_2$CH$_3$ | —(CH$_2$)$_5$— | —NHC(O)— |
| VIII, IX, X | —(CH$_2$)$_{16}$CH$_3$ | —CH$_2$CH$_3$ | —(CH$_2$)$_5$— | —NHC(O)— |
| VIII, IX, X | —(CH$_2$)$_{18}$CH$_3$ | —CH$_2$CH$_3$ | —(CH$_2$)$_5$— | —NHC(O)— |
| VIII, IX, X | —(CH$_2$)$_7$CH=CH(CH$_2$)$_5$CH$_3$ | —CH$_2$CH$_3$ | —(CH$_2$)$_5$— | —NHC(O)— |
| VIII, IX, X | —(CH$_2$)$_7$CH=CH(CH$_2$)$_7$CH$_3$ | —CH$_2$CH$_3$ | —(CH$_2$)$_5$— | —NHC(O)— |
| VIII, IX, X | —(CH$_2$)$_6$(CH$_2$CH=CH)$_2$(CH$_2$)$_4$CH$_3$ | —CH$_2$CH$_3$ | —(CH$_2$)$_5$— | —NHC(O)— |
| VIII, IX, X | —(CH$_2$)$_6$(CH$_2$CH=CH)$_3$CH$_2$CH$_3$ | —CH$_2$CH$_3$ | —(CH$_2$)$_5$— | —NHC(O)— |
| VIII, IX, X | —(CH$_2$)$_2$(CH$_2$CH=CH)$_4$(CH$_2$)$_4$CH$_3$ | —CH$_2$CH$_3$ | —(CH$_2$)$_5$— | —NHC(O)— |
| VIII, X | —(CH$_2$)$_{10}$CH$_3$ | —(CH$_2$)$_2$CH$_3$ | —(CH$_2$)$_5$— | —NHC(O)— |
| VIII, IX, X | —(CH$_2$)$_{12}$CH$_3$ | —(CH$_2$)$_2$CH$_3$ | —(CH$_2$)$_5$— | —NHC(O)— |
| VIII, IX, X | —(CH$_2$)$_{14}$CH$_3$ | —(CH$_2$)$_2$CH$_3$ | —(CH$_2$)$_5$— | —NHC(O)— |
| VIII, IX, X | —(CH$_2$)$_{16}$CH$_3$ | —(CH$_2$)$_2$CH$_3$ | —(CH$_2$)$_5$— | —NHC(O)— |
| VIII, IX, X | —(CH$_2$)$_{18}$CH$_3$ | —(CH$_2$)$_2$CH$_3$ | —(CH$_2$)$_5$— | —NHC(O)— |
| VIII, IX, X | —(CH$_2$)$_7$CH=CH(CH$_2$)$_5$CH$_3$ | —(CH$_2$)$_2$CH$_3$ | —(CH$_2$)$_5$— | —NHC(O)— |
| VIII, IX, X | —(CH$_2$)$_7$CH=CH(CH$_2$)$_7$CH$_3$ | —(CH$_2$)$_2$CH$_3$ | —(CH$_2$)$_5$— | —NHC(O)— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_5$— | —NHC(O)— |
| VIII, IX, X | —(CH$_2$)$_6$(CH$_2$CH=CH)$_3$CH$_2$CH$_3$ | —(CH$_2$)$_2$CH$_3$ | —(CH$_2$)$_5$— | —NHC(O)— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_5$— | —NHC(O)— |
| VIII, X | —(CH$_2$)$_{10}$CH$_3$ | —CH$_2$OCH$_2$CH$_3$ | —(CH$_2$)$_5$— | —NHC(O)— |
| VIII, IX, X | —(CH$_2$)$_{12}$CH$_3$ | —CH$_2$OCH$_2$CH$_3$ | —(CH$_2$)$_5$— | —NHC(O)— |
| VIII, IX, X | —(CH$_2$)$_{14}$CH$_3$ | —CH$_2$OCH$_2$CH$_3$ | —(CH$_2$)$_5$— | —NHC(O)— |
| VIII, IX, X | —(CH$_2$)$_{16}$CH$_3$ | —CH$_2$OCH$_2$CH$_3$ | —(CH$_2$)$_5$— | —NHC(O)— |
| VIII, IX, X | —(CH$_2$)$_{18}$CH$_3$ | —CH$_2$OCH$_2$CH$_3$ | —(CH$_2$)$_5$— | —NHC(O)— |
| VIII, IX, X | —(CH$_2$)$_7$CH=CH(CH$_2$)$_5$CH$_3$ | —CH$_2$OCH$_2$CH$_3$ | —(CH$_2$)$_5$— | —NHC(O)— |
| VIII, IX, X | —(CH$_2$)$_7$CH=CH(CH$_2$)$_7$CH$_3$ | —CH$_2$OCH$_2$CH$_3$ | —(CH$_2$)$_5$— | —NHC(O)— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_5$— | —NHC(O)— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_5$— | —NHC(O)— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_5$— | —NHC(O)— |
| VIII, X | —(CH$_2$)$_{10}$CH$_3$ | —(CH$_2$)$_2$OCH$_3$ | —(CH$_2$)$_5$— | —NHC(O)— |
| VIII, IX, X | —(CH$_2$)$_{12}$CH$_3$ | —(CH$_2$)$_2$OCH$_3$ | —(CH$_2$)$_5$— | —NHC(O)— |
| VIII, IX, X | —(CH$_2$)$_{14}$CH$_3$ | —(CH$_2$)$_2$OCH$_3$ | —(CH$_2$)$_5$— | —NHC(O)— |
| VIII, IX, X | —(CH$_2$)$_{16}$CH$_3$ | —(CH$_2$)$_2$OCH$_3$ | —(CH$_2$)$_5$— | —NHC(O)— |
| VIII, IX, X | —(CH$_2$)$_{18}$CH$_3$ | —(CH$_2$)$_2$OCH$_3$ | —(CH$_2$)$_5$— | —NHC(O)— |
| VIII, IX, X | —(CH$_2$)$_7$CH=CH(CH$_2$)$_5$CH$_3$ | —(CH$_2$)$_2$OCH$_3$ | —(CH$_2$)$_5$— | —NHC(O)— |
| VIII, IX, X | —(CH$_2$)$_7$CH=CH(CH$_2$)$_7$CH$_3$ | —(CH$_2$)$_2$OCH$_3$ | —(CH$_2$)$_5$— | —NHC(O)— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_4$— | —NHC(O)— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_4$— | —NHC(O)— |

-continued

| | | | | |
|---|---|---|---|---|
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_4$— | —NHC(O)— |
| VIII, X | —(CH$_2$)$_{10}$CH$_3$ | —(CH$_2$)$_3$CH$_3$ | —(CH$_2$)$_5$— | —NHC(O)— |
| VIII, IX, X | —(CH$_2$)$_{12}$CH$_3$ | —(CH$_2$)$_3$CH$_3$ | —(CH$_2$)$_5$— | —NHC(O)— |
| VIII, IX, X | —(CH$_2$)$_{14}$CH$_3$ | —(CH$_2$)$_3$CH$_3$ | —(CH$_2$)$_5$— | —NHC(O)— |
| VIII, IX, X | —(CH$_2$)$_{16}$CH$_3$ | —(CH$_2$)$_3$CH$_3$ | —(CH$_2$)$_5$— | —NHC(O)— |
| VIII, IX, X | —(CH$_2$)$_{18}$CH$_3$ | —(CH$_2$)$_3$CH$_3$ | —(CH$_2$)$_5$— | —NHC(O)— |
| VIII, IX, X | —(CH$_2$)$_7$CH=CH(CH$_2$)$_5$CH$_3$ | —(CH$_2$)$_3$CH$_3$ | —(CH$_2$)$_5$— | —NHC(O)— |
| VIII, IX, X | —(CH$_2$)$_7$CH=CH(CH$_2$)$_7$CH$_3$ | —(CH$_2$)$_3$CH$_3$ | —(CH$_2$)$_5$— | —NHC(O)— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_5$— | —NHC(O)— |
| VIII, IX, X | —(CH$_2$)$_6$(CH$_2$CH=CH)$_3$CH$_2$CH$_3$ | —(CH$_2$)$_3$CH$_3$ | —(CH$_2$)$_5$— | —NHC(O)— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_5$— | —NHC(O)— |
| VIII, X | —(CH$_2$)$_{10}$CH$_3$ | H | —(CH$_2$)$_2$O(CH$_2$)$_2$— | —NHC(O)— |
| VIII, IX, X | —(CH$_2$)$_{12}$CH$_3$ | H | —(CH$_2$)$_2$O(CH$_2$)$_2$— | —NHC(O)— |
| VIII, IX, X | —(CH$_2$)$_{14}$CH$_3$ | H | —(CH$_2$)$_2$O(CH$_2$)$_2$— | —NHC(O)— |
| VIII, IX, X | —(CH$_2$)$_{16}$CH$_3$ | H | —(CH$_2$)$_2$O(CH$_2$)$_2$— | —NHC(O)— |
| VIII, IX, X | —(CH$_2$)$_{18}$CH$_3$ | H | —(CH$_2$)$_2$O(CH$_2$)$_2$— | —NHC(O)— |
| VIII, IX, X | —(CH$_2$)$_7$CH=CH(CH$_2$)$_5$CH$_3$ | H | —(CH$_2$)$_2$O(CH$_2$)$_2$— | —NHC(O)— |
| VIII, IX, X | —(CH$_2$)$_7$CH=CH(CH$_2$)$_7$CH$_3$ | H | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | H | —(CH$_2$)$_2$O(CH$_2$)$_2$— | —NHC(O)— |
| VIII, IX, X | —(CH$_2$)$_6$(CH$_2$CH=CH)$_3$CH$_2$CH$_3$ | H | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | H | —(CH$_2$)$_2$O(CH$_2$)$_2$— | —NHC(O)— |
| VIII, X | —(CH$_2$)$_{10}$CH$_3$ | —CH$_3$ | —(CH$_2$)$_2$O(CH$_2$)$_2$— | —NHC(O)— |
| VIII, IX, X | —(CH$_2$)$_{12}$CH$_3$ | —CH$_3$ | —(CH$_2$)$_2$O(CH$_2$)$_2$— | —NHC(O)— |
| VIII, IX, X | —(CH$_2$)$_{14}$CH$_3$ | —CH$_3$ | —(CH$_2$)$_2$O(CH$_2$)$_2$— | —NHC(O)— |
| VIII, IX, X | —(CH$_2$)$_{16}$CH$_3$ | —CH$_3$ | —(CH$_2$)$_2$O(CH$_2$)$_2$— | —NHC(O)— |
| VIII, IX, X | —(CH$_2$)$_{18}$CH$_3$ | —CH$_3$ | —(CH$_2$)$_2$O(CH$_2$)$_2$— | —NHC(O)— |
| VIII, IX, X | —(CH$_2$)$_7$CH=CH(CH$_2$)$_5$CH$_3$ | —CH$_3$ | —(CH$_2$)$_2$O(CH$_2$)$_2$— | —NHC(O)— |
| VIII, IX, X | —(CH$_2$)$_7$CH=CH(CH$_2$)$_7$CH$_3$ | —CH$_3$ | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | —CH$_3$ | —(CH$_2$)$_2$O(CH$_2$)$_2$— | —NHC(O)— |
| VIII, IX, X | —(CH$_2$)$_6$(CH$_2$CH=CH)$_3$CH$_2$CH$_3$ | —CH$_3$ | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | —CH$_3$ | —(CH$_2$)$_2$O(CH$_2$)$_2$— | —NHC(O)— |
| VIII, X | —(CH$_2$)$_{10}$CH$_3$ | —CH$_2$CH$_3$ | —(CH$_2$)$_2$O(CH$_2$)$_2$— | —NHC(O)— |
| VIII, IX, X | —(CH$_2$)$_{12}$CH$_3$ | —CH$_2$CH$_3$ | —(CH$_2$)$_2$O(CH$_2$)$_2$— | —NHC(O)— |
| VIII, IX, X | —(CH$_2$)$_{14}$CH$_3$ | —CH$_2$CH$_3$ | —(CH$_2$)$_2$O(CH$_2$)$_2$— | —NHC(O)— |
| VIII, IX, X | —(CH$_2$)$_{16}$CH$_3$ | —CH$_2$CH$_3$ | —(CH$_2$)$_2$O(CH$_2$)$_2$— | —NHC(O)— |
| VIII, IX, X | —(CH$_2$)$_{18}$CH$_3$ | —CH$_2$CH$_3$ | —(CH$_2$)$_2$O(CH$_2$)$_2$— | —NHC(O)— |
| VIII, IX, X | —(CH$_2$)$_7$CH=CH(CH$_2$)$_5$CH$_3$ | —CH$_2$CH$_3$ | —(CH$_2$)$_2$O(CH$_2$)$_2$— | —NHC(O)— |
| VIII, IX, X | —(CH$_2$)$_7$CH=CH(CH$_2$)$_7$CH$_3$ | —CH$_2$CH$_3$ | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | —CH$_2$CH$_3$ | —(CH$_2$)$_2$O(CH$_2$)$_2$— | —NHC(O)— |
| VIII, IX, X | —(CH$_2$)$_6$(CH$_2$CH=CH)$_3$CH$_2$CH$_3$ | —CH$_2$CH$_3$ | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | —CH$_2$CH$_3$ | —(CH$_2$)$_2$O(CH$_2$)$_2$— | —NHC(O)— |
| VIII, X | —(CH$_2$)$_{10}$CH$_3$ | —(CH$_2$)$_2$CH$_3$ | —(CH$_2$)$_2$O(CH$_2$)$_2$— | —NHC(O)— |
| VIII, IX, X | —(CH$_2$)$_{12}$CH$_3$ | —(CH$_2$)$_2$CH$_3$ | —(CH$_2$)$_2$O(CH$_2$)$_2$— | —NHC(O)— |
| VIII, IX, X | —(CH$_2$)$_{14}$CH$_3$ | —(CH$_2$)$_2$CH$_3$ | —(CH$_2$)$_2$O(CH$_2$)$_2$— | —NHC(O)— |
| VIII, IX, X | —(CH$_2$)$_{16}$CH$_3$ | —(CH$_2$)$_2$CH$_3$ | —(CH$_2$)$_2$O(CH$_2$)$_2$— | —NHC(O)— |
| VIII, IX, X | —(CH$_2$)$_{18}$CH$_3$ | —(CH$_2$)$_2$CH$_3$ | —(CH$_2$)$_2$O(CH$_2$)$_2$— | —NHC(O)— |
| VIII, IX, X | —(CH$_2$)$_7$CH=CH(CH$_2$)$_5$CH$_3$ | —(CH$_2$)$_2$CH$_3$ | —(CH$_2$)$_2$O(CH$_2$)$_2$— | —NHC(O)— |
| VIII, IX, X | —(CH$_2$)$_7$CH=CH(CH$_2$)$_7$CH$_3$ | —(CH$_2$)$_2$CH$_3$ | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_2$O(CH$_2$)$_2$— | —NHC(O)— |
| VIII, IX, X | —(CH$_2$)$_6$(CH$_2$CH=CH)$_3$CH$_2$CH$_3$ | —(CH$_2$)$_2$CH$_3$ | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_2$O(CH$_2$)$_2$— | —NHC(O)— |
| VIII, X | —(CH$_2$)$_{10}$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_{12}$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_{14}$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_{16}$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_{18}$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_7$CH=CH(CH$_2$)$_5$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_7$CH=CH(CH$_2$)$_7$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_2$O(CH$_2$)$_2$— | —NHC(O)— |
| VIII, X | —(CH$_2$)$_{10}$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_{12}$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_{14}$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_{16}$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_{18}$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_7$CH=CH(CH$_2$)$_5$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_7$CH=CH(CH$_2$)$_7$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_2$O(CH$_2$)$_2$— | —NHC(O)— |
| VIII, X | —(CH$_2$)$_{10}$CH$_3$ | —(CH$_2$)$_3$CH$_3$ | —(CH$_2$)$_2$O(CH$_2$)$_2$— | —NHC(O)— |
| VIII, IX, X | —(CH$_2$)$_{12}$CH$_3$ | —(CH$_2$)$_3$CH$_3$ | —(CH$_2$)$_2$O(CH$_2$)$_2$— | —NHC(O)— |
| VIII, IX, X | —(CH$_2$)$_{14}$CH$_3$ | —(CH$_2$)$_3$CH$_3$ | —(CH$_2$)$_2$O(CH$_2$)$_2$— | —NHC(O)— |
| VIII, IX, X | —(CH$_2$)$_{16}$CH$_3$ | —(CH$_2$)$_3$CH$_3$ | —(CH$_2$)$_2$O(CH$_2$)$_2$— | —NHC(O)— |
| VIII, IX, X | —(CH$_2$)$_{18}$CH$_3$ | —(CH$_2$)$_3$CH$_3$ | —(CH$_2$)$_2$O(CH$_2$)$_2$— | —NHC(O)— |
| VIII, IX, X | —(CH$_2$)$_7$CH=CH(CH$_2$)$_5$CH$_3$ | —(CH$_2$)$_3$CH$_3$ | —(CH$_2$)$_2$O(CH$_2$)$_2$— | —NHC(O)— |
| VIII, IX, X | —(CH$_2$)$_7$CH=CH(CH$_2$)$_7$CH$_3$ | —(CH$_2$)$_3$CH$_3$ | —(CH$_2$)$_2$O(CH$_2$)$_2$— | —NHC(O)— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_2$O(CH$_2$)$_2$— | —NHC(O)— |

-continued

| | | | | |
|---|---|---|---|---|
| VIII, IX, X | —(CH$_2$)$_6$(CH$_2$CH=CH)$_3$CH$_2$CH$_3$ | —(CH$_2$)$_3$CH$_3$ | —(CH$_2$)$_2$O(CH$_2$)$_2$— | —NHC(O)— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_2$O(CH$_2$)$_2$— | —NHC(O)— |
| IX, X | —(CH$_2$)$_{10}$CH$_3$ | H | —(CH$_2$)$_3$— | —NHS(O)$_2$— |
| IX, X | —(CH$_2$)$_{12}$CH$_3$ | H | —(CH$_2$)$_3$— | —NHS(O)$_2$— |
| IX, X | —(CH$_2$)$_{14}$CH$_3$ | H | —(CH$_2$)$_3$— | —NHS(O)$_2$— |
| VIII, IX, X | —(CH$_2$)$_{16}$CH$_3$ | H | —(CH$_2$)$_3$— | —NHS(O)$_2$— |
| VIII, IX, X | —(CH$_2$)$_{18}$CH$_3$ | H | —(CH$_2$)$_3$— | —NHS(O)$_2$— |
| IX, X | —(CH$_2$)$_7$CH=CH(CH$_2$)$_5$CH$_3$ | H | —(CH$_2$)$_3$— | —NHS(O)$_2$— |
| VIII, IX, X | —(CH$_2$)$_7$CH=CH(CH$_2$)$_7$CH$_3$ | H | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | H | —(CH$_2$)$_3$— | —NHS(O)$_2$— |
| VIII, IX, X | —(CH$_2$)$_6$(CH$_2$CH=CH)$_3$CH$_2$CH$_3$ | H | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | H | —(CH$_2$)$_3$— | —NHS(O)$_2$— |
| IX, X | —(CH$_2$)$_{10}$CH$_3$ | —CH$_3$ | —(CH$_2$)$_3$— | —NHS(O)$_2$— |
| IX, X | —(CH$_2$)$_{12}$CH$_3$ | —CH$_3$ | —(CH$_2$)$_3$— | —NHS(O)$_2$— |
| IX, X | —(CH$_2$)$_{14}$CH$_3$ | —CH$_3$ | —(CH$_2$)$_3$— | —NHS(O)$_2$— |
| VIII, IX, X | —(CH$_2$)$_{16}$CH$_3$ | —CH$_3$ | —(CH$_2$)$_3$— | —NHS(O)$_2$— |
| VIII, IX, X | —(CH$_2$)$_{18}$CH$_3$ | —CH$_3$ | —(CH$_2$)$_3$— | —NHS(O)$_2$— |
| IX, X | —(CH$_2$)$_7$CH=CH(CH$_2$)$_5$CH$_3$ | —CH$_3$ | —(CH$_2$)$_3$— | —NHS(O)$_2$— |
| VIII, IX, X | —(CH$_2$)$_7$CH=CH(CH$_2$)$_7$CH$_3$ | —CH$_3$ | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | —CH$_3$ | —(CH$_2$)$_3$— | —NHS(O)$_2$— |
| VIII, IX, X | —(CH$_2$)$_6$(CH$_2$CH=CH)$_3$CH$_2$CH$_3$ | —CH$_3$ | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | —CH$_3$ | —(CH$_2$)$_3$— | —NHS(O)$_2$— |
| IX, X | —(CH$_2$)$_{10}$CH$_3$ | —CH$_2$CH$_3$ | —(CH$_2$)$_3$— | —NHS(O)$_2$— |
| IX, X | —(CH$_2$)$_{12}$CH$_3$ | —CH$_2$CH$_3$ | —(CH$_2$)$_3$— | —NHS(O)$_2$— |
| IX, X | —(CH$_2$)$_{14}$CH$_3$ | —CH$_2$CH$_3$ | —(CH$_2$)$_3$— | —NHS(O)$_2$— |
| VIII, IX, X | —(CH$_2$)$_{16}$CH$_3$ | —CH$_2$CH$_3$ | —(CH$_2$)$_3$— | —NHS(O)$_2$— |
| VIII, IX, X | —(CH$_2$)$_{18}$CH$_3$ | —CH$_2$CH$_3$ | —(CH$_2$)$_3$— | —NHS(O)$_2$— |
| IX, X | —(CH$_2$)$_7$CH=CH(CH$_2$)$_5$CH$_3$ | —CH$_2$CH$_3$ | —(CH$_2$)$_3$— | —NHS(O)$_2$— |
| VIII, IX, X | —(CH$_2$)$_7$CH=CH(CH$_2$)$_7$CH$_3$ | —CH$_2$CH$_3$ | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | —CH$_2$CH$_3$ | —(CH$_2$)$_3$— | —NHS(O)$_2$— |
| VIII, IX, X | —(CH$_2$)$_6$(CH$_2$CH=CH)$_3$CH$_2$CH$_3$ | —CH$_2$CH$_3$ | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | —CH$_2$CH$_3$ | —(CH$_2$)$_3$— | —NHS(O)$_2$— |
| IX, X | —(CH$_2$)$_{10}$CH$_3$ | —(CH$_2$)$_2$CH$_3$ | —(CH$_2$)$_3$— | —NHS(O)$_2$— |
| IX, X | —(CH$_2$)$_{12}$CH$_3$ | —(CH$_2$)$_2$CH$_3$ | —(CH$_2$)$_3$— | —NHS(O)$_2$— |
| IX, X | —(CH$_2$)$_{14}$CH$_3$ | —(CH$_2$)$_2$CH$_3$ | —(CH$_2$)$_3$— | —NHS(O)$_2$— |
| VIII, IX, X | —(CH$_2$)$_{16}$CH$_3$ | —(CH$_2$)$_2$CH$_3$ | —(CH$_2$)$_3$— | —NHS(O)$_2$— |
| VIII, IX, X | —(CH$_2$)$_{18}$CH$_3$ | —(CH$_2$)$_2$CH$_3$ | —(CH$_2$)$_3$— | —NHS(O)$_2$— |
| IX, X | —(CH$_2$)$_7$CH=CH(CH$_2$)$_5$CH$_3$ | —(CH$_2$)$_2$CH$_3$ | —(CH$_2$)$_3$— | —NHS(O)$_2$— |
| VIII, IX, X | —(CH$_2$)$_7$CH=CH(CH$_2$)$_7$CH$_3$ | —(CH$_2$)$_2$CH$_3$ | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_3$— | —NHS(O)$_2$— |
| VIII, IX, X | —(CH$_2$)$_6$(CH$_2$CH=CH)$_3$CH$_2$CH$_3$ | —(CH$_2$)$_2$CH$_3$ | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_3$— | —NHS(O)$_2$— |
| IX, X | —(CH$_2$)$_{10}$CH$_3$ | —CH$_2$OCH$_2$CH$_3$ | —(CH$_2$)$_3$— | —NHS(O)$_2$— |
| IX, X | —(CH$_2$)$_{12}$CH$_3$ | —CH$_2$OCH$_2$CH$_3$ | —(CH$_2$)$_3$— | —NHS(O)$_2$— |
| IX, X | —(CH$_2$)$_{14}$CH$_3$ | —CH$_2$OCH$_2$CH$_3$ | —(CH$_2$)$_3$— | —NHS(O)$_2$— |
| VIII, IX, X | —(CH$_2$)$_{16}$CH$_3$ | —CH$_2$OCH$_2$CH$_3$ | —(CH$_2$)$_3$— | —NHS(O)$_2$— |
| VIII, IX, X | —(CH$_2$)$_{18}$CH$_3$ | —CH$_2$OCH$_2$CH$_3$ | —(CH$_2$)$_3$— | —NHS(O)$_2$— |
| IX, X | —(CH$_2$)$_7$CH=CH(CH$_2$)$_5$CH$_3$ | —CH$_2$OCH$_2$CH$_3$ | —(CH$_2$)$_3$— | —NHS(O)$_2$— |
| VIII, IX, X | —(CH$_2$)$_7$CH=CH(CH$_2$)$_7$CH$_3$ | —CH$_2$OCH$_2$CH$_3$ | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_3$— | —NHS(O)$_2$— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_3$— | —NHS(O)$_2$— |
| IX, X | —(CH$_2$)$_{10}$CH$_3$ | —(CH$_2$)$_2$OCH$_3$ | —(CH$_2$)$_3$— | —NHS(O)$_2$— |
| IX, X | —(CH$_2$)$_{12}$CH$_3$ | —(CH$_2$)$_2$OCH$_3$ | —(CH$_2$)$_3$— | —NHS(O)$_2$— |
| IX, X | —(CH$_2$)$_{14}$CH$_3$ | —(CH$_2$)$_2$OCH$_3$ | —(CH$_2$)$_3$— | —NHS(O)$_2$— |
| VIII, IX, X | —(CH$_2$)$_{16}$CH$_3$ | —(CH$_2$)$_2$OCH$_3$ | —(CH$_2$)$_3$— | —NHS(O)$_2$— |
| VIII, IX, X | —(CH$_2$)$_{18}$CH$_3$ | —(CH$_2$)$_2$OCH$_3$ | —(CH$_2$)$_3$— | —NHS(O)$_2$— |
| IX, X | —(CH$_2$)$_7$CH=CH(CH$_2$)$_5$CH$_3$ | —(CH$_2$)$_2$OCH$_3$ | —(CH$_2$)$_3$— | —NHS(O)$_2$— |
| VIII, IX, X | —(CH$_2$)$_7$CH=CH(CH$_2$)$_7$CH$_3$ | —(CH$_2$)$_2$OCH$_3$ | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_3$— | —NHS(O)$_2$— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_3$— | —NHS(O)$_2$— |
| IX, X | —(CH$_2$)$_{10}$CH$_3$ | —(CH$_2$)$_3$CH$_3$ | —(CH$_2$)$_3$— | —NHS(O)$_2$— |
| IX, X | —(CH$_2$)$_{12}$CH$_3$ | —(CH$_2$)$_3$CH$_3$ | —(CH$_2$)$_3$— | —NHS(O)$_2$— |
| IX, X | —(CH$_2$)$_{14}$CH$_3$ | —(CH$_2$)$_3$CH$_3$ | —(CH$_2$)$_3$— | —NHS(O)$_2$— |
| VIII, IX, X | —(CH$_2$)$_{16}$CH$_3$ | —(CH$_2$)$_3$CH$_3$ | —(CH$_2$)$_3$— | —NHS(O)$_2$— |
| VIII, IX, X | —(CH$_2$)$_{18}$CH$_3$ | —(CH$_2$)$_3$CH$_3$ | —(CH$_2$)$_3$— | —NHS(O)$_2$— |
| IX, X | —(CH$_2$)$_7$CH=CH(CH$_2$)$_5$CH$_3$ | —(CH$_2$)$_3$CH$_3$ | —(CH$_2$)$_3$— | —NHS(O)$_2$— |
| VIII, IX, X | —(CH$_2$)$_7$CH=CH(CH$_2$)$_7$CH$_3$ | —(CH$_2$)$_3$CH$_3$ | —(CH$_2$)$_3$— | —NHS(O)$_2$— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_3$— | —NHS(O)$_2$— |
| VIII, IX, X | —(CH$_2$)$_6$(CH$_2$CH=CH)$_3$CH$_2$CH$_3$ | —(CH$_2$)$_3$CH$_3$ | —(CH$_2$)$_3$— | —NHS(O)$_2$— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_3$— | —NHS(O)$_2$— |
| IX, X | —(CH$_2$)$_{10}$CH$_3$ | H | —(CH$_2$)$_4$— | —NHS(O)$_2$— |
| IX, X | —(CH$_2$)$_{12}$CH$_3$ | H | —(CH$_2$)$_4$— | —NHS(O)$_2$— |
| IX, X | —(CH$_2$)$_{14}$CH$_3$ | H | —(CH$_2$)$_4$— | —NHS(O)$_2$— |
| VIII, IX, X | —(CH$_2$)$_{16}$CH$_3$ | H | —(CH$_2$)$_4$— | —NHS(O)$_2$— |
| VIII, IX, X | —(CH$_2$)$_{18}$CH$_3$ | H | —(CH$_2$)$_4$— | —NHS(O)$_2$— |
| IX, X | —(CH$_2$)$_7$CH=CH(CH$_2$)$_5$CH$_3$ | H | —(CH$_2$)$_4$— | —NHS(O)$_2$— |
| VIII, IX, X | —(CH$_2$)$_7$CH=CH(CH$_2$)$_7$CH$_3$ | H | —(CH$_2$)$_4$— | —NHS(O)$_2$— |

-continued

| | | | | |
|---|---|---|---|---|
| VIII, IX, X | —(CH$_2$)$_6$(CH$_2$CH=CH)$_2$(CH$_2$)$_4$CH$_3$ | H | —(CH$_2$)$_4$— | —NHS(O)$_2$— |
| VIII, IX, X | —(CH$_2$)$_6$(CH$_2$CH=CH)$_3$CH$_2$CH$_3$ | H | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | H | —(CH$_2$)$_4$— | —NHS(O)$_2$— |
| IX, X | —(CH$_2$)$_{10}$CH$_3$ | —CH$_3$ | —(CH$_2$)$_4$— | —NHS(O)$_2$— |
| IX, X | —(CH$_2$)$_{12}$CH$_3$ | —CH$_3$ | —(CH$_2$)$_4$— | —NHS(O)$_2$— |
| IX, X | —(CH$_2$)$_{14}$CH$_3$ | —CH$_3$ | —(CH$_2$)$_4$— | —NHS(O)$_2$— |
| VIII, IX, X | —(CH$_2$)$_{16}$CH$_3$ | —CH$_3$ | —(CH$_2$)$_4$— | —NHS(O)$_2$— |
| VIII, IX, X | —(CH$_2$)$_{18}$CH$_3$ | —CH$_3$ | —(CH$_2$)$_4$— | —NHS(O)$_2$— |
| IX, X | —(CH$_2$)$_7$CH=CH(CH$_2$)$_5$CH$_3$ | —CH$_3$ | —(CH$_2$)$_4$— | —NHS(O)$_2$— |
| VIII, IX, X | —(CH$_2$)$_7$CH=CH(CH$_2$)$_7$CH$_3$ | —CH$_3$ | —(CH$_2$)$_4$— | —NHS(O)$_2$— |
| VIII, IX, X | —(CH$_2$)$_6$(CH$_2$CH=CH)$_2$(CH$_2$)$_4$CH$_3$ | —CH$_3$ | —(CH$_2$)$_4$— | —NHS(O)$_2$— |
| VIII, IX, X | —(CH$_2$)$_6$(CH$_2$CH=CH)$_3$CH$_2$CH$_3$ | —CH$_3$ | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | —CH$_3$ | —(CH$_2$)$_4$— | —NHS(O)$_2$— |
| IX, X | —(CH$_2$)$_{10}$CH$_3$ | —CH$_2$CH$_3$ | —(CH$_2$)$_4$— | —NHS(O)$_2$— |
| IX, X | —(CH$_2$)$_{12}$CH$_3$ | —CH$_2$CH$_3$ | —(CH$_2$)$_4$— | —NHS(O)$_2$— |
| IX, X | —(CH$_2$)$_{14}$CH$_3$ | —CH$_2$CH$_3$ | —(CH$_2$)$_4$— | —NHS(O)$_2$— |
| VIII, IX, X | —(CH$_2$)$_{16}$CH$_3$ | —CH$_2$CH$_3$ | —(CH$_2$)$_4$— | —NHS(O)$_2$— |
| VIII, IX, X | —(CH$_2$)$_{18}$CH$_3$ | —CH$_2$CH$_3$ | —(CH$_2$)$_4$— | —NHS(O)$_2$— |
| IX, X | —(CH$_2$)$_7$CH=CH(CH$_2$)$_5$CH$_3$ | —CH$_2$CH$_3$ | —(CH$_2$)$_4$— | —NHS(O)$_2$— |
| VIII, IX, X | —(CH$_2$)$_7$CH=CH(CH$_2$)$_7$CH$_3$ | —CH$_2$CH$_3$ | —(CH$_2$)$_4$— | —NHS(O)$_2$— |
| VIII, IX, X | —(CH$_2$)$_6$(CH$_2$CH=CH)$_2$(CH$_2$)$_4$CH$_3$ | —CH$_2$CH$_3$ | —(CH$_2$)$_4$— | —NHS(O)$_2$— |
| VIII, IX, X | —(CH$_2$)$_6$(CH$_2$CH=CH)$_3$CH$_2$CH$_3$ | —CH$_2$CH$_3$ | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | —CH$_2$CH$_3$ | —(CH$_2$)$_4$— | —NHS(O)$_2$— |
| IX, X | —(CH$_2$)$_{10}$CH$_3$ | —(CH$_2$)$_2$CH$_3$ | —(CH$_2$)$_4$— | —NHS(O)$_2$— |
| IX, X | —(CH$_2$)$_{12}$CH$_3$ | —(CH$_2$)$_2$CH$_3$ | —(CH$_2$)$_4$— | —NHS(O)$_2$— |
| IX, X | —(CH$_2$)$_{14}$CH$_3$ | —(CH$_2$)$_2$CH$_3$ | —(CH$_2$)$_4$— | —NHS(O)$_2$— |
| VIII, IX, X | —(CH$_2$)$_{16}$CH$_3$ | —(CH$_2$)$_2$CH$_3$ | —(CH$_2$)$_4$— | —NHS(O)$_2$— |
| VIII, IX, X | —(CH$_2$)$_{18}$CH$_3$ | —(CH$_2$)$_2$CH$_3$ | —(CH$_2$)$_4$— | —NHS(O)$_2$— |
| IX, X | —(CH$_2$)$_7$CH=CH(CH$_2$)$_5$CH$_3$ | —(CH$_2$)$_2$CH$_3$ | —(CH$_2$)$_4$— | —NHS(O)$_2$— |
| VIII, IX, X | —(CH$_2$)$_7$CH=CH(CH$_2$)$_7$CH$_3$ | —(CH$_2$)$_2$CH$_3$ | —(CH$_2$)$_4$— | —NHS(O)$_2$— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_4$— | —NHS(O)$_2$— |
| VIII, IX, X | —(CH$_2$)$_6$(CH$_2$CH=CH)$_3$CH$_2$CH$_3$ | —(CH$_2$)$_2$CH$_3$ | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_4$— | —NHS(O)$_2$— |
| IX, X | —(CH$_2$)$_{10}$CH$_3$ | —CH$_2$OCH$_2$CH$_3$ | —(CH$_2$)$_4$— | —NHS(O)$_2$— |
| IX, X | —(CH$_2$)$_{12}$CH$_3$ | —CH$_2$OCH$_2$CH$_3$ | —(CH$_2$)$_4$— | —NHS(O)$_2$— |
| IX, X | —(CH$_2$)$_{14}$CH$_3$ | —CH$_2$OCH$_2$CH$_3$ | —(CH$_2$)$_4$— | —NHS(O)$_2$— |
| VIII, IX, X | —(CH$_2$)$_{16}$CH$_3$ | —CH$_2$OCH$_2$CH$_3$ | —(CH$_2$)$_4$— | —NHS(O)$_2$— |
| VIII, IX, X | —(CH$_2$)$_{18}$CH$_3$ | —CH$_2$OCH$_2$CH$_3$ | —(CH$_2$)$_4$— | —NHS(O)$_2$— |
| IX, X | —(CH$_2$)$_7$CH=CH(CH$_2$)$_5$CH$_3$ | —CH$_2$OCH$_2$CH$_3$ | —(CH$_2$)$_4$— | —NHS(O)$_2$— |
| VIII, IX, X | —(CH$_2$)$_7$CH=CH(CH$_2$)$_7$CH$_3$ | —CH$_2$OCH$_2$CH$_3$ | —(CH$_2$)$_4$— | —NHS(O)$_2$— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_4$— | —NHS(O)$_2$— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_4$— | —NHS(O)$_2$— |
| IX, X | —(CH$_2$)$_{10}$CH$_3$ | —(CH$_2$)$_2$OCH$_3$ | —(CH$_2$)$_4$— | —NHS(O)$_2$— |
| IX, X | —(CH$_2$)$_{12}$CH$_3$ | —(CH$_2$)$_2$OCH$_3$ | —(CH$_2$)$_4$— | —NHS(O)$_2$— |
| IX, X | —(CH$_2$)$_{14}$CH$_3$ | —(CH$_2$)$_2$OCH$_3$ | —(CH$_2$)$_4$— | —NHS(O)$_2$— |
| VIII, IX, X | —(CH$_2$)$_{16}$CH$_3$ | —(CH$_2$)$_2$OCH$_3$ | —(CH$_2$)$_4$— | —NHS(O)$_2$— |
| VIII, IX, X | —(CH$_2$)$_{18}$CH$_3$ | —(CH$_2$)$_2$OCH$_3$ | —(CH$_2$)$_4$— | —NHS(O)$_2$— |
| IX, X | —(CH$_2$)$_7$CH=CH(CH$_2$)$_5$CH$_3$ | —(CH$_2$)$_2$OCH$_3$ | —(CH$_2$)$_4$— | —NHS(O)$_2$— |
| VIII, IX, X | —(CH$_2$)$_7$CH=CH(CH$_2$)$_7$CH$_3$ | —(CH$_2$)$_2$OCH$_3$ | —(CH$_2$)$_4$— | —NHS(O)$_2$— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_4$— | —NHS(O)$_2$— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_4$— | —NHS(O)$_2$— |
| IX, X | —(CH$_2$)$_{10}$CH$_3$ | —(CH$_2$)$_3$CH$_3$ | —(CH$_2$)$_4$— | —NHS(O)$_2$— |
| IX, X | —(CH$_2$)$_{12}$CH$_3$ | —(CH$_2$)$_3$CH$_3$ | —(CH$_2$)$_4$— | —NHS(O)$_2$— |
| IX, X | —(CH$_2$)$_{14}$CH$_3$ | —(CH$_2$)$_3$CH$_3$ | —(CH$_2$)$_4$— | —NHS(O)$_2$— |
| VIII, IX, X | —(CH$_2$)$_{16}$CH$_3$ | —(CH$_2$)$_3$CH$_3$ | —(CH$_2$)$_4$— | —NHS(O)$_2$— |
| VIII, IX, X | —(CH$_2$)$_{18}$CH$_3$ | —(CH$_2$)$_3$CH$_3$ | —(CH$_2$)$_4$— | —NHS(O)$_2$— |
| IX, X | —(CH$_2$)$_7$CH=CH(CH$_2$)$_5$CH$_3$ | —(CH$_2$)$_3$CH$_3$ | —(CH$_2$)$_4$— | —NHS(O)$_2$— |
| VIII, IX, X | —(CH$_2$)$_7$CH=CH(CH$_2$)$_7$CH$_3$ | —(CH$_2$)$_3$CH$_3$ | —(CH$_2$)$_4$— | —NHS(O)$_2$— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_4$— | —NHS(O)$_2$— |
| VIII, IX, X | —(CH$_2$)$_6$(CH$_2$CH=CH)$_3$CH$_2$CH$_3$ | —(CH$_2$)$_3$CH$_3$ | —(CH$_2$)$_4$— | —NHS(O)$_2$— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_4$— | —NHS(O)$_2$— |
| IX, X | —(CH$_2$)$_{10}$CH$_3$ | H | —(CH$_2$)$_5$— | —NHS(O)$_2$— |
| IX, X | —(CH$_2$)$_{12}$CH$_3$ | H | —(CH$_2$)$_5$— | —NHS(O)$_2$— |
| IX, X | —(CH$_2$)$_{14}$CH$_3$ | H | —(CH$_2$)$_5$— | —NHS(O)$_2$— |
| VIII, IX, X | —(CH$_2$)$_{16}$CH$_3$ | H | —(CH$_2$)$_5$— | —NHS(O)$_2$— |
| VIII, IX, X | —(CH$_2$)$_{18}$CH$_3$ | H | —(CH$_2$)$_5$— | —NHS(O)$_2$— |
| IX, X | —(CH$_2$)$_7$CH=CH(CH$_2$)$_5$CH$_3$ | H | —(CH$_2$)$_5$— | —NHS(O)$_2$— |
| VIII, IX, X | —(CH$_2$)$_7$CH=CH(CH$_2$)$_7$CH$_3$ | H | —(CH$_2$)$_5$— | —NHS(O)$_2$— |
| VIII, IX, X | —(CH$_2$)$_6$(CH$_2$CH=CH)$_2$(CH$_2$)$_4$CH$_3$ | H | —(CH$_2$)$_5$— | —NHS(O)$_2$— |
| VIII, IX, X | —(CH$_2$)$_6$(CH$_2$CH=CH)$_3$CH$_2$CH$_3$ | H | —(CH$_2$)$_5$— | —NHS(O)$_2$— |
| VIII, IX, X | —(CH$_2$)$_2$(CH$_2$CH=CH)$_4$(CH$_2$)$_4$CH$_3$ | H | —(CH$_2$)$_5$— | —NHS(O)$_2$— |
| IX, X | —(CH$_2$)$_{10}$CH$_3$ | —CH$_3$ | —(CH$_2$)$_5$— | —NHS(O)$_2$— |
| IX, X | —(CH$_2$)$_{12}$CH$_3$ | —CH$_3$ | —(CH$_2$)$_5$— | —NHS(O)$_2$— |
| IX, X | —(CH$_2$)$_{14}$CH$_3$ | —CH$_3$ | —(CH$_2$)$_5$— | —NHS(O)$_2$— |
| VIII, IX, X | —(CH$_2$)$_{16}$CH$_3$ | —CH$_3$ | —(CH$_2$)$_5$— | —NHS(O)$_2$— |
| VIII, IX, X | —(CH$_2$)$_{18}$CH$_3$ | —CH$_3$ | —(CH$_2$)$_5$— | —NHS(O)$_2$— |
| IX, X | —(CH$_2$)$_7$CH=CH(CH$_2$)$_5$CH$_3$ | —CH$_3$ | —(CH$_2$)$_5$— | —NHS(O)$_2$— |

| | | | | |
|---|---|---|---|---|
| VIII, IX, X | —(CH$_2$)$_7$CH═CH(CH$_2$)$_7$CH$_3$ | —CH$_3$ | —(CH$_2$)$_5$— | —NHS(O)$_2$— |
| VIII, IX, X | —(CH$_2$)$_6$(CH$_2$CH═CH)$_2$(CH$_2$)$_4$CH$_3$ | —CH$_3$ | —(CH$_2$)$_5$— | —NHS(O)$_2$— |
| VIII, IX, X | —(CH$_2$)$_6$(CH$_2$CH═CH)$_3$CH$_2$CH$_3$ | —CH$_3$ | —(CH$_2$)$_5$— | —NHS(O)$_2$— |
| VIII, IX, X | —(CH$_2$)$_2$(CH$_2$CH═CH)$_4$(CH$_2$)$_4$CH$_3$ | —CH$_3$ | —(CH$_2$)$_5$— | —NHS(O)$_2$— |
| IX, X | —(CH$_2$)$_{10}$CH$_3$ | —CH$_2$CH$_3$ | —(CH$_2$)$_5$— | —NHS(O)$_2$— |
| IX, X | —(CH$_2$)$_{12}$CH$_3$ | —CH$_2$CH$_3$ | —(CH$_2$)$_5$— | —NHS(O)$_2$— |
| IX, X | —(CH$_2$)$_{14}$CH$_3$ | —CH$_2$CH$_3$ | —(CH$_2$)$_5$— | —NHS(O)$_2$— |
| VIII, IX, X | —(CH$_2$)$_{16}$CH$_3$ | —CH$_2$CH$_3$ | —(CH$_2$)$_5$— | —NHS(O)$_2$— |
| VIII, IX, X | —(CH$_2$)$_{18}$CH$_3$ | —CH$_2$CH$_3$ | —(CH$_2$)$_5$— | —NHS(O)$_2$— |
| IX, X | —(CH$_2$)$_7$CH═CH(CH$_2$)$_5$CH$_3$ | —CH$_2$CH$_3$ | —(CH$_2$)$_5$— | —NHS(O)$_2$— |
| VIII, IX, X | —(CH$_2$)$_7$CH═CH(CH$_2$)$_7$CH$_3$ | —CH$_2$CH$_3$ | —(CH$_2$)$_5$— | —NHS(O)$_2$— |
| VIII, IX, X | —(CH$_2$)$_6$(CH$_2$CH═CH)$_2$(CH$_2$)$_4$CH$_3$ | —CH$_2$CH$_3$ | —(CH$_2$)$_5$— | —NHS(O)$_2$— |
| VIII, IX, X | —(CH$_2$)$_6$(CH$_2$CH═CH)$_3$CH$_2$CH$_3$ | —CH$_2$CH$_3$ | —(CH$_2$)$_5$— | —NHS(O)$_2$— |
| VIII, IX, X | —(CH$_2$)$_2$(CH$_2$CH═CH)$_4$(CH$_2$)$_4$CH$_3$ | —CH$_2$CH$_3$ | —(CH$_2$)$_5$— | —NHS(O)$_2$— |
| IX, X | —(CH$_2$)$_{10}$CH$_3$ | —(CH$_2$)$_2$CH$_3$ | —(CH$_2$)$_5$— | —NHS(O)$_2$— |
| IX, X | —(CH$_2$)$_{12}$CH$_3$ | —(CH$_2$)$_2$CH$_3$ | —(CH$_2$)$_5$— | —NHS(O)$_2$— |
| IX, X | —(CH$_2$)$_{14}$CH$_3$ | —(CH$_2$)$_2$CH$_3$ | —(CH$_2$)$_5$— | —NHS(O)$_2$— |
| VIII, IX, X | —(CH$_2$)$_{16}$CH$_3$ | —(CH$_2$)$_2$CH$_3$ | —(CH$_2$)$_5$— | —NHS(O)$_2$— |
| VIII, IX, X | —(CH$_2$)$_{18}$CH$_3$ | —(CH$_2$)$_2$CH$_3$ | —(CH$_2$)$_5$— | —NHS(O)$_2$— |
| IX, X | —(CH$_2$)$_7$CH═CH(CH$_2$)$_5$CH$_3$ | —(CH$_2$)$_2$CH$_3$ | —(CH$_2$)$_5$— | —NHS(O)$_2$— |
| VIII, IX, X | —(CH$_2$)$_7$CH═CH(CH$_2$)$_7$CH$_3$ | —(CH$_2$)$_2$CH$_3$ | —(CH$_2$)$_5$— | —NHS(O)$_2$— |
| VIII, IX, X | —(CH$_2$)$_6$(CH$_2$CH═CH)$_2$(CH$_2$)$_4$CH$_3$ | —(CH$_2$)$_2$CH$_3$ | —(CH$_2$)$_5$— | —NHS(O)$_2$— |
| VIII, IX, X | —(CH$_2$)$_6$(CH$_2$CH═CH)$_3$CH$_2$CH$_3$ | —(CH$_2$)$_2$CH$_3$ | —(CH$_2$)$_5$— | —NHS(O)$_2$— |
| VIII, IX, X | —(CH$_2$)$_2$(CH$_2$CH═CH)$_4$(CH$_2$)$_4$CH$_3$ | —(CH$_2$)$_2$CH$_3$ | —(CH$_2$)$_5$— | —NHS(O)$_2$— |
| IX, X | —(CH$_2$)$_{10}$CH$_3$ | —CH$_2$OCH$_2$CH$_3$ | —(CH$_2$)$_5$— | —NHS(O)$_2$— |
| IX, X | —(CH$_2$)$_{12}$CH$_3$ | —CH$_2$OCH$_2$CH$_3$ | —(CH$_2$)$_5$— | —NHS(O)$_2$— |
| IX, X | —(CH$_2$)$_{14}$CH$_3$ | —CH$_2$OCH$_2$CH$_3$ | —(CH$_2$)$_5$— | —NHS(O)$_2$— |
| VIII, IX, X | —(CH$_2$)$_{16}$CH$_3$ | —CH$_2$OCH$_2$CH$_3$ | —(CH$_2$)$_5$— | —NHS(O)$_2$— |
| VIII, IX, X | —(CH$_2$)$_{18}$CH$_3$ | —CH$_2$OCH$_2$CH$_3$ | —(CH$_2$)$_5$— | —NHS(O)$_2$— |
| IX, X | —(CH$_2$)$_7$CH═CH(CH$_2$)$_5$CH$_3$ | —CH$_2$OCH$_2$CH$_3$ | —(CH$_2$)$_5$— | —NHS(O)$_2$— |
| VIII, IX, X | —(CH$_2$)$_7$CH═CH(CH$_2$)$_7$CH$_3$ | —CH$_2$OCH$_2$CH$_3$ | —(CH$_2$)$_5$— | —NHS(O)$_2$— |
| VIII, IX, X | —(CH$_2$)$_6$(CH$_2$CH═CH)$_2$(CH$_2$)$_4$CH$_3$ | —CH$_2$OCH$_2$CH$_3$ | —(CH$_2$)$_5$— | —NHS(O)$_2$— |
| VIII, IX, X | —(CH$_2$)$_6$(CH$_2$CH═CH)$_3$CH$_2$CH$_3$ | —CH$_2$OCH$_2$CH$_3$ | —(CH$_2$)$_5$— | —NHS(O)$_2$— |
| VIII, IX, X | —(CH$_2$)$_2$(CH$_2$CH═CH)$_4$(CH$_2$)$_4$CH$_3$ | —CH$_2$OCH$_2$CH$_3$ | —(CH$_2$)$_5$— | —NHS(O)$_2$— |
| IX, X | —(CH$_2$)$_{10}$CH$_3$ | —(CH$_2$)$_2$OCH$_3$ | —(CH$_2$)$_5$— | —NHS(O)$_2$— |
| IX, X | —(CH$_2$)$_{12}$CH$_3$ | —(CH$_2$)$_2$OCH$_3$ | —(CH$_2$)$_5$— | —NHS(O)$_2$— |
| IX, X | —(CH$_2$)$_{14}$CH$_3$ | —(CH$_2$)$_2$OCH$_3$ | —(CH$_2$)$_5$— | —NHS(O)$_2$— |
| VIII, IX, X | —(CH$_2$)$_{16}$CH$_3$ | —(CH$_2$)$_2$OCH$_3$ | —(CH$_2$)$_5$— | —NHS(O)$_2$— |
| VIII, IX, X | —(CH$_2$)$_{18}$CH$_3$ | —(CH$_2$)$_2$OCH$_3$ | —(CH$_2$)$_5$— | —NHS(O)$_2$— |
| IX, X | —(CH$_2$)$_7$CH═CH(CH$_2$)$_5$CH$_3$ | —(CH$_2$)$_2$OCH$_3$ | —(CH$_2$)$_5$— | —NHS(O)$_2$— |
| VIII, IX, X | —(CH$_2$)$_7$CH═CH(CH$_2$)$_7$CH$_3$ | —(CH$_2$)$_2$OCH$_3$ | —(CH$_2$)$_5$— | —NHS(O)$_2$— |
| VIII, IX, X | —(CH$_2$)$_6$(CH$_2$CH═CH)$_2$(CH$_2$)$_4$CH$_3$ | —(CH$_2$)$_2$OCH$_3$ | —(CH$_2$)$_5$— | —NHS(O)$_2$— |
| VIII, IX, X | —(CH$_2$)$_6$(CH$_2$CH═CH)$_3$CH$_2$CH$_3$ | —(CH$_2$)$_2$OCH$_3$ | —(CH$_2$)$_5$— | —NHS(O)$_2$— |
| VIII, IX, X | —(CH$_2$)$_2$(CH$_2$CH═CH)$_4$(CH$_2$)$_4$CH$_3$ | —(CH$_2$)$_2$OCH$_3$ | —(CH$_2$)$_5$— | —NHS(O)$_2$— |
| IX, X | —(CH$_2$)$_{10}$CH$_3$ | —(CH$_2$)$_3$CH$_3$ | —(CH$_2$)$_5$— | —NHS(O)$_2$— |
| IX, X | —(CH$_2$)$_{12}$CH$_3$ | —(CH$_2$)$_3$CH$_3$ | —(CH$_2$)$_5$— | —NHS(O)$_2$— |
| IX, X | —(CH$_2$)$_{14}$CH$_3$ | —(CH$_2$)$_3$CH$_3$ | —(CH$_2$)$_5$— | —NHS(O)$_2$— |
| VIII, IX, X | —(CH$_2$)$_{16}$CH$_3$ | —(CH$_2$)$_3$CH$_3$ | —(CH$_2$)$_5$— | —NHS(O)$_2$— |
| VIII, IX, X | —(CH$_2$)$_{18}$CH$_3$ | —(CH$_2$)$_3$CH$_3$ | —(CH$_2$)$_5$— | —NHS(O)$_2$— |
| IX, X | —(CH$_2$)$_7$CH═CH(CH$_2$)$_5$CH$_3$ | —(CH$_2$)$_3$CH$_3$ | —(CH$_2$)$_5$— | —NHS(O)$_2$— |
| VIII, IX, X | —(CH$_2$)$_7$CH═CH(CH$_2$)$_7$CH$_3$ | —(CH$_2$)$_3$CH$_3$ | —(CH$_2$)$_5$— | —NHS(O)$_2$— |
| VIII, IX, X | —(CH$_2$)$_6$(CH$_2$CH═CH)$_2$(CH$_2$)$_4$CH$_3$ | —(CH$_2$)$_3$CH$_3$ | —(CH$_2$)$_5$— | —NHS(O)$_2$— |
| VIII, IX, X | —(CH$_2$)$_6$(CH$_2$CH═CH)$_3$CH$_2$CH$_3$ | —(CH$_2$)$_3$CH$_3$ | —(CH$_2$)$_5$— | —NHS(O)$_2$— |
| VIII, IX, X | —(CH$_2$)$_2$(CH$_2$CH═CH)$_4$(CH$_2$)$_4$CH$_3$ | —(CH$_2$)$_3$CH$_3$ | —(CH$_2$)$_5$— | —NHS(O)$_2$— |
| IX, X | —(CH$_2$)$_{10}$CH$_3$ | H | —(CH$_2$)$_2$O(CH$_2$)$_2$— | —NHS(O)$_2$— |
| IX, X | —(CH$_2$)$_{12}$CH$_3$ | H | —(CH$_2$)$_2$O(CH$_2$)$_2$— | —NHS(O)$_2$— |
| IX, X | —(CH$_2$)$_{14}$CH$_3$ | H | —(CH$_2$)$_2$O(CH$_2$)$_2$— | —NHS(O)$_2$— |
| VIII, IX, X | —(CH$_2$)$_{16}$CH$_3$ | H | —(CH$_2$)$_2$O(CH$_2$)$_2$— | —NHS(O)$_2$— |
| VIII, IX, X | —(CH$_2$)$_{18}$CH$_3$ | H | —(CH$_2$)$_2$O(CH$_2$)$_2$— | —NHS(O)$_2$— |
| IX, X | —(CH$_2$)$_7$CH═CH(CH$_2$)$_5$CH$_3$ | H | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | H | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | H | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | H | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | H | —(CH$_2$)$_2$O(CH$_2$)$_2$— | —NHS(O)$_2$— |
| IX, X | —(CH$_2$)$_{10}$CH$_3$ | —CH$_3$ | —(CH$_2$)$_2$O(CH$_2$)$_2$— | —NHS(O)$_2$— |
| IX, X | —(CH$_2$)$_{12}$CH$_3$ | —CH$_3$ | —(CH$_2$)$_2$O(CH$_2$)$_2$— | —NHS(O)$_2$— |
| IX, X | —(CH$_2$)$_{14}$CH$_3$ | —CH$_3$ | —(CH$_2$)$_2$O(CH$_2$)$_2$— | —NHS(O)$_2$— |
| VIII, IX, X | —(CH$_2$)$_{16}$CH$_3$ | —CH$_3$ | —(CH$_2$)$_2$O(CH$_2$)$_2$— | —NHS(O)$_2$— |
| VIII, IX, X | —(CH$_2$)$_{18}$CH$_3$ | —CH$_3$ | —(CH$_2$)$_2$O(CH$_2$)$_2$— | —NHS(O)$_2$— |
| IX, X | —(CH$_2$)$_7$CH═CH(CH$_2$)$_5$CH$_3$ | —CH$_3$ | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | —CH$_3$ | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | —CH$_3$ | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | —CH$_3$ | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | —CH$_3$ | —(CH$_2$)$_2$O(CH$_2$)$_2$— | —NHS(O)$_2$— |
| IX, X | —(CH$_2$)$_{10}$CH$_3$ | —CH$_2$CH$_3$ | —(CH$_2$)$_2$O(CH$_2$)$_2$— | —NHS(O)$_2$— |
| IX, X | —(CH$_2$)$_{12}$CH$_3$ | —CH$_2$CH$_3$ | —(CH$_2$)$_2$O(CH$_2$)$_2$— | —NHS(O)$_2$— |
| IX, X | —(CH$_2$)$_{14}$CH$_3$ | —CH$_2$CH$_3$ | —(CH$_2$)$_2$O(CH$_2$)$_2$— | —NHS(O)$_2$— |
| VIII, IX, X | —(CH$_2$)$_{16}$CH$_3$ | —CH$_2$CH$_3$ | —(CH$_2$)$_2$O(CH$_2$)$_2$— | —NHS(O)$_2$— |
| VIII, IX, X | —(CH$_2$)$_{18}$CH$_3$ | —CH$_2$CH$_3$ | —(CH$_2$)$_2$O(CH$_2$)$_2$— | —NHS(O)$_2$— |

-continued

| | | | | |
|---|---|---|---|---|
| IX, X | —(CH$_2$)$_7$CH═CH(CH$_2$)$_5$CH$_3$ | —CH$_2$CH$_3$ | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | —CH$_2$CH$_3$ | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | —CH$_2$CH$_3$ | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | —CH$_2$CH$_3$ | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | —CH$_2$CH$_3$ | —(CH$_2$)$_2$O(CH$_2$)$_2$— | —NHS(O)$_2$— |
| IX, X | —(CH$_2$)$_{10}$CH$_3$ | —(CH$_2$)$_2$CH$_3$ | —(CH$_2$)$_2$O(CH$_2$)$_2$— | —NHS(O)$_2$— |
| IX, X | —(CH$_2$)$_{12}$CH$_3$ | —(CH$_2$)$_2$CH$_3$ | —(CH$_2$)$_2$O(CH$_2$)$_2$— | —NHS(O)$_2$— |
| IX, X | —(CH$_2$)$_{14}$CH$_3$ | —(CH$_2$)$_2$CH$_3$ | —(CH$_2$)$_2$O(CH$_2$)$_2$— | —NHS(O)$_2$— |
| VIII, IX, X | —(CH$_2$)$_{16}$CH$_3$ | —(CH$_2$)$_2$CH$_3$ | —(CH$_2$)$_2$O(CH$_2$)$_2$— | —NHS(O)$_2$— |
| VIII, IX, X | —(CH$_2$)$_{18}$CH$_3$ | —(CH$_2$)$_2$CH$_3$ | —(CH$_2$)$_2$O(CH$_2$)$_2$— | —NHS(O)$_2$— |
| IX, X | —(CH$_2$)$_7$CH═CH(CH$_2$)$_5$CH$_3$ | —(CH$_2$)$_2$CH$_3$ | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | —(CH$_2$)$_2$CH$_3$ | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | —(CH$_2$)$_2$CH$_3$ | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | —(CH$_2$)$_2$CH$_3$ | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | —(CH$_2$)$_2$CH$_3$ | —(CH$_2$)$_2$O(CH$_2$)$_2$— | —NHS(O)$_2$— |
| IX, X | —(CH$_2$)$_{10}$CH$_3$ | —CH$_2$OCH$_2$CH$_3$ | —(CH$_2$)$_2$O(CH$_2$)$_2$— | —NHS(O)$_2$— |
| IX, X | —(CH$_2$)$_{12}$CH$_3$ | —CH$_2$OCH$_2$CH$_3$ | —(CH$_2$)$_2$O(CH$_2$)$_2$— | —NHS(O)$_2$— |
| IX, X | —(CH$_2$)$_{14}$CH$_3$ | —CH$_2$OCH$_2$CH$_3$ | —(CH$_2$)$_2$O(CH$_2$)$_2$— | —NHS(O)$_2$— |
| VIII, IX, X | —(CH$_2$)$_{16}$CH$_3$ | —CH$_2$OCH$_2$CH$_3$ | —(CH$_2$)$_2$O(CH$_2$)$_2$— | —NHS(O)$_2$— |
| VIII, IX, X | —(CH$_2$)$_{18}$CH$_3$ | —CH$_2$OCH$_2$CH$_3$ | —(CH$_2$)$_2$O(CH$_2$)$_2$— | —NHS(O)$_2$— |
| IX, X | —(CH$_2$)$_7$CH═CH(CH$_2$)$_5$CH$_3$ | —CH$_2$OCH$_2$CH$_3$ | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | —CH$_2$OCH$_2$CH$_3$ | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | —CH$_2$OCH$_2$CH$_3$ | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | —CH$_2$OCH$_2$CH$_3$ | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | —CH$_2$OCH$_2$CH$_3$ | —(CH$_2$)$_2$O(CH$_2$)$_2$— | —NHS(O)$_2$— |
| IX, X | —(CH$_2$)$_{10}$CH$_3$ | —(CH$_2$)$_2$OCH$_3$ | —(CH$_2$)$_2$O(CH$_2$)$_2$— | —NHS(O)$_2$— |
| IX, X | —(CH$_2$)$_{12}$CH$_3$ | —(CH$_2$)$_2$OCH$_3$ | —(CH$_2$)$_2$O(CH$_2$)$_2$— | —NHS(O)$_2$— |
| IX, X | —(CH$_2$)$_{14}$CH$_3$ | —(CH$_2$)$_2$OCH$_3$ | —(CH$_2$)$_2$O(CH$_2$)$_2$— | —NHS(O)$_2$— |
| VIII, IX, X | —(CH$_2$)$_{16}$CH$_3$ | —(CH$_2$)$_2$OCH$_3$ | —(CH$_2$)$_2$O(CH$_2$)$_2$— | —NHS(O)$_2$— |
| VIII, IX, X | —(CH$_2$)$_{18}$CH$_3$ | —(CH$_2$)$_2$OCH$_3$ | —(CH$_2$)$_2$O(CH$_2$)$_2$— | —NHS(O)$_2$— |
| IX, X | —(CH$_2$)$_7$CH═CH(CH$_2$)$_5$CH$_3$ | —(CH$_2$)$_2$OCH$_3$ | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | —(CH$_2$)$_2$OCH$_3$ | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | —(CH$_2$)$_2$OCH$_3$ | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | —(CH$_2$)$_2$OCH$_3$ | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | —(CH$_2$)$_2$OCH$_3$ | —(CH$_2$)$_2$O(CH$_2$)$_2$— | —NHS(O)$_2$— |
| IX, X | —(CH$_2$)$_{10}$CH$_3$ | —(CH$_2$)$_3$CH$_3$ | —(CH$_2$)$_2$O(CH$_2$)$_2$— | —NHS(O)$_2$— |
| IX, X | —(CH$_2$)$_{12}$CH$_3$ | —(CH$_2$)$_3$CH$_3$ | —(CH$_2$)$_2$O(CH$_2$)$_2$— | —NHS(O)$_2$— |
| IX, X | —(CH$_2$)$_{14}$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_{16}$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_{18}$CH$_3$ | —(CH$_2$)$_3$CH$_3$ | —(CH$_2$)$_2$O(CH$_2$)$_2$— | —NHS(O)$_2$— |
| IX, X | —(CH$_2$)$_7$CH═CH(CH$_2$)$_5$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_7$CH═CH(CH$_2$)$_7$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_6$(CH$_2$CH═CH)$_2$(CH$_2$)$_4$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_6$(CH$_2$CH═CH)$_3$CH$_2$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_2$(CH$_2$CH═CH)$_4$(CH$_2$)$_4$CH$_3$ | —(CH$_2$)$_3$CH$_3$ | —(CH$_2$)$_2$O(CH$_2$)$_2$— | —NHS(O)$_2$— |
| VIII, IX, X | —(CH$_2$)$_{10}$CH$_3$ | H | —(CH$_2$)$_3$— | —NHC(O)NH— |
| VIII, IX, X | —(CH$_2$)$_{12}$CH$_3$ | H | —(CH$_2$)$_3$— | —NHC(O)NH— |
| VIII, IX, X | —(CH$_2$)$_{14}$CH$_3$ | H | —(CH$_2$)$_3$— | —NHC(O)NH— |
| VIII, IX, X | —(CH$_2$)$_{16}$CH$_3$ | H | —(CH$_2$)$_3$— | —NHC(O)NH— |
| VIII, IX, X | —(CH$_2$)$_{18}$CH$_3$ | H | —(CH$_2$)$_3$— | —NHC(O)NH— |
| VIII, IX, X | —(CH$_2$)$_7$CH═CH(CH$_2$)$_5$CH$_3$ | H | —(CH$_2$)$_3$— | —NHC(O)NH— |
| VIII, IX, X | —(CH$_2$)$_7$CH═CH(CH$_2$)$_7$CH$_3$ | H | —(CH$_2$)$_3$— | —NHC(O)NH— |
| VIII, IX, X | —(CH$_2$)$_6$(CH$_2$CH═CH)$_2$(CH$_2$)$_4$CH$_3$ | H | —(CH$_2$)$_3$— | —NHC(O)NH— |
| VIII, IX, X | —(CH$_2$)$_6$(CH$_2$CH═CH)$_3$CH$_2$CH$_3$ | H | —(CH$_2$)$_3$— | —NHC(O)NH— |
| VIII, IX, X | —(CH$_2$)$_2$(CH$_2$CH═CH)$_4$(CH$_2$)$_4$CH$_3$ | H | —(CH$_2$)$_3$— | —NHC(O)NH— |
| VIII, IX, X | —(CH$_2$)$_{10}$CH$_3$ | —CH$_3$ | —(CH$_2$)$_3$— | —NHC(O)NH— |
| VIII, IX, X | —(CH$_2$)$_{12}$CH$_3$ | —CH$_3$ | —(CH$_2$)$_3$— | —NHC(O)NH— |
| VIII, IX, X | —(CH$_2$)$_{14}$CH$_3$ | —CH$_3$ | —(CH$_2$)$_3$— | —NHC(O)NH— |
| VIII, IX, X | —(CH$_2$)$_{16}$CH$_3$ | —CH$_3$ | —(CH$_2$)$_3$— | —NHC(O)NH— |
| VIII, IX, X | —(CH$_2$)$_{18}$CH$_3$ | —CH$_3$ | —(CH$_2$)$_3$— | —NHC(O)NH— |
| VIII, IX, X | —(CH$_2$)$_7$CH═CH(CH$_2$)$_5$CH$_3$ | —CH$_3$ | —(CH$_2$)$_3$— | —NHC(O)NH— |
| VIII, IX, X | —(CH$_2$)$_7$CH═CH(CH$_2$)$_7$CH$_3$ | —CH$_3$ | —(CH$_2$)$_3$— | —NHC(O)NH— |
| VIII, IX, X | —(CH$_2$)$_6$(CH$_2$CH═CH)$_2$(CH$_2$)$_4$CH$_3$ | —CH$_3$ | —(CH$_2$)$_3$— | —NHC(O)NH— |
| VIII, IX, X | —(CH$_2$)$_6$(CH$_2$CH═CH)$_3$CH$_2$CH$_3$ | —CH$_3$ | —(CH$_2$)$_3$— | —NHC(O)NH— |
| VIII, IX, X | —(CH$_2$)$_2$(CH$_2$CH═CH)$_4$(CH$_2$)$_4$CH$_3$ | —CH$_3$ | —(CH$_2$)$_3$— | —NHC(O)NH— |
| VIII, IX, X | —(CH$_2$)$_{10}$CH$_3$ | —CH$_2$CH$_3$ | —(CH$_2$)$_3$— | —NHC(O)NH— |
| VIII, IX, X | —(CH$_2$)$_{12}$CH$_3$ | —CH$_2$CH$_3$ | —(CH$_2$)$_3$— | —NHC(O)NH— |
| VIII, IX, X | —(CH$_2$)$_{14}$CH$_3$ | —CH$_2$CH$_3$ | —(CH$_2$)$_3$— | —NHC(O)NH— |
| VIII, IX, X | —(CH$_2$)$_{16}$CH$_3$ | —CH$_2$CH$_3$ | —(CH$_2$)$_3$— | —NHC(O)NH— |
| VIII, IX, X | —(CH$_2$)$_{18}$CH$_3$ | —CH$_2$CH$_3$ | —(CH$_2$)$_3$— | —NHC(O)NH— |
| VIII, IX, X | —(CH$_2$)$_7$CH═CH(CH$_2$)$_5$CH$_3$ | —CH$_2$CH$_3$ | —(CH$_2$)$_3$— | —NHC(O)NH— |
| VIII, IX, X | —(CH$_2$)$_7$CH═CH(CH$_2$)$_7$CH$_3$ | —CH$_2$CH$_3$ | —(CH$_2$)$_3$— | —NHC(O)NH— |
| VIII, IX, X | —(CH$_2$)$_6$(CH$_2$CH═CH)$_2$(CH$_2$)$_4$CH$_3$ | —CH$_2$CH$_3$ | —(CH$_2$)$_3$— | —NHC(O)NH— |
| VIII, IX, X | —(CH$_2$)$_6$(CH$_2$CH═CH)$_3$CH$_2$CH$_3$ | —CH$_2$CH$_3$ | —(CH$_2$)$_3$— | —NHC(O)NH— |
| VIII, IX, X | —(CH$_2$)$_2$(CH$_2$CH═CH)$_4$(CH$_2$)$_4$CH$_3$ | —CH$_2$CH$_3$ | —(CH$_2$)$_3$— | —NHC(O)NH— |
| VIII, IX, X | —(CH$_2$)$_{10}$CH$_3$ | —(CH$_2$)$_2$CH$_3$ | —(CH$_2$)$_3$— | —NHC(O)NH— |
| VIII, IX, X | —(CH$_2$)$_{12}$CH$_3$ | —(CH$_2$)$_2$CH$_3$ | —(CH$_2$)$_3$— | —NHC(O)NH— |
| VIII, IX, X | —(CH$_2$)$_{14}$CH$_3$ | —(CH$_2$)$_2$CH$_3$ | —(CH$_2$)$_3$— | —NHC(O)NH— |
| VIII, IX, X | —(CH$_2$)$_{16}$CH$_3$ | —(CH$_2$)$_2$CH$_3$ | —(CH$_2$)$_3$— | —NHC(O)NH— |

-continued

| | | | | |
|---|---|---|---|---|
| VIII, IX, X | —(CH$_2$)$_{18}$CH$_3$ | —(CH$_2$)$_2$CH$_3$ | —(CH$_2$)$_3$— | —NHC(O)NH— |
| VIII, IX, X | —(CH$_2$)$_7$CH=CH(CH$_2$)$_5$CH$_3$ | —(CH$_2$)$_2$CH$_3$ | —(CH$_2$)$_3$— | —NHC(O)NH— |
| VIII, IX, X | —(CH$_2$)$_7$CH=CH(CH$_2$)$_7$CH$_3$ | —(CH$_2$)$_2$CH$_3$ | —(CH$_2$)$_3$— | —NHC(O)NH— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_3$— | —NHC(O)NH— |
| VIII, IX, X | —(CH$_2$)$_6$(CH$_2$CH=CH)$_3$CH$_2$CH$_3$ | —(CH$_2$)$_2$CH$_3$ | —(CH$_2$)$_3$— | —NHC(O)NH— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_3$— | —NHC(O)NH— |
| VIII, IX, X | —(CH$_2$)$_{10}$CH$_3$ | —CH$_2$OCH$_2$CH$_3$ | —(CH$_2$)$_3$— | —NHC(O)NH— |
| VIII, IX, X | —(CH$_2$)$_{12}$CH$_3$ | —CH$_2$OCH$_2$CH$_3$ | —(CH$_2$)$_3$— | —NHC(O)NH— |
| VIII, IX, X | —(CH$_2$)$_{14}$CH$_3$ | —CH$_2$OCH$_2$CH$_3$ | —(CH$_2$)$_3$— | —NHC(O)NH— |
| VIII, IX, X | —(CH$_2$)$_{16}$CH$_3$ | —CH$_2$OCH$_2$CH$_3$ | —(CH$_2$)$_3$— | —NHC(O)NH— |
| VIII, IX, X | —(CH$_2$)$_{18}$CH$_3$ | —CH$_2$OCH$_2$CH$_3$ | —(CH$_2$)$_3$— | —NHC(O)NH— |
| VIII, IX, X | —(CH$_2$)$_7$CH=CH(CH$_2$)$_5$CH$_3$ | —CH$_2$OCH$_2$CH$_3$ | —(CH$_2$)$_3$— | —NHC(O)NH— |
| VIII, IX, X | —(CH$_2$)$_7$CH=CH(CH$_2$)$_7$CH$_3$ | —CH$_2$OCH$_2$CH$_3$ | —(CH$_2$)$_3$— | —NHC(O)NH— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_3$— | —NHC(O)NH— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_3$— | —NHC(O)NH— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_3$— | —NHC(O)NH— |
| VIII, IX, X | —(CH$_2$)$_{10}$CH$_3$ | —(CH$_2$)$_2$OCH$_3$ | —(CH$_2$)$_3$— | —NHC(O)NH— |
| VIII, IX, X | —(CH$_2$)$_{12}$CH$_3$ | —(CH$_2$)$_2$OCH$_3$ | —(CH$_2$)$_3$— | —NHC(O)NH— |
| VIII, IX, X | —(CH$_2$)$_{14}$CH$_3$ | —(CH$_2$)$_2$OCH$_3$ | —(CH$_2$)$_3$— | —NHC(O)NH— |
| VIII, IX, X | —(CH$_2$)$_{16}$CH$_3$ | —(CH$_2$)$_2$OCH$_3$ | —(CH$_2$)$_3$— | —NHC(O)NH— |
| VIII, IX, X | —(CH$_2$)$_{18}$CH$_3$ | —(CH$_2$)$_2$OCH$_3$ | —(CH$_2$)$_3$— | —NHC(O)NH— |
| VIII, IX, X | —(CH$_2$)$_7$CH=CH(CH$_2$)$_5$CH$_3$ | —(CH$_2$)$_2$OCH$_3$ | —(CH$_2$)$_3$— | —NHC(O)NH— |
| VIII, IX, X | —(CH$_2$)$_7$CH=CH(CH$_2$)$_7$CH$_3$ | —(CH$_2$)$_2$OCH$_3$ | —(CH$_2$)$_3$— | —NHC(O)NH— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_3$— | —NHC(O)NH— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_3$— | —NHC(O)NH— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_3$— | —NHC(O)NH— |
| VIII, IX, X | —(CH$_2$)$_{10}$CH$_3$ | —(CH$_2$)$_3$CH$_3$ | —(CH$_2$)$_3$— | —NHC(O)NH— |
| VIII, IX, X | —(CH$_2$)$_{12}$CH$_3$ | —(CH$_2$)$_3$CH$_3$ | —(CH$_2$)$_3$— | —NHC(O)NH— |
| VIII, IX, X | —(CH$_2$)$_{14}$CH$_3$ | —(CH$_2$)$_3$CH$_3$ | —(CH$_2$)$_3$— | —NHC(O)NH— |
| VIII, IX, X | —(CH$_2$)$_{16}$CH$_3$ | —(CH$_2$)$_3$CH$_3$ | —(CH$_2$)$_3$— | —NHC(O)NH— |
| VIII, IX, X | —(CH$_2$)$_{18}$CH$_3$ | —(CH$_2$)$_3$CH$_3$ | —(CH$_2$)$_3$— | —NHC(O)NH— |
| VIII, IX, X | —(CH$_2$)$_7$CH=CH(CH$_2$)$_5$CH$_3$ | —(CH$_2$)$_3$CH$_3$ | —(CH$_2$)$_3$— | —NHC(O)NH— |
| VIII, IX, X | —(CH$_2$)$_7$CH=CH(CH$_2$)$_7$CH$_3$ | —(CH$_2$)$_3$CH$_3$ | —(CH$_2$)$_3$— | —NHC(O)NH— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_3$— | —NHC(O)NH— |
| VIII, IX, X | —(CH$_2$)$_6$(CH$_2$CH=CH)$_3$CH$_2$CH$_3$ | —(CH$_2$)$_3$CH$_3$ | —(CH$_2$)$_3$— | —NHC(O)NH— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_3$— | —NHC(O)NH— |
| VIII, IX, X | —(CH$_2$)$_{10}$CH$_3$ | H | —(CH$_2$)$_4$— | —NHC(O)NH— |
| VIII, IX, X | —(CH$_2$)$_{12}$CH$_3$ | H | —(CH$_2$)$_4$— | —NHC(O)NH— |
| VIII, IX, X | —(CH$_2$)$_{14}$CH$_3$ | H | —(CH$_2$)$_4$— | —NHC(O)NH— |
| VIII, IX, X | —(CH$_2$)$_{16}$CH$_3$ | H | —(CH$_2$)$_4$— | —NHC(O)NH— |
| VIII, IX, X | —(CH$_2$)$_{18}$CH$_3$ | H | —(CH$_2$)$_4$— | —NHC(O)NH— |
| VIII, IX, X | —(CH$_2$)$_7$CH=CH(CH$_2$)$_5$CH$_3$ | H | —(CH$_2$)$_4$— | —NHC(O)NH— |
| VIII, IX, X | —(CH$_2$)$_7$CH=CH(CH$_2$)$_7$CH$_3$ | H | —(CH$_2$)$_4$— | —NHC(O)NH— |
| VIII, IX, X | —(CH$_2$)$_6$(CH$_2$CH=CH)$_2$(CH$_2$)$_4$CH$_3$ | H | —(CH$_2$)$_4$— | —NHC(O)NH— |
| VIII, IX, X | —(CH$_2$)$_6$(CH$_2$CH=CH)$_3$CH$_2$CH$_3$ | H | —(CH$_2$)$_4$— | —NHC(O)NH— |
| VIII, IX, X | —(CH$_2$)$_2$(CH$_2$CH=CH)$_4$(CH$_2$)$_4$CH$_3$ | H | —(CH$_2$)$_4$— | —NHC(O)NH— |
| VIII, IX, X | —(CH$_2$)$_{10}$CH$_3$ | —CH$_3$ | —(CH$_2$)$_4$— | —NHC(O)NH— |
| VIII, IX, X | —(CH$_2$)$_{12}$CH$_3$ | —CH$_3$ | —(CH$_2$)$_4$— | —NHC(O)NH— |
| VIII, IX, X | —(CH$_2$)$_{14}$CH$_3$ | —CH$_3$ | —(CH$_2$)$_4$— | —NHC(O)NH— |
| VIII, IX, X | —(CH$_2$)$_{16}$CH$_3$ | —CH$_3$ | —(CH$_2$)$_4$— | —NHC(O)NH— |
| VIII, IX, X | —(CH$_2$)$_{18}$CH$_3$ | —CH$_3$ | —(CH$_2$)$_4$— | —NHC(O)NH— |
| VIII, IX, X | —(CH$_2$)$_7$CH=CH(CH$_2$)$_5$CH$_3$ | —CH$_3$ | —(CH$_2$)$_4$— | —NHC(O)NH— |
| VIII, IX, X | —(CH$_2$)$_7$CH=CH(CH$_2$)$_7$CH$_3$ | —CH$_3$ | —(CH$_2$)$_4$— | —NHC(O)NH— |
| VIII, IX, X | —(CH$_2$)$_6$(CH$_2$CH=CH)$_2$(CH$_2$)$_4$CH$_3$ | —CH$_3$ | —(CH$_2$)$_4$— | —NHC(O)NH— |
| VIII, IX, X | —(CH$_2$)$_6$(CH$_2$CH=CH)$_3$CH$_2$CH$_3$ | —CH$_3$ | —(CH$_2$)$_4$— | —NHC(O)NH— |
| VIII, IX, X | —(CH$_2$)$_2$(CH$_2$CH=CH)$_4$(CH$_2$)$_4$CH$_3$ | —CH$_3$ | —(CH$_2$)$_4$— | —NHC(O)NH— |
| VIII, IX, X | —(CH$_2$)$_{10}$CH$_3$ | —CH$_2$CH$_3$ | —(CH$_2$)$_4$— | —NHC(O)NH— |
| VIII, IX, X | —(CH$_2$)$_{12}$CH$_3$ | —CH$_2$CH$_3$ | —(CH$_2$)$_4$— | —NHC(O)NH— |
| VIII, IX, X | —(CH$_2$)$_{14}$CH$_3$ | —CH$_2$CH$_3$ | —(CH$_2$)$_4$— | —NHC(O)NH— |
| VIII, IX, X | —(CH$_2$)$_{16}$CH$_3$ | —CH$_2$CH$_3$ | —(CH$_2$)$_4$— | —NHC(O)NH— |
| VIII, IX, X | —(CH$_2$)$_{18}$CH$_3$ | —CH$_2$CH$_3$ | —(CH$_2$)$_4$— | —NHC(O)NH— |
| VIII, IX, X | —(CH$_2$)$_7$CH=CH(CH$_2$)$_5$CH$_3$ | —CH$_2$CH$_3$ | —(CH$_2$)$_4$— | —NHC(O)NH— |
| VIII, IX, X | —(CH$_2$)$_7$CH=CH(CH$_2$)$_7$CH$_3$ | —CH$_2$CH$_3$ | —(CH$_2$)$_4$— | —NHC(O)NH— |
| VIII, IX, X | —(CH$_2$)$_6$(CH$_2$CH=CH)$_2$(CH$_2$)$_4$CH$_3$ | —CH$_2$CH$_3$ | —(CH$_2$)$_4$— | —NHC(O)NH— |
| VIII, IX, X | —(CH$_2$)$_6$(CH$_2$CH=CH)$_3$CH$_2$CH$_3$ | —CH$_2$CH$_3$ | —(CH$_2$)$_4$— | —NHC(O)NH— |
| VIII, IX, X | —(CH$_2$)$_2$(CH$_2$CH=CH)$_4$(CH$_2$)$_4$CH$_3$ | —CH$_2$CH$_3$ | —(CH$_2$)$_4$— | —NHC(O)NH— |
| VIII, IX, X | —(CH$_2$)$_{10}$CH$_3$ | —(CH$_2$)$_2$CH$_3$ | —(CH$_2$)$_4$— | —NHC(O)NH— |
| VIII, IX, X | —(CH$_2$)$_{12}$CH$_3$ | —(CH$_2$)$_2$CH$_3$ | —(CH$_2$)$_4$— | —NHC(O)NH— |
| VIII, IX, X | —(CH$_2$)$_{14}$CH$_3$ | —(CH$_2$)$_2$CH$_3$ | —(CH$_2$)$_4$— | —NHC(O)NH— |
| VIII, IX, X | —(CH$_2$)$_{16}$CH$_3$ | —(CH$_2$)$_2$CH$_3$ | —(CH$_2$)$_4$— | —NHC(O)NH— |
| VIII, IX, X | —(CH$_2$)$_{18}$CH$_3$ | —(CH$_2$)$_2$CH$_3$ | —(CH$_2$)$_4$— | —NHC(O)NH— |
| VIII, IX, X | —(CH$_2$)$_7$CH=CH(CH$_2$)$_5$CH$_3$ | —(CH$_2$)$_2$CH$_3$ | —(CH$_2$)$_4$— | —NHC(O)NH— |
| VIII, IX, X | —(CH$_2$)$_7$CH=CH(CH$_2$)$_7$CH$_3$ | —(CH$_2$)$_2$CH$_3$ | —(CH$_2$)$_4$— | —NHC(O)NH— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_4$— | —NHC(O)NH— |
| VIII, IX, X | —(CH$_2$)$_6$(CH$_2$CH=CH)$_3$CH$_2$CH$_3$ | —(CH$_2$)$_2$CH$_3$ | —(CH$_2$)$_4$— | —NHC(O)NH— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_4$— | —NHC(O)NH— |
| VIII, IX, X | —(CH$_2$)$_{10}$CH$_3$ | —CH$_2$OCH$_2$CH$_3$ | —(CH$_2$)$_4$— | —NHC(O)NH— |
| VIII, IX, X | —(CH$_2$)$_{12}$CH$_3$ | —CH$_2$OCH$_2$CH$_3$ | —(CH$_2$)$_4$— | —NHC(O)NH— |
| VIII, IX, X | —(CH$_2$)$_{14}$CH$_3$ | —CH$_2$OCH$_2$CH$_3$ | —(CH$_2$)$_4$— | —NHC(O)NH— |

-continued

| | | | | |
|---|---|---|---|---|
| VIII, IX, X | —(CH$_2$)$_{16}$CH$_3$ | —CH$_2$OCH$_2$CH$_3$ | —(CH$_2$)$_4$— | —NHC(O)NH— |
| VIII, IX, X | —(CH$_2$)$_{18}$CH$_3$ | —CH$_2$OCH$_2$CH$_3$ | —(CH$_2$)$_4$— | —NHC(O)NH— |
| VIII, IX, X | —(CH$_2$)$_7$CH=CH(CH$_2$)$_5$CH$_3$ | —CH$_2$OCH$_2$CH$_3$ | —(CH$_2$)$_4$— | —NHC(O)NH— |
| VIII, IX, X | —(CH$_2$)$_7$CH=CH(CH$_2$)$_7$CH$_3$ | —CH$_2$OCH$_2$CH$_3$ | —(CH$_2$)$_4$— | —NHC(O)NH— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_4$— | —NHC(O)NH— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_4$— | —NHC(O)NH— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_4$— | —NHC(O)NH— |
| VIII, IX, X | —(CH$_2$)$_{10}$CH$_3$ | —(CH$_2$)$_2$OCH$_3$ | —(CH$_2$)$_4$— | —NHC(O)NH— |
| VIII, IX, X | —(CH$_2$)$_{12}$CH$_3$ | —(CH$_2$)$_2$OCH$_3$ | —(CH$_2$)$_4$— | —NHC(O)NH— |
| VIII, IX, X | —(CH$_2$)$_{14}$CH$_3$ | —(CH$_2$)$_2$OCH$_3$ | —(CH$_2$)$_4$— | —NHC(O)NH— |
| VIII, IX, X | —(CH$_2$)$_{16}$CH$_3$ | —(CH$_2$)$_2$OCH$_3$ | —(CH$_2$)$_4$— | —NHC(O)NH— |
| VIII, IX, X | —(CH$_2$)$_{18}$CH$_3$ | —(CH$_2$)$_2$OCH$_3$ | —(CH$_2$)$_4$— | —NHC(O)NH— |
| VIII, IX, X | —(CH$_2$)$_7$CH=CH(CH$_2$)$_5$CH$_3$ | —(CH$_2$)$_2$OCH$_3$ | —(CH$_2$)$_4$— | —NHC(O)NH— |
| VIII, IX, X | —(CH$_2$)$_7$CH=CH(CH$_2$)$_7$CH$_3$ | —(CH$_2$)$_2$OCH$_3$ | —(CH$_2$)$_4$— | —NHC(O)NH— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_4$— | —NHC(O)NH— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_5$— | —NHC(O)NH— |
| VIII, IX, X | —(CH$_2$)$_{10}$CH$_3$ | —(CH$_2$)$_3$CH$_3$ | —(CH$_2$)$_4$— | —NHC(O)— |
| VIII, IX, X | —(CH$_2$)$_{12}$CH$_3$ | —(CH$_2$)$_3$CH$_3$ | —(CH$_2$)$_4$— | —NHC(O)— |
| VIII, IX, X | —(CH$_2$)$_{14}$CH$_3$ | —(CH$_2$)$_3$CH$_3$ | —(CH$_2$)$_4$— | —NHC(O)— |
| VIII, IX, X | —(CH$_2$)$_{16}$CH$_3$ | —(CH$_2$)$_3$CH$_3$ | —(CH$_2$)$_4$— | —NHC(O)— |
| VIII, IX, X | —(CH$_2$)$_{18}$CH$_3$ | —(CH$_2$)$_3$CH$_3$ | —(CH$_2$)$_4$— | —NHC(O)— |
| VIII, IX, X | —(CH$_2$)$_7$CH=CH(CH$_2$)$_5$CH$_3$ | —(CH$_2$)$_3$CH$_3$ | —(CH$_2$)$_4$— | —NHC(O)— |
| VIII, IX, X | —(CH$_2$)$_7$CH=CH(CH$_2$)$_7$CH$_3$ | —(CH$_2$)$_3$CH$_3$ | —(CH$_2$)$_4$— | —NHC(O)— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_4$— | —NHC(O)— |
| VIII, IX, X | —(CH$_2$)$_6$(CH$_2$CH=CH)$_3$CH$_2$CH$_3$ | —(CH$_2$)$_3$CH$_3$ | —(CH$_2$)$_4$— | —NHC(O)— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_4$— | —NHC(O)— |
| VIII, IX, X | —(CH$_2$)$_{10}$CH$_3$ | H | —(CH$_2$)$_5$— | —NHC(O)NH— |
| VIII, IX, X | —(CH$_2$)$_{12}$CH$_3$ | H | —(CH$_2$)$_5$— | —NHC(O)NH— |
| VIII, IX, X | —(CH$_2$)$_{14}$CH$_3$ | H | —(CH$_2$)$_5$— | —NHC(O)NH— |
| VIII, IX, X | —(CH$_2$)$_{16}$CH$_3$ | H | —(CH$_2$)$_5$— | —NHC(O)NH— |
| VIII, IX, X | —(CH$_2$)$_{18}$CH$_3$ | H | —(CH$_2$)$_5$— | —NHC(O)NH— |
| VIII, IX, X | —(CH$_2$)$_7$CH=CH(CH$_2$)$_5$CH$_3$ | H | —(CH$_2$)$_5$— | —NHC(O)NH— |
| VIII, IX, X | —(CH$_2$)$_7$CH=CH(CH$_2$)$_7$CH$_3$ | H | —(CH$_2$)$_5$— | —NHC(O)NH— |
| VIII, IX, X | —(CH$_2$)$_6$(CH$_2$CH=CH)$_2$(CH$_2$)$_4$CH$_3$ | H | —(CH$_2$)$_5$— | —NHC(O)NH— |
| VIII, IX, X | —(CH$_2$)$_6$(CH$_2$CH=CH)$_3$CH$_2$CH$_3$ | H | —(CH$_2$)$_5$— | —NHC(O)NH— |
| VIII, IX, X | —(CH$_2$)$_2$(CH$_2$CH=CH)$_4$(CH$_2$)$_4$CH$_3$ | H | —(CH$_2$)$_5$— | —NHC(O)NH— |
| VIII, IX, X | —(CH$_2$)$_{10}$CH$_3$ | —CH$_3$ | —(CH$_2$)$_5$— | —NHC(O)NH— |
| VIII, IX, X | —(CH$_2$)$_{12}$CH$_3$ | —CH$_3$ | —(CH$_2$)$_5$— | —NHC(O)NH— |
| VIII, IX, X | —(CH$_2$)$_{14}$CH$_3$ | —CH$_3$ | —(CH$_2$)$_5$— | —NHC(O)NH— |
| VIII, IX, X | —(CH$_2$)$_{16}$CH$_3$ | —CH$_3$ | —(CH$_2$)$_5$— | —NHC(O)NH— |
| VIII, IX, X | —(CH$_2$)$_{18}$CH$_3$ | —CH$_3$ | —(CH$_2$)$_5$— | —NHC(O)NH— |
| VIII, IX, X | —(CH$_2$)$_7$CH=CH(CH$_2$)$_5$CH$_3$ | —CH$_3$ | —(CH$_2$)$_5$— | —NHC(O)NH— |
| VIII, IX, X | —(CH$_2$)$_7$CH=CH(CH$_2$)$_7$CH$_3$ | —CH$_3$ | —(CH$_2$)$_5$— | —NHC(O)NH— |
| VIII, IX, X | —(CH$_2$)$_6$(CH$_2$CH=CH)$_2$(CH$_2$)$_4$CH$_3$ | —CH$_3$ | —(CH$_2$)$_5$— | —NHC(O)NH— |
| VIII, IX, X | —(CH$_2$)$_6$(CH$_2$CH=CH)$_3$CH$_2$CH$_3$ | —CH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —CH$_3$ | —(CH$_2$)$_5$— | —NHC(O)NH— |
| VIII, IX, X | —(CH$_2$)$_{10}$CH$_3$ | —CH$_2$CH$_3$ | —(CH$_2$)$_5$— | —NHC(O)NH— |
| VIII, IX, X | —(CH$_2$)$_{12}$CH$_3$ | —CH$_2$CH$_3$ | —(CH$_2$)$_5$— | —NHC(O)NH— |
| VIII, IX, X | —(CH$_2$)$_{14}$CH$_3$ | —CH$_2$CH$_3$ | —(CH$_2$)$_5$— | —NHC(O)NH— |
| VIII, IX, X | —(CH$_2$)$_{16}$CH$_3$ | —CH$_2$CH$_3$ | —(CH$_2$)$_5$— | —NHC(O)NH— |
| VIII, IX, X | —(CH$_2$)$_{18}$CH$_3$ | —CH$_2$CH$_3$ | —(CH$_2$)$_5$— | —NHC(O)NH— |
| VIII, IX, X | —(CH$_2$)$_7$CH=CH(CH$_2$)$_5$CH$_3$ | —CH$_2$CH$_3$ | —(CH$_2$)$_5$— | —NHC(O)NH— |
| VIII, IX, X | —(CH$_2$)$_7$CH=CH(CH$_2$)$_7$CH$_3$ | —CH$_2$CH$_3$ | —(CH$_2$)$_5$— | —NHC(O)NH— |
| VIII, IX, X | —(CH$_2$)$_6$(CH$_2$CH=CH)$_2$(CH$_2$)$_4$CH$_3$ | —CH$_2$CH$_3$ | —(CH$_2$)$_5$— | —NHC(O)NH— |
| VIII, IX, X | —(CH$_2$)$_6$(CH$_2$CH=CH)$_3$CH$_2$CH$_3$ | —CH$_2$CH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —CH$_2$CH$_3$ | —(CH$_2$)$_5$— | —NHC(O)NH— |
| VIII, IX, X | —(CH$_2$)$_{10}$CH$_3$ | —(CH$_2$)$_2$CH$_3$ | —(CH$_2$)$_5$— | —NHC(O)NH— |
| VIII, IX, X | —(CH$_2$)$_{12}$CH$_3$ | —(CH$_2$)$_2$CH$_3$ | —(CH$_2$)$_5$— | —NHC(O)NH— |
| VIII, IX, X | —(CH$_2$)$_{14}$CH$_3$ | —(CH$_2$)$_2$CH$_3$ | —(CH$_2$)$_5$— | —NHC(O)NH— |
| VIII, IX, X | —(CH$_2$)$_{16}$CH$_3$ | —(CH$_2$)$_2$CH$_3$ | —(CH$_2$)$_5$— | —NHC(O)NH— |
| VIII, IX, X | —(CH$_2$)$_{18}$CH$_3$ | —(CH$_2$)$_2$CH$_3$ | —(CH$_2$)$_5$— | —NHC(O)NH— |
| VIII, IX, X | —(CH$_2$)$_7$CH=CH(CH$_2$)$_5$CH$_3$ | —(CH$_2$)$_2$CH$_3$ | —(CH$_2$)$_5$— | —NHC(O)NH— |
| VIII, IX, X | —(CH$_2$)$_7$CH=CH(CH$_2$)$_7$CH$_3$ | —(CH$_2$)$_2$CH$_3$ | —(CH$_2$)$_5$— | —NHC(O)NH— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_5$— | —NHC(O)NH— |
| VIII, IX, X | —(CH$_2$)$_6$(CH$_2$CH=CH)$_3$CH$_2$CH$_3$ | —(CH$_2$)$_2$CH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_5$— | —NHC(O)NH— |
| VIII, IX, X | —(CH$_2$)$_{10}$CH$_3$ | —CH$_2$OCH$_2$CH$_3$ | —(CH$_2$)$_5$— | —NHC(O)NH— |
| VIII, IX, X | —(CH$_2$)$_{12}$CH$_3$ | —CH$_2$OCH$_2$CH$_3$ | —(CH$_2$)$_5$— | —NHC(O)NH— |
| VIII, IX, X | —(CH$_2$)$_{14}$CH$_3$ | —CH$_2$OCH$_2$CH$_3$ | —(CH$_2$)$_5$— | —NHC(O)NH— |
| VIII, IX, X | —(CH$_2$)$_{16}$CH$_3$ | —CH$_2$OCH$_2$CH$_3$ | —(CH$_2$)$_5$— | —NHC(O)NH— |
| VIII, IX, X | —(CH$_2$)$_{18}$CH$_3$ | —CH$_2$OCH$_2$CH$_3$ | —(CH$_2$)$_5$— | —NHC(O)NH— |
| VIII, IX, X | —(CH$_2$)$_7$CH=CH(CH$_2$)$_5$CH$_3$ | —CH$_2$OCH$_2$CH$_3$ | —(CH$_2$)$_5$— | —NHC(O)NH— |
| VIII, IX, X | —(CH$_2$)$_7$CH=CH(CH$_2$)$_7$CH$_3$ | —CH$_2$OCH$_2$CH$_3$ | —(CH$_2$)$_5$— | —NHC(O)NH— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_5$— | —NHC(O)NH— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_5$— | —NHC(O)NH— |
| VIII, IX, X | —(CH$_2$)$_{10}$CH$_3$ | —(CH$_2$)$_2$OCH$_3$ | —(CH$_2$)$_5$— | —NHC(O)NH— |
| VIII, IX, X | —(CH$_2$)$_{12}$CH$_3$ | —(CH$_2$)$_2$OCH$_3$ | —(CH$_2$)$_5$— | —NHC(O)NH— |

-continued

| | | | | |
|---|---|---|---|---|
| VIII, IX, X | —(CH$_2$)$_{14}$CH$_3$ | —(CH$_2$)$_2$OCH$_3$ | —(CH$_2$)$_5$— | —NHC(O)NH— |
| VIII, IX, X | —(CH$_2$)$_{16}$CH$_3$ | —(CH$_2$)$_2$OCH$_3$ | —(CH$_2$)$_5$— | —NHC(O)NH— |
| VIII, IX, X | —(CH$_2$)$_{18}$CH$_3$ | —(CH$_2$)$_2$OCH$_3$ | —(CH$_2$)$_5$— | —NHC(O)NH— |
| VIII, IX, X | —(CH$_2$)$_7$CH=CH(CH$_2$)$_5$CH$_3$ | —(CH$_2$)$_2$OCH$_3$ | —(CH$_2$)$_5$— | —NHC(O)NH— |
| VIII, IX, X | —(CH$_2$)$_7$CH=CH(CH$_2$)$_7$CH$_3$ | —(CH$_2$)$_2$OCH$_3$ | —(CH$_2$)$_5$— | —NHC(O)NH— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_5$— | —NHC(O)NH— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_5$— | —NHC(O)NH— |
| VIII, IX, X | —(CH$_2$)$_{10}$CH$_3$ | —(CH$_2$)$_3$CH$_3$ | —(CH$_2$)$_5$— | —NHC(O)NH— |
| VIII, IX, X | —(CH$_2$)$_{12}$CH$_3$ | —(CH$_2$)$_3$CH$_3$ | —(CH$_2$)$_5$— | —NHC(O)NH— |
| VIII, IX, X | —(CH$_2$)$_{14}$CH$_3$ | —(CH$_2$)$_3$CH$_3$ | —(CH$_2$)$_5$— | —NHC(O)NH— |
| VIII, IX, X | —(CH$_2$)$_{16}$CH$_3$ | —(CH$_2$)$_3$CH$_3$ | —(CH$_2$)$_5$— | —NHC(O)NH— |
| VIII, IX, X | —(CH$_2$)$_{18}$CH$_3$ | —(CH$_2$)$_3$CH$_3$ | —(CH$_2$)$_5$— | —NHC(O)NH— |
| VIII, IX, X | —(CH$_2$)$_7$CH=CH(CH$_2$)$_5$CH$_3$ | —(CH$_2$)$_3$CH$_3$ | —(CH$_2$)$_5$— | —NHC(O)NH— |
| VIII, IX, X | —(CH$_2$)$_7$CH=CH(CH$_2$)$_7$CH$_3$ | —(CH$_2$)$_3$CH$_3$ | —(CH$_2$)$_5$— | —NHC(O)NH— |
| VIII, IX, X | —(CH$_2$)$_6$(CH$_2$CH=CH)$_2$(CH$_2$)$_4$CH$_3$ | —(CH$_2$)$_3$CH$_3$ | —(CH$_2$)$_5$— | —NHC(O)NH— |
| VIII, IX, X | —(CH$_2$)$_6$(CH$_2$CH=CH)$_3$CH$_2$CH$_3$ | —(CH$_2$)$_3$CH$_3$ | —(CH$_2$)$_5$— | —NHC(O)NH— |
| VIII, IX, X | —(CH$_2$)$_2$(CH$_2$CH=CH)$_4$(CH$_2$)$_4$CH$_3$ | —(CH$_2$)$_3$CH$_3$ | —(CH$_2$)$_5$— | —NHC(O)NH— |
| VIII, IX, X | —(CH$_2$)$_{10}$CH$_3$ | H | —(CH$_2$)$_2$O(CH$_2$)$_2$— | —NHC(O)NH— |
| VIII, IX, X | —(CH$_2$)$_{12}$CH$_3$ | H | —(CH$_2$)$_2$O(CH$_2$)$_2$— | —NHC(O)NH— |
| VIII, IX, X | —(CH$_2$)$_{14}$CH$_3$ | H | —(CH$_2$)$_2$O(CH$_2$)$_2$— | —NHC(O)NH— |
| VIII, IX, X | —(CH$_2$)$_{16}$CH$_3$ | H | —(CH$_2$)$_2$O(CH$_2$)$_2$— | —NHC(O)NH— |
| VIII, IX, X | —(CH$_2$)$_{18}$CH$_3$ | H | —(CH$_2$)$_2$O(CH$_2$)$_2$— | —NHC(O)N— |
| VIII, IX, X | —(CH$_2$)$_7$CH=CH(CH$_2$)$_5$CH$_3$ | H | —(CH$_2$)$_2$O(CH$_2$)$_2$— | —NHC(O)NH— |
| VIII, IX, X | —(CH$_2$)$_7$CH=CH(CH$_2$)$_7$CH$_3$ | H | —(CH$_2$)$_2$O(CH$_2$)$_2$— | —NHC(O)NH— |
| VIII, IX, X | —(CH$_2$)$_6$(CH$_2$CH=CH)$_2$(CH$_2$)$_4$CH$_3$ | H | —(CH$_2$)$_2$O(CH$_2$)$_2$— | —NHC(O)NH— |
| VIII, IX, X | —(CH$_2$)$_6$(CH$_2$CH=CH)$_3$CH$_2$CH$_3$ | H | —(CH$_2$)$_2$O(CH$_2$)$_2$— | —NHC(O)NH— |
| VIII, IX, X | —(CH$_2$)$_2$(CH$_2$CH=CH)$_4$(CH$_2$)$_4$CH$_3$ | H | —(CH$_2$)$_2$O(CH$_2$)$_2$— | —NHC(O)NH— |
| VIII, IX, X | —(CH$_2$)$_{10}$CH$_3$ | —CH$_3$ | —(CH$_2$)$_2$O(CH$_2$)$_2$— | —NHC(O)NH— |
| VIII, IX, X | —(CH$_2$)$_{12}$CH$_3$ | —CH$_3$ | —(CH$_2$)$_2$O(CH$_2$)$_2$— | —NHC(O)NH— |
| VIII, IX, X | —(CH$_2$)$_{14}$CH$_3$ | —CH$_3$ | —(CH$_2$)$_2$O(CH$_2$)$_2$— | —NHC(O)NH— |
| VIII, IX, X | —(CH$_2$)$_{16}$CH$_3$ | —CH$_3$ | —(CH$_2$)$_2$O(CH$_2$)$_2$— | —NHC(O)NH— |
| VIII, IX, X | —(CH$_2$)$_{18}$CH$_3$ | —CH$_3$ | —(CH$_2$)$_2$O(CH$_2$)$_2$— | —NHC(O)NH— |
| VIII, IX, X | —(CH$_2$)$_7$CH=CH(CH$_2$)$_5$CH$_3$ | —CH$_3$ | —(CH$_2$)$_2$O(CH$_2$)$_2$— | —NHC(O)NH— |
| VIII, IX, X | —(CH$_2$)$_7$CH=CH(CH$_2$)$_7$CH$_3$ | —CH$_3$ | —(CH$_2$)$_2$O(CH$_2$)$_2$— | —NHC(O)NH— |
| VIII, IX, X | —(CH$_2$)$_6$(CH$_2$CH=CH)$_2$(CH$_2$)$_4$CH$_3$ | —CH$_3$ | —(CH$_2$)$_2$O(CH$_2$)$_2$— | —NHC(O)NH— |
| VIII, IX, X | —(CH$_2$)$_6$(CH$_2$CH=CH)$_3$CH$_2$CH$_3$ | —CH$_3$ | —(CH$_2$)$_2$O(CH$_2$)$_2$— | —NHC(O)NH— |
| VIII, IX, X | —(CH$_2$)$_2$(CH$_2$CH=CH)$_4$(CH$_2$)$_4$CH$_3$ | —CH$_3$ | —(CH$_2$)$_2$O(CH$_2$)$_2$— | —NHC(O)NH— |
| VIII, IX, X | —(CH$_2$)$_{10}$CH$_3$ | —CH$_2$CH$_3$ | —(CH$_2$)$_2$O(CH$_2$)$_2$— | —NHC(O)NH— |
| VIII, IX, X | —(CH$_2$)$_{12}$CH$_3$ | —CH$_2$CH$_3$ | —(CH$_2$)$_2$O(CH$_2$)$_2$— | —NHC(O)NH— |
| VIII, IX, X | —(CH$_2$)$_{14}$CH$_3$ | —CH$_2$CH$_3$ | —(CH$_2$)$_2$O(CH$_2$)$_2$— | —NHC(O)NH— |
| VIII, IX, X | —(CH$_2$)$_{16}$CH$_3$ | —CH$_2$CH$_3$ | —(CH$_2$)$_2$O(CH$_2$)$_2$— | —NHC(O)NH— |
| VIII, IX, X | —(CH$_2$)$_{18}$CH$_3$ | —CH$_2$CH$_3$ | —(CH$_2$)$_2$O(CH$_2$)$_2$— | —NHC(O)NH— |
| VIII, IX, X | —(CH$_2$)$_7$CH=CH(CH$_2$)$_5$CH$_3$ | —CH$_2$CH$_3$ | —(CH$_2$)$_2$O(CH$_2$)$_2$— | —NHC(O)NH— |
| VIII, IX, X | —(CH$_2$)$_7$CH=CH(CH$_2$)$_7$CH$_3$ | —CH$_2$CH$_3$ | —(CH$_2$)$_2$O(CH$_2$)$_2$— | —NHC(O)NH— |
| VIII, IX, X | —(CH$_2$)$_6$(CH$_2$CH=CH)$_2$(CH$_2$)$_4$CH$_3$ | —CH$_2$CH$_3$ | —(CH$_2$)$_2$O(CH$_2$)$_2$— | —NHC(O)NH— |
| VIII, IX, X | —(CH$_2$)$_6$(CH$_2$CH=CH)$_3$CH$_2$CH$_3$ | —CH$_2$CH$_3$ | —(CH$_2$)$_2$O(CH$_2$)$_2$— | —NHC(O)NH— |
| VIII, IX, X | —(CH$_2$)$_2$(CH$_2$CH=CH)$_4$(CH$_2$)$_4$CH$_3$ | —CH$_2$CH$_3$ | —(CH$_2$)$_2$O(CH$_2$)$_2$— | —NHC(O)NH— |
| VIII, IX, X | —(CH$_2$)$_{10}$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_{12}$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_{14}$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_{16}$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_{18}$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_7$CH=CH(CH$_2$)$_5$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_7$CH=CH(CH$_2$)$_7$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_6$(CH$_2$CH=CH)$_2$(CH$_2$)$_4$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_6$(CH$_2$CH=CH)$_3$CH$_2$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_2$(CH$_2$CH=CH)$_4$(CH$_2$)$_4$CH$_3$ | —(CH$_2$)$_2$CH$_3$ | —(CH$_2$)$_2$O(CH$_2$)$_2$— | —NHC(O)NH— |
| VIII, IX, X | —(CH$_2$)$_{10}$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_{12}$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_{14}$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_{16}$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_{18}$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_7$CH=CH(CH$_2$)$_5$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_7$CH=CH(CH$_2$)$_7$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_6$(CH$_2$CH=CH)$_2$(CH$_2$)$_4$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_6$(CH$_2$CH=CH)$_3$CH$_2$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_2$(CH$_2$CH=CH)$_4$(CH$_2$)$_4$CH$_3$ | —CH$_2$OCH$_2$CH$_3$ | —(CH$_2$)$_2$O(CH$_2$)$_2$— | —NHC(O)NH— |
| VIII, IX, X | —(CH$_2$)$_{10}$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_{12}$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_{14}$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_{16}$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_{18}$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_7$CH=CH(CH$_2$)$_5$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_7$CH=CH(CH$_2$)$_7$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_6$(CH$_2$CH=CH)$_2$(CH$_2$)$_4$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_6$(CH$_2$CH=CH)$_3$CH$_2$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_2$(CH$_2$CH=CH)$_4$(CH$_2$)$_4$CH$_3$ | —(CH$_2$)$_2$OCH$_3$ | —(CH$_2$)$_2$O(CH$_2$)$_2$— | —NHC(O)NH— |
| VIII, IX, X | —(CH$_2$)$_{10}$CH$_3$ | —(CH$_2$)$_3$CH$_3$ | —(CH$_2$)$_2$O(CH$_2$)$_2$— | —NHC(O)NH— |

-continued

| | | | | |
|---|---|---|---|---|
| VIII, IX, X | —(CH$_2$)$_{12}$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_{14}$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_{16}$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_{18}$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_7$CH=CH(CH$_2$)$_5$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_7$CH=CH(CH$_2$)$_7$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_6$(CH$_2$CH=CH)$_2$(CH$_2$)$_4$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_6$(CH$_2$CH=CH)$_3$CH$_2$CH$_3$ | | —(CH$_2$)$_3$CH$_3$ | —(CH$_2$)$_2$O(CH$_2$)$_2$— —NHC(O)NH— |
| VIII, IX, X | —(CH$_2$)$_2$(CH$_2$CH=CH)$_4$(CH$_2$)$_4$CH$_3$ | —(CH$_2$)$_3$CH$_3$ | | —(CH$_2$)$_2$O(CH$_2$)$_2$— —NHC(O)NH— |

Example 5

Immunizations

C57BL/6 mice were immunized with conjugate (1 mg ovalbumin and 200 μg MK in 200 μl phosphate buffered saline (PBS) either subcutaneously or intraperitoneally. Control mice were immunized with 1 mg ovalbumin in 200 μl PBS. For analysis of primary responses, mice were sacrificed 5-7 days after immunization. For analysis of secondary responses, the mice were boosted 7-15 days after the initial immunization and sacrificed 5-7 days later. Unless otherwise indicated, lymph nodes were harvested from mice immunized subcutaneously for analysis and spleen cells were harvested from mice immunized intraperitoneally for analysis.

A stock IRM solution of N-(2-{2-[4-amino-2-(2-methoxyethyl)-1H-imidazo[4,5-c]quinolin-1-yl]ethoxy}ethyl)hexadecanamide was prepared by dissolving it in DMSO to a concentration of 10 mg/ml. Ovalbumin was dissolved in PBS to a concentration of 50 mg/ml. Fifty μl of the stock IRM solution was added to 150 μl of PBS and then mixed by vortexing. Fifty μl of the ovalbumin was added to the stock IRM solution and mixed by vortexing. A cloudy colloidal suspension of IRM and ovalbumin resulted.

Figure 2:
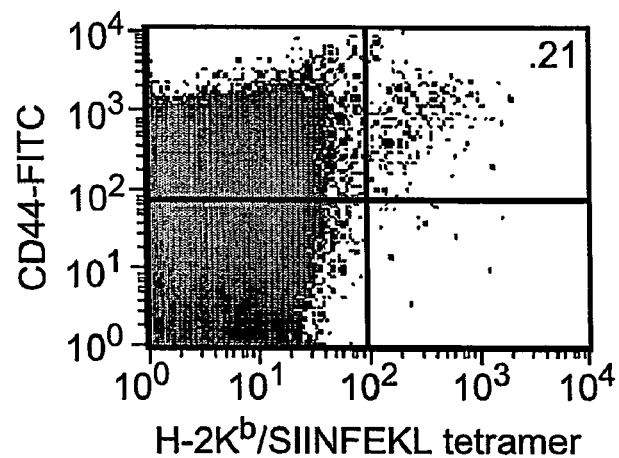
FIG. 2 shows expansion of antigen-specific $CD8^+$ T cells in one subject after immunization with a colloidal suspension of IRM and ovalbumin, as described in Example 5.
Figure 3:
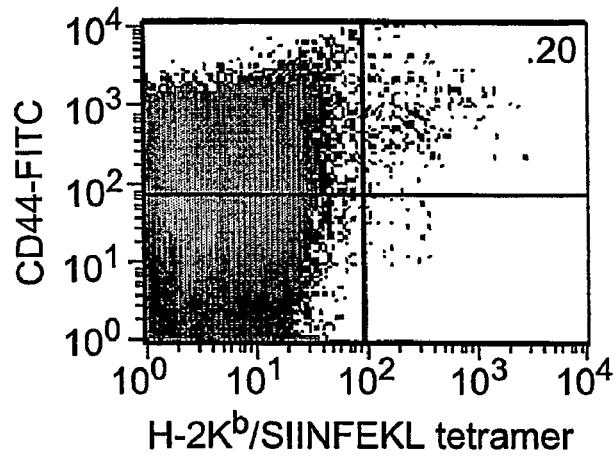
FIG. 3 shows expansion of antigen-specific $CD8^+$ T cells in a second subject after immunization with a colloidal suspension of IRM and ovalbumin, as described in Example 5.

Mice were immunized on Day 0 subcutaneously as described above with either (a) ovalbumin alone, or (b) 50 μl of the colloidal suspension of ovalbumin and the IRM. On Day 6, draining lymph nodes were removed, homogenized, and stained with the H-2K$^b$/SIINFEKL tetramer to identify ovalbumin-specific T cells. FIG. 1 shows flow cytometry data from a control mouse immunized with ovalbumin alone; FIGS. 2 and 3 show data from two different mice that were immunized with the colloidal suspension.

Reagents

Ovalbumin was obtained from Sigma Chemical Company (St. Louis, Mo.). Tetramers of the MHC class I molecule H-2K$^b$ bound to the dominant ovalbumin peptide SIINFEKL were produced as described in Kedl et al., *J Exp Med*, 192: 1105-13 (2000).

Compounds of the invention were found to induce, and certain compounds may inhibit, cytokine biosynthesis when tested using the methods described below. The compounds of Examples 1-4 induced both interferon and tumor necrosis factor when tested using the "Cytokine Induction in Human Cells" assay described below.

Cytokine Induction in Human Cells

An in vitro human blood cell system is used to assess cytokine induction. Activity is based on the measurement of interferon-α and tumor necrosis factor-α (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10$^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 micromolar (μM).

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is 2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30° C. to −70° C. until analysis. The samples are analyzed for IFN-α by ELISA and for TNF-α by ELISA or IGEN Assay.

IFN-α and TNF-α Analysis by ELISA

IFN-α concentration is determined by ELISA using a Human Multi-Species kit from PBL Biomedical Laboratories, New Brunswick, N.J. Results are expressed in pg/mL.

TNF-α concentration is determined using ELISA kits available from Biosource International, Camarillo, Calif. Alternately, the TNF-α concentration can be determined by ORIGEN M-Series Immunoassay and read on an IGEN M-8 analyzer from IGEN International, Gaithersburg, Md. The immunoassay uses a human TNF-α capture and detection antibody pair from Biosource International, Camarillo, Calif. Results are expressed in pg/in L.

Cytokine Inhibition in Mouse Cells

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 μL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration approximately 10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. The present invention has been described with reference to several embodiments thereof. The foregoing illustrative embodiments and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention is intended to be limited only by the claims that follow.

What is claimed is:

1. A compound of the following Formula I:

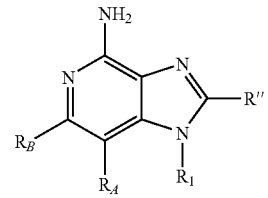

wherein:
R₁ has the formula alkylene-L-$R_{1-1}$, alkenylene-L-$R_{1-1}$, or alkynylene-L-$R_{1-1}$, wherein:
the alkylene, alkenylene, and alkynylene groups are optionally interrupted with one or more —O— groups;
L is a bond or a functional linking group selected from the group consisting of —NH—S(O)₂—, —NH—C(O)—, —NH—C(S)—, —NH—S(O)₂—NR₃—, —NH—C(O)—NR₃—, —NH—C(S)—NR₃—, —NH—C(O)—O—, —O—, —S—, and —S(O)₂—; and
$R_{1-1}$ is a linear or branched aliphatic group having at least 11 carbon atoms, optionally including one or more unsaturated carbon-carbon bonds;
R″ is selected from the group consisting of:
hydrogen;
alkyl;
alkenyl;
aryl;
heteroaryl;
heterocyclyl;
alkylene-Y-alkyl;
alkylene-Y-alkenyl;
alkylene-Y-aryl; and
alkyl or alkenyl substituted by one or more substituents selected from the group consisting of:
—OH;
halogen;
—N(R₄)₂;

—C(O)—C$_{1-10}$alkyl;
—C(O)—O—C$_{1-10}$alkyl;
—N$_3$;
aryl;
heteroaryl;
heterocyclyl;
—C(O)-aryl; and
—C(O)-heteroaryl;
wherein aryl is phenyl, naphthyl, biphenyl, fluorenyl or indenyl; heteroaryl is furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, or 1-oxidopyridyl; and heterocyclyl is the fully saturated or partially unsaturated derivative of any one of the above heteroaryl groups, pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, or homopiperidinyl;

wherein: Y is —O— or —S(O)$_{0-2}$—; and each R$_4$ is independently selected from the group consisting of hydrogen, C$_{1-10}$alkyl, and C$_{2-10}$alkenyl;

R$_A$ and R$_B$ are taken together to form a fused benzene ring or a fused 5- to 7-membered saturated ring not containing a heteroatom, and unsubstituted or substituted by one or more R groups;

each R is independently selected from the group consisting of
halogen,
hydroxy,
alkyl,
alkenyl,
haloalkyl,
alkoxy,
alkylthio, and
—N(R$_3$)$_2$; and each R$_3$ is independently selected from the group consisting of hydrogen and alkyl;

with the proviso that when L is —NH—S(O)$_2$— and R$_A$ and R$_B$ join to form an unsubstituted benzene ring, R$_{1-1}$ is a linear or branched aliphatic group having greater than 16 carbon atoms, optionally including one or more unsaturated carbon-carbon bonds;

or a pharmaceutically acceptable salt thereof.

2. The compound or salt of claim 1 wherein R$_A$ and R$_B$ form a fused benzene ring which is unsubstituted.

3. The compound or salt of claim 1 wherein L is a bond or a functional linking group selected from the group consisting of —NH—C(O)—, —NH—S(O)$_2$—, and —NH—C(O)—N(R$_3$)—.

4. The compound or salt of claim 1 wherein R$_{1-1}$ is a linear or branched aliphatic group having 12-20 carbon atoms, optionally including one or more unsaturated carbon-carbon bonds.

5. The compound or salt of claim 4 wherein R$_{1-1}$ is a straight chain C$_{12}$-C$_{20}$ alkyl.

6. The compound or salt of claim 1 wherein R$_1$ has the formula C$_{1-5}$alkylene-L-R$_{1-1}$ and the C$_{1-5}$alkylene is optionally interrupted with one —O— group.

7. The compound or salt of claim 1 wherein R$_2$ is selected from the group consisting of hydrogen, alkyl, and alkylene-O-alkyl.

8. A compound of the following Formula III:

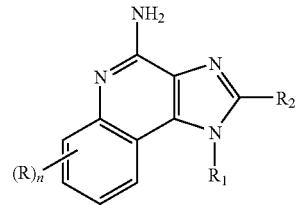

wherein:
R$_1$ has the formula alkylene-L-R$_{1-1}$, alkenylene-L-R$_{1-1}$, or alkynylene-L-R$_{1-1}$, wherein:
the alkylene, alkenylene, and alkynylene groups are optionally interrupted with one or more —O— groups;
L is a bond or a functional linking group selected from the group consisting of —NH—S(O)$_2$—, —NH—C(O)—, —NH—C(S)—, —NH—S(O)$_2$—NR$_3$—, —NH—C(O)—NR$_3$—, —NH—C(S)—NR$_3$—, —NH—C(O)—O—, —O—, —S—, and —S(O)$_2$—; and
R$_{1-1}$ is a linear or branched aliphatic group having at least 11 carbon atoms, optionally including one or more unsaturated carbon-carbon bonds;
R is selected from the group consisting of
halogen,
hydroxy,
alkyl,
alkenyl,
haloalkyl,
alkoxy,
alkylthio, and
—N(R$_3$)$_2$;
n is 0 to 4;
R$_2$ is selected from the group consisting of:
hydrogen;
alkyl;
alkenyl;
aryl;
heteroaryl;
heterocyclyl;
alkylene-Y-alkyl;
alkylene-Y-alkenyl;
alkylene-Y-aryl; and
alkyl or alkenyl substituted by one or more substituents selected from the group consisting of:
—OH;
halogen;
—N(R$_4$)$_2$;
—C(O)—C$_{1-10}$alkyl;
—C(O)—O—C$_{1-10}$alkyl;
—N$_3$;
aryl;
heteroaryl;
heterocyclyl;
—C(O)-aryl; and
—C(O)-heteroaryl;
wherein aryl is phenyl, naphthyl, biphenyl, fluorenyl or indenyl; heteroaryl is furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, or 1-oxidopyridyl; and heterocyclyl is the fully saturated or partially unsaturated derivative any one of the above heteroaryl groups, pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, or homopiperidinyl;

Y is —O— or —S(O)$_{0-2}$—;

each $R_4$ is independently selected from the group consisting of hydrogen, $C_{1-10}$alkyl, and $C_{2-10}$alkenyl; and $R_3$ is selected from the group consisting of hydrogen and alkyl;

with the proviso that when L is —NH—S(O$_2$)—, and n is 0, $R_{1-1}$ is a linear or branched aliphatic group having at least 16 carbon atoms, optionally including one or more unsaturated carbon-carbon bonds;

or a pharmaceutically acceptable salt thereof.

9. The compound or salt of claim 8 wherein n is 0.

10. A pharmaceutical composition comprising a therapeutically effective amount of a compound or salt of claim 1 in combination with a pharmaceutically acceptable carrier.

11. A pharmaceutical composition comprising a therapeutically effective amount of a compound or salt of claim 8 in combination with a pharmaceutically acceptable carrier.

12. A method of vaccinating an animal comprising administering an effective amount of a compound or salt of claim 1 to the animal as a vaccine adjuvant.

13. A method of vaccinating an animal comprising administering an effective amount of N-(2-{2-[4-amino-2-(2-methoxyethyl)-1H-imidazo[4,5-c]quinolin-1-yl]ethoxy}ethyl)hexadecanamide to the animal as a vaccine adjuvant.

14. A method of vaccinating an animal comprising administering an effective amount of a compound or salt of claim 8 to the animal as a vaccine adjuvant.

* * * * *